(12) United States Patent
Hondo et al.

(10) Patent No.: US 10,202,399 B2
(45) Date of Patent: Feb. 12, 2019

(54) DIHYDROXY AROMATIC HETEROCYCLIC COMPOUND

(71) Applicant: Takeda Pharmaceutical Company Limited, Osaka (JP)

(72) Inventors: Takeshi Hondo, Tokyo (JP); Keita Nakanishi, Tokyo (JP); Tatsuya Niimi, Tokyo (JP); Masaichi Warizaya, Tokyo (JP); Ichiji Namatame, Tokyo (JP); Katsuya Harada, Tokyo (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 15/388,267

(22) Filed: Dec. 22, 2016

(65) Prior Publication Data

US 2017/0107226 A1    Apr. 20, 2017

Related U.S. Application Data

(60) Continuation of application No. 14/885,037, filed on Oct. 16, 2015, now Pat. No. 9,562,020, which is a
(Continued)

(30) Foreign Application Priority Data

Nov. 15, 2011   (JP) ................. 2011-250143

(51) Int. Cl.

| | |
|---|---|
| *C07D 213/69* | (2006.01) |
| *A61K 31/44* | (2006.01) |
| *C07D 491/056* | (2006.01) |
| *C07D 403/12* | (2006.01) |
| *C07D 401/14* | (2006.01) |
| *C07D 405/14* | (2006.01) |
| *A61K 31/4412* | (2006.01) |
| *A61K 31/4418* | (2006.01) |
| *A61K 31/4427* | (2006.01) |
| *A61K 31/443* | (2006.01) |
| *A61K 31/4433* | (2006.01) |
| *A61K 31/4439* | (2006.01) |
| *A61K 31/444* | (2006.01) |
| *A61K 31/496* | (2006.01) |
| *A61K 31/50* | (2006.01) |
| *A61K 31/501* | (2006.01) |
| *A61K 31/5377* | (2006.01) |
| *A61K 31/551* | (2006.01) |

(Continued)

(52) U.S. Cl.
CPC ........ *C07D 491/056* (2013.01); *A61K 31/443* (2013.01); *A61K 31/444* (2013.01); *A61K 31/4412* (2013.01); *A61K 31/4418* (2013.01); *A61K 31/4427* (2013.01); *A61K 31/4433* (2013.01); *A61K 31/4439* (2013.01); *A61K 31/496* (2013.01); *A61K 31/50* (2013.01); *A61K 31/501* (2013.01); *A61K 31/5377* (2013.01); *A61K 31/551* (2013.01); *C07D 213/69* (2013.01); *C07D 237/16* (2013.01); *C07D 253/07* (2013.01); *C07D 401/06* (2013.01); *C07D 401/10* (2013.01); *C07D 401/12* (2013.01); *C07D 401/14* (2013.01); *C07D 403/06* (2013.01); *C07D 403/12* (2013.01); *C07D 405/06* (2013.01); *C07D 405/10* (2013.01); *C07D 405/12* (2013.01); *C07D 405/14* (2013.01); *C07D 409/06* (2013.01); *C07D 409/12* (2013.01); *C07D 413/06* (2013.01); *C07D 413/10* (2013.01); *C07D 413/12* (2013.01); *C07D 413/14* (2013.01); *C07D 417/06* (2013.01); *C07D 417/12* (2013.01); *C07D 417/14* (2013.01); *C07D 471/04* (2013.01); *C07D 471/10* (2013.01); *C07D 487/04* (2013.01)

(58) Field of Classification Search
None
See application file for complete search history.

(56) References Cited

U.S. PATENT DOCUMENTS

| | | | |
|---|---|---|---|
| 4,193,916 A | 3/1980 | Back et al. | |
| 4,743,685 A | 5/1988 | Breuer et al. | |

(Continued)

FOREIGN PATENT DOCUMENTS

| | | |
|---|---|---|
| BE | 859 477 | 4/1979 |
| DE | 27 45 024 | 4/1978 |

(Continued)

OTHER PUBLICATIONS

Sherif et al, Der Pharma Chemica, 2(6): pp. 105-116 (Year: 2010).*
Adage, Tiziana, et al., "In vitro and in vivo pharmacological profile of AS057278, a selective D-amino acid oxidase inhibitor with potential antipsychotic properties," European Neuropsychopharmacology, vol. 18, pp. 200-214 (2008).
Aroyan, A.A., et al., "Pyrimidine derivatives. XXXVI. Synthesis and IR and mass spectra of 2-(p-alkoxybenzyl)-4,5-dihydroxypyrimidines," Armyanski Khimicheskii Zhurnal, vol. 27, pp. 963-968, CAS Database Accession No. 1975::140063 Caplus (1974) English Abstract Only Abstract.
(Continued)

*Primary Examiner* — Zinna Northington Davis
(74) *Attorney, Agent, or Firm* — Finnegan, Henderson, Farabow, Garrett & Dunner LLP

(57) ABSTRACT

Provided is a compound having a D-amino acid oxidase (DAAO) inhibitory action, and useful as, for example, a prophylaxis and/or therapeutic agent for schizophrenia or neuropathic pain. The present inventors have studied a compound that inhibits DAAO, and confirm that a dihydroxy aromatic heterocyclic compound has a DAAO inhibitory action, and completed the present invention. That is, the dihydroxy aromatic heterocyclic compound of the present invention has a good DAAO inhibitory action, and can be used as a prophylaxis and/or therapeutic agent for, for example, schizophrenia or neuropathic pain.

12 Claims, 1 Drawing Sheet

Related U.S. Application Data division of application No. 14/358,162, filed as application No. PCT/JP2012/079521 on Nov. 14, 2012, now Pat. No. 9,212,147.

(51) Int. Cl.

| | | |
|---|---|---|
| C07D 401/06 | (2006.01) | |
| C07D 401/12 | (2006.01) | |
| C07D 237/16 | (2006.01) | |
| C07D 405/12 | (2006.01) | |
| C07D 409/12 | (2006.01) | |
| C07D 413/12 | (2006.01) | |
| C07D 417/12 | (2006.01) | |
| C07D 417/14 | (2006.01) | |
| C07D 471/04 | (2006.01) | |
| C07D 471/10 | (2006.01) | |
| C07D 487/04 | (2006.01) | |
| C07D 403/06 | (2006.01) | |
| C07D 405/06 | (2006.01) | |
| C07D 409/06 | (2006.01) | |
| C07D 413/06 | (2006.01) | |
| C07D 413/10 | (2006.01) | |
| C07D 417/06 | (2006.01) | |
| C07D 253/07 | (2006.01) | |
| C07D 401/10 | (2006.01) | |
| C07D 405/10 | (2006.01) | |
| C07D 413/14 | (2006.01) | |

(56) References Cited

U.S. PATENT DOCUMENTS

| | | |
|---|---|---|
| 5,244,890 A | 9/1993 | Yamanaka et al. |
| 5,401,734 A | 3/1995 | Yamanaka et al. |
| 5,532,354 A | 7/1996 | Yamanaka et al. |
| 5,962,480 A | 10/1999 | Moriguchi et al. |
| 9,180,122 B2 | 11/2015 | Farnaby et al. |
| 9,212,147 B2 | 12/2015 | Hondo et al. |
| 9,290,456 B2 | 3/2016 | Farnaby et al. |
| 9,562,020 B2 | 2/2017 | Hondo et al. |
| 9,931,340 B2 | 4/2018 | Farnaby et al. |
| 2010/0022526 A1 | 1/2010 | Lamberth et al. |
| 2013/0052281 A1 | 2/2013 | Farnaby et al. |
| 2014/0243353 A1 | 8/2014 | Farnaby et al. |
| 2014/0248378 A1 | 9/2014 | Cockcroft et al. |
| 2014/0336165 A1 | 11/2014 | Hondo et al. |
| 2015/0030704 A1 | 1/2015 | Farnaby et al. |
| 2015/0329495 A1 | 11/2015 | Farnaby et al. |
| 2016/0039771 A1 | 2/2016 | Hondo et al. |
| 2017/0107226 A1 | 4/2017 | Hondo et al. |
| 2017/0173007 A1 | 6/2017 | Farnaby et al. |
| 2018/0177780 A1 | 6/2018 | Farnaby et al. |

FOREIGN PATENT DOCUMENTS

| | | |
|---|---|---|
| EP | 0 180 298 | 5/1986 |
| EP | 0 593 110 A1 | 4/1994 |
| EP | 2 314 586 | 4/2011 |
| GB | 2 025 416 | 1/1980 |
| JP | 61-57563 | 3/1986 |
| JP | 62-84082 | 4/1987 |
| JP | 64-29367 | 1/1989 |
| JP | 1-202875 | 8/1989 |
| JP | 1-261392 | 10/1989 |
| JP | 02-028187 | 1/1990 |
| JP | 5-255344 | 10/1993 |
| JP | 09-025234 | 1/1997 |
| JP | 2001-519416 | 10/2001 |
| JP | 2007-517056 | 6/2007 |
| WO | WO 95/11235 | 4/1995 |
| WO | WO 99/10331 | 3/1999 |
| WO | WO 02/053543 | 7/2002 |
| WO | WO 03/047558 A2 | 6/2003 |
| WO | WO 03/062233 | 7/2003 |
| WO | WO 2004/094408 | 11/2004 |
| WO | WO 2005/061458 | 7/2005 |
| WO | WO 2005/066135 | 7/2005 |
| WO | WO 2006/135828 | 12/2006 |
| WO | WO 2007/119434 A1 | 10/2007 |
| WO | WO 2008/089453 | 7/2008 |
| WO | WO 2008/115381 | 9/2008 |
| WO | WO 2008/116301 | 10/2008 |
| WO | WO 2008/156607 | 12/2008 |
| WO | WO 2009/020814 | 2/2009 |
| WO | WO 2010/017418 | 2/2010 |
| WO | WO 2010/058314 A1 | 5/2010 |
| WO | WO 2010/090737 A1 | 8/2010 |
| WO | WO 2011/046920 | 4/2011 |
| WO | WO 2011/109254 | 9/2011 |
| WO | WO 2011/109261 | 9/2011 |
| WO | WO 2011/109267 | 9/2011 |
| WO | WO 2013/003383 A1 | 1/2013 |
| WO | WO 2013/004995 | 1/2013 |
| WO | WO 2013/004996 | 1/2013 |
| WO | WO 2013/027000 | 2/2013 |
| WO | WO 2013/073577 | 5/2013 |
| WO | WO 2014/096757 A1 | 6/2014 |

OTHER PUBLICATIONS

Bluth, R. "Pharmacological Characterization of Novel Pyridazines," Pharmazie, vol. 36, No. 11. pp. 775-777 (1981).
Corrected Notice of Allowance dated Aug. 19 2015, in U.S. Appl. No. 14/358,162.
Division of Medicinal Chemistry Scientific Abstracts for the 244th National Meeting and Expostiion, Aug. 19-23, 2012, Philadelphia, PA, Publication date: Jul. 6, 2012.
Duplantier, Allen J., et al., Discovery, SAR, and Pharmacolkinetics of a Novel 3-Hydroxyquinolin-2(1H)-one Series of Potent D-Amino Acid Oxidase (DAAO) Inhibitors, J. Med. Chem, vol. 52, pp. 3576-3585 (2009).
Dyumaev, K.M., et al., "Aminomethylation of 2,3-dihydroxy- and 3-hydroxy-2-methoxyyridine,", Tr. Samarkand, Univ., No. 180, XP-002684179, (1970). English Abstract Only Abstract.
English language abstract of JP 02-028187, filed Jun. 6, 1989.
English language abstract of JP 09-025234, filed Jul. 12, 1995.
Feng, Yuchen et al., "Photolytic and Microbial Degradation of 3,5,6-tricholoro-2-pyridinol," Environmental Toxicology and Chemistry, vol. 17, No. 5. pp. 814-819 (1998).
Ferraris, Dana, et al., "Synthesis and Biological Evaluation of D-Amino Acid Oxidase Inhibitors," J. Med. Chem, vol. 51, pp. 3357-3359 (2008).
Hackam, D. G. et al. "Translation of Research Evidence From Animals to Humans," J. American Medical Association, 296(14), 2006, pp. 1731-1732.
Hondo, Takeshi, et al., "4-Hydroxypyridazin-3(2H)-one derivatives as novel D-amino acid oxidase inhibitors," J. Med. Chem, vol. 56, pp. 3582-3592 (2013).
International Search Report for International Patent Application No. PCT/GB2012/000573, dated Sep. 10, 2012.
International Search Report for International Patent Application No. PCT/GB2012/000574, dated Oct. 11, 2012.
International Search Report for International Patent Application No. PCT/GB2012/000672, dated Oct. 1, 2012.
International Search Report for International Patent Application No. PCT/JP2012/079521, dated Jan. 22, 2013.
International Search Report for International Patent Application No. PCT/GB2013/000552, dated Mar. 20, 2014.
Jordan, V.C., "Tamoxifen: A most unlikely pioneering medicine," Nature Reviews: Drug Discovery, 2, 2003 pp. 205-213.
Nakamura, Akatida, et al., "Studies on Prototropic Tautomerism in Nitrogen Heterocyclic Compounds. II. A Ring-Chain Tautomerism in 3-Hydroxy-6-(2-oxocycloalkyl)-methyl)-2(1H)-pyridone and 3-Hydroxy-6-(3-oxoalkyo)-2(1H)-pyridone Derivatives," Chem. Pharm. Bull., vol. 17, pp. 425-433 (1969).

(56) References Cited

OTHER PUBLICATIONS

Nakamura, Akitada, et al., "Studies on Prototropic Tautomerism in Nitrogen Heterocyclic Compounds. I. The Mannich Reaction of 2(1H)-Pyridone and 3-Hydroxy-2(1H)-pyridone," Chem. Pharm. Bull, vol. 16, pp. 1466-1471 (1968).
Notice of Allowance dated Jul. 17, 2015, in U.S. Appl. No. 14/358,162.
Notice of Allowance dated Jul. 9, 2015, in U.S. Appl. No. 14/131,343.
Office Action (Restriction Requirement) dated Jan. 24, 2013, in U.S. Appl. No. 13/591,859.
Office Action (Restriction Requirement) dated Mar. 16, 2015, in U.S. Appl. No. 14/240,045.
Office Action dated Jun. 12, 2015, in U.S. Appl. No. 14/240,045.
Office Action dated Mar. 18, 2015, in U.S. Appl. No. 14/358,162.
Office Action dated Mar. 19, 2015, in U.S. Appl. No. 14/131,343.
Office Action dated May 8, 2015, in U.S. Appl. No. 13/591,859.
Office Action dated Sep. 19, 2013, in U.S. Appl. No. 13/591,859.
Piskala, A. et al., Reaction of 3,5,6-Trichloro-1,2,4-Triazine with Simple Nucleophiles, *Institute of Organic Chemistry and Biochemistry, Czechoslovak Academy of Sciences,* 166 10 Prague 6, Received Dec. 13, 1974, vol. 40, Issue 9, 1975, pp. 2680-2688.
Sparey, Tim, et al., "The discovery of fused pyrrole carboxylic acids as novel, potent D-amino acid oxidase (DAO) inhibitors," Bio. & Med. Chem. Letters, vol. 18, pp. 3386-3391 (2008).
Sunagawa et al., "Synthesis and Antibacterial Activity of Novel Carbapenems with a Catechol or Hydroxypyridone moiety," Journal of Antibiotics (1994), 47(11), 1354-8.
U.S. Appl. No. 13/591,859, filed Aug. 27, 2012.
U.S. Appl. No. 14/131,337, filed Jan. 7, 2014.
U.S. Appl. No. 14/131,343, filed May 8, 2014.
U.S. Appl. No. 14/240,045, filed Feb. 21, 2014.
U.S. Appl. No. 14/358,162, filed May 14, 2014.
U.S. Appl. No. 14/652,484, filed Jun. 16, 2015.
Almond et al., "Behavioral and biochemical characterization of a mutant mouse strain lacking d-amino acid oxidase activity and its implications for schizophrenia," Molecular and Cellular Neurosciences, vol. 32, No. 4, pp. 324-334 (2006).
CAS Database Accession No. 1972 564402 (1984). (Dyumaev).
CAS Database Accession No. 1978 512324 (1984).
CAS Database Accession No. RN 37749-03-4 (1984).
Hashimoto et al., "Mice lacking d-amino acid oxidase activity display marked attenuation of stereotypy and ataxia induced by MK-081," Brain Research, vol. 1033, No. 2, pp. 210-215 (2005).
International Search Report and Written Opinion of the International Search Authority for International Application No. PCT/GB2015/050654, dated Apr. 29, 2015.
Panourias, I. G. et al., "Intrathecal Baclofen in Current Neuromodulatory Practice: Established Indications and Emerging Applications," *Acta Neurochir Suppl.* (2007) 97(1):145-154, © Springer-Verlag 2007, 10 pages.
U.S. Appl. No. 14/885,037, filed Oct. 16, 2015.
U.S. Appl. No. 15/014,336, filed Feb. 3, 2016.
U.S. Appl. No. 15/899,561, filed Feb. 20, 2018.
Vree et al., "Novel oxidative pathways of sulphapyridine and sulphadiazine by the turtle *Pseudemys scripta elegans,*" The Veterinary Quarterly, vol. 13, No. 4, pp. 218-224 (Oct. 1991).

* cited by examiner

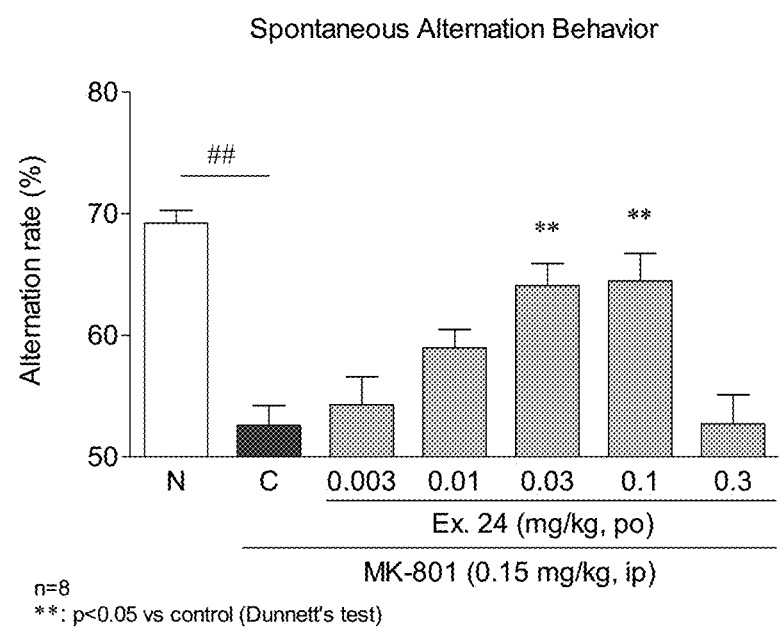

DIHYDROXY AROMATIC HETEROCYCLIC COMPOUND

This is a continuation of U.S. application Ser. No. 14/885,037, filed Oct. 16, 2015, which is a divisional application of U.S. application Ser. No. 14/358,162, filed May 14, 2014, which is a national stage entry under 35 U.S.C. § 371 of International Application No. PCT/JP2012/079521, filed Nov. 14, 2012, which claims priority to Japanese Patent Application No. 2011-250143, filed Nov. 15, 2011. The contents of all four applications are herein incorporated by reference.

TECHNICAL FIELD

The present invention relates to a dihydroxy aromatic heterocyclic compound useful as an active ingredient of a pharmaceutical composition, for example, a pharmaceutical composition for the treatment of diseases associated with D-amino acid oxidase (DAAO).

BACKGROUND ART

Recently, a relationship between D-serine and psychiatric disease, particularly schizophrenia, has been pointed out. For example, it has been reported that the D-serine concentration is low in both the serum and cerebrospinal fluid of schizophrenic patients (non-patent document 1, non-patent document 2). Moreover, it has been reported that the combined use of D-serine and existing antipsychotic drugs improves positive symptoms, negative symptoms and cognitive function in schizophrenic patients (non-patent document 3).

D-serine is produced from L-serine by serine racemase, and metabolized by D-amino acid oxidase (DAAO). Since DAAO is widely distributed in the brain (non-patent document 4), it is expected that the intracerebral D-serine concentration will be increased and the cognitive function will be improved by inhibiting DAAO.

In addition, DAAO produces, along with the D-serine oxidation, reactive oxygen species such as hydrogen peroxide, which are toxic metabolites. Reactive oxygen species are known to participate in neuropathic pain such as hyperalgesia and the like (non-patent document 5). Furthermore, the above-mentioned toxic metabolite may cause neuron injury. Therefore, inhibition of DAAO is considered to be useful for psychiatric diseases including schizophrenia and bipolar disorder, diseases damaging learning and memory such as Alzheimer's disease, Parkinson's disease, Huntingdon's disease and the like, and further, neuropathic pain and neurodegenerative diseases.

Benzoic acid is known as a DAAO inhibitor (non-patent document 6), and it is known that benzoic acid suppresses hyperalgesia, alllodynia, and neuropathic pain (non-patent documents 7, 8), and other DAAO inhibitors suppress alllodynia in a neuropathic pain model (patent document 1, patent document 2), and learning•memory•dementia (patent document 3).

Some compounds having a DAAO inhibitory action have been reported and, for example, a compound represented by the following formula (A) can be mentioned (non-patent document 9).

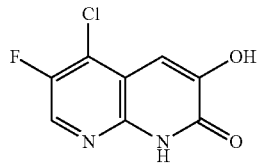

(A)

In addition, a pyrrole carboxylic acid derivative (patent document 1, patent document 2) has been reported to show a DAAO inhibitory action.

DOCUMENT LIST

Patent Documents

[patent document 1] WO2005/066135
[patent document 2] WO2008/005456
[patent document 3] WO2003/039540

Non-patent Documents

[non-patent document 1] Arch Gen Psychiatry, 2003, vol. 60, No. 6, pages 572-576
[non-patent document 2] Progress in Neuro-Psychopharmacology and Biological Psychiatry, 2005, vol. 29, No. 5, pages 767-769
[non-patent document 3] Biological Psychiatry, 2005, vol. 57, No. 6, pages 577-585
[non-patent document 4] Journal of Neurocytology, 1999, vol. 28, No. 3, pages 169-185
[non-patent document 5] Pain, 2004, vol. 111, Nos. 1, 2, pages 116-124
[non-patent document 6] Journal of Biological Chemistry, 1956, vol. 223, No. 1, pages 75-83
[non-patent document 7] Cellular and Molecular Neurobiology, 2008, vol. 28, No. 4, pages 581-91
[non-patent document 8] Journal of Pharmacology and Experimental Therapeutics, 2010, vol. 332, No. 1, pages 248-254
[non-patent document 9] Journal of Medicinal Chemistry, 2009, vol. 52, No. 1, pages 3576-3585

SUMMARY OF THE INVENTION

Problems to be Solved by the Invention

A dihydroxy aromatic heterocyclic compound useful as an active ingredient of a pharmaceutical composition, for example, a pharmaceutical composition for the treatment of diseases associated with D-amino acid oxidase (DAAO) is provided.

Means of Solving the Problems

Recently, the FBDD (Fragment-Based Drug Design) method has been attracting attention as a method for searching inhibitors. The present inventors have conducted intensive studies using the FBDD method and found that the compounds of the following formula (I) or a salt thereof has a good DAAO inhibitory action, and is particularly useful as an active ingredient of a pharmaceutical composition for the prophylaxis or treatment of schizophrenia and neuropathic pain, which resulted in the completion of the present invention. Accordingly, the present invention relates to a compound of the formula (I) or a salt thereof, a pharmaceutical composition containing a compound of the formula (I) or a salt thereof, and an excipient, particularly, a pharmaceutical composition for the treatment of diseases involving DAAO, for example, schizophrenia and neuropathic pain.

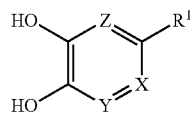

(I)

wherein each symbol shows the following meaning:

X is $CR^2$ or N,

Y is CH or N, provided when X is $CR^2$, Y is N,

Z is CH, provided when both X and Y are N, Z is optionally N, $R^1$ is H, $C_{1-10}$ alkyl, -lower alkylene-$OR^3$, halogen, optionally substituted cycloalkyl, -$L^1$-$R^4$ or -$L^2$-N(—$R^5$)$R^6$, $R^2$ is H, lower alkyl, halogen or -lower alkylene-aryl, $R^3$ is H or lower alkyl, $L^1$ is -lower alkylene-, -lower alkenylene-, -lower alkylene-O—, -lower alkylene-S(O)$_m$— or -lower alkylene-C(O)—, $L^2$ is -lower alkylene-, -lower alkylene-S(O)$_2$— or -lower alkylene-C(O)—, $R^4$ is optionally substituted cycloalkyl, optionally substituted aryl, optionally substituted nonaromatic heterocycle or optionally substituted aromatic heterocycle, $R^5$ is H, lower alkyl, optionally substituted cycloalkyl or optionally substituted aryl, $R^6$ is lower alkyl, -$L^{21}$-(optionally substituted cycloalkyl), -$L^{21}$-(optionally substituted aryl), -$L^{21}$-(optionally substituted nonaromatic heterocycle), -$L^{21}$-(optionally substituted aromatic heterocycle), -lower alkylene-$OR^7$ or -lower alkylene-N($R^8$)$_2$, $R^7$ is H or lower alkyl, $R^8$ are the same or different and each is lower alkyl, $L^{21}$ is a bond or -lower alkylene-, and m is an integer of 0 to 2.

Unless particularly specified, when a symbol in a certain chemical formula in the present specification is also used in another chemical formula, the same symbol has the same meaning.

In the formula (I), for example, when $L^1$ is -lower alkylene-O—, -lower alkylene-S(O)$_m$— or -lower alkylene-C(O)—, it means a compound of the following formula (II) or a salt thereof.

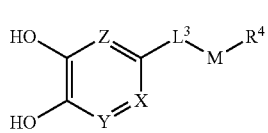

(II)

wherein $L^3$ is lower alkylene, and M is O, S(O)$_m$ or C(O).

In the formula (I), for example, when $L^2$ is -lower alkylene-S(O)$_2$— or -lower alkylene-C(O)—, it means a compound of the following formula (III) or a salt thereof.

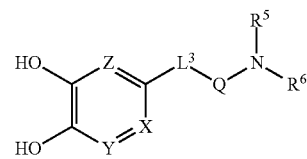

(III)

wherein Q is S(O)$_2$ or C(O).

Moreover, the present invention relates to a pharmaceutical composition containing a compound of the formula (I) or a salt thereof for the treatment of a diseases involving DAAO, particularly schizophrenia and neuropathic pain. The pharmaceutical composition encompasses a therapeutic agent containing the compound of the formula (I) or a salt thereof for diseases involving DAAO, particularly, a therapeutic agent for schizophrenia or neuropathic pain.

Moreover, the present invention relates to use of a compound of the formula (I) or a salt thereof for the production of a pharmaceutical composition for the treatment of diseases involving DAAO, particularly, schizophrenia, neuropathic pain, use of a compound of the formula (I) or a salt thereof for the treatment of diseases involving DAAO, particularly, schizophrenia, neuropathic pain, a compound of the formula (I) or a salt thereof for the treatment of diseases involving DAAO, particularly, schizophrenia, neuropathic pain, and a method of treating diseases involving DAAO, particularly, schizophrenia, neuropathic pain, comprising administering an effective amount of a compound of the formula (I) or a salt thereof to a target. The "target" is a human or other animal in need of the prophylaxis or treatment thereof and, in a certain embodiment, a human in need of the prophylaxis or treatment thereof.

Effect of the Invention

The compound of the formula (I) or a salt thereof has a DAAO inhibitory action, and can be used as, for example, a prophylaxis and/or therapeutic agent for schizophrenia or neuropathic pain.

BRIEF DESCRIPTION OF THE DRAWINGS

FIG. 1 shows an improvement action of the test compound Ex.24 on MK-801 (dizocilpine)-induced impaired spontaneous alternation performance in mice, wherein Ex. shows the Example No. mentioned later. On the horizontal axis, N denotes a normal group (physiological saline+solvent administration), and C shows a solvent group (MK-801+ solvent administration). The spontaneous alternation behavior rate (Alternation rate (%)) on the vertical axis is calculated by the following formula and becomes an index of cognitive function.

Alternation rate(%)=100×number of spontaneous alternation behavior/(total number of arm entries-2)

wherein the number of spontaneous alternation behavior shows the number of different arm entries sustained for three times, for example, A→B→C. In the Table, ## means a significant difference as compared to a normal group at a critical rate of less than 1% as a result of Student's t-test. In the Table, ** means a significant difference as compared to a solvent group at a critical rate of less than 1% as a result of Dunnett's multiple comparison test. n=8 means that 8 mice were in each group.

DESCRIPTION OF EMBODIMENTS

The present invention is explained in detail in the following.

In the present specification, unless otherwise specified, "alkyl", "alkylene", "alkenylene" and "alkynylene" mean straight chain or branched hydrocarbon chain.

The "lower alkyl" is straight chain or branched alkyl having a carbon number of 1 to 6 (hereinafter to be abbreviated as $C_{1-6}$), for example, methyl, ethyl, n-propyl, isopropyl, n-butyl, isobutyl, sec-butyl, tert-butyl, n-pentyl, n-hexyl or the like. It is $C_{1-4}$ alkyl in another embodiment, methyl, ethyl or n-propyl in a still another embodiment, and methyl in a yet another embodiment.

The "lower alkylene" is straight chain or branched $C_{1-6}$ alkylene, for example, methylene, ethylene, trimethylene, tetramethylene, pentamethylene, hexamethylene, propylene, butylene, methylmethylene, ethylethylene, 1,2-dimethylethylene, 1,1,2,2-tetramethylethylene, 1-methylbutylene or the like. It is $C_{1-4}$ alkylene in another embodiment, methylene, ethylene, or propylene in a still another embodiment, methylene in a still another embodiment, ethylene in a still another embodiment, and propylene in a yet another embodiment.

The "lower alkenylene" is straight chain or branched $C_{2-6}$ alkenylene, for example, vinylene, propenylene, butenylene, pentenylene, hexenylene, 1,3-butadienylene, 1,3-pentadienylene or the like. It is $C_{2-4}$ alkenylene in another embodiment, and vinylene in a yet another embodiment.

The "lower alkynylene" is straight chain or branched $C_{2-6}$ alkynylene, for example, ethynylene, propynylene, butynylene, pentynylene, hexynylene, 1,3-butadiynylene, 1,3-pentadiynylene or the like. It is $C_{2-4}$ alkynylene in another embodiment, and ethynylene in a yet another embodiment.

The "halogen" is F, Cl, Br or I. It is F or Cl in another embodiment, and F in a yet another embodiment.

The "cycloalkyl" is a $C_{3-10}$ saturated hydrocarbon ring group. The cycloalkyl may have bridged, may have some unsaturated bonds, and may be fused with a benzene ring. Specific examples include cyclopropyl, cyclopentyl, cyclohexyl, cyclohexenyl, adamantyl, bicyclo[4.2.0]octa-1,3,5-trienyl, 2,3-dihydro-1H-indanyl, 1,2,3,4-tetrahydronaphthalenyl, indanyl, a fluorenyl group and the like. In another embodiment, it is cyclohexyl.

The "aryl" is a $C_{6-14}$ monocyclic to tricyclic aromatic hydrocarbon ring group. Specific examples include phenyl, naphthyl, anthranyl and the like. It is phenyl in another embodiment, and naphthyl in a yet another embodiment.

The "aromatic heterocycle" is a 5- or 6-membered aromatic heterocyclic group containing one or more hetero atoms selected from O, N and S as ring-constituting atoms, and the aromatic heterocycle may be fused with cycloalkyl, aryl or a monocyclic aromatic heterocycle. Specific examples include pyrrolyl, imidazolyl, pyrazolyl, thienyl, thiazolyl, isothiazolyl, oxazolyl, isoxazolyl, oxadiazolyl, pyridyl, pyrimidinyl, pyrazinyl, pyridazinyl, indolyl, benzimidazolyl, indazolyl, quinolyl, imidazo[1,2-a]pyridyl, benzotriazolyl, benzothiazolyl, benzoxazolyl, quinoxalinyl, 1,8-a-dihydroimidazo[1,2-a]pyridyl and the like. In another embodiment, it is imidazolyl, pyridyl, benzimidazolyl or quinolyl.

The "nonaromatic heterocycle" is a 3- to 7-membered nonaromatic heterocyclic group containing one or more hetero atoms selected from O, N and, S as ring-constituting atoms, and the nonaromatic heterocycle may be fused with cycloalkyl, aryl, monocyclic aromatic heterocycle or monocyclic nonaromatic heterocycle, may have a partially unsaturated bond, and may form a spiro ring with cycloalkyl or a nonaromatic heterocycle. In addition, the sulfur atom, which is a ring-constituting atom, may be oxidized. Specific examples include azetidinyl, pyrrolidinyl, piperidyl, imidazolidinyl, pyrazolidinyl, piperazinyl, morpholinyl, thiomorpholinyl, 1,1-dioxidothiomorpholinyl, tetrahydropyranyl, azepanyl, diazepanyl, indolinyl, 2,3-dihydrobenzoimidazolyl, octahydropyrrolo[1,2-a]pyrazinyl, 1,2,3,4-tetrahydroquinazolinyl, benzodioxolyl, 2,3-dihydro-1,4-benzodioxinyl, 2,3-dihydrobenzofuranyl, 1,3-dihydro-spiro[2H-indene-2,4'-piperidinyl], 2-azaspiro[5.5]undecanyl, 3,4-dihydro-spiro[naphthalene-1(2H),3'-piperidinyl], 3,9-diazaspiro[5.5]undecanyl, 6,7-dihydro-5H-pyrrolo[3,4-b]pyridyl, carbazolyl, 1,2,3,4-tetrahydro-2,7-naphthyridinyl, 2,3-dihydro-1H-pyrrolo[3,4-c]pyridyl, 6,7-dihydro-5H-pyrrolo[3,4-b]pyridyl, 4,5,6,7-tetrahydro-1H-pyrazolo[3,4-c]pyridyl and the like. In another embodiment, it is pyrrolidinyl, piperidyl, or piperazinyl.

The "cyclic amino" is the above-mentioned "nonaromatic heterocycle" having a nitrogen atom, and is a nonaromatic heterocycle having a bond on the nitrogen atom. Examples thereof include azetidin-1-yl, pyrazolidin-1-yl, imidazolidin-1-yl, 1,4-diazepan-1-yl, pyrrolidin-1-yl, piperidin-1-yl, azepan-1-yl, piperazin-1-yl, morpholin-4-yl, thiomorpholin-4-yl, 1,1-dioxidothiomorpholin-4-yl and the like. It is pyrrolidin-1-yl, piperidin-1-yl, azepan-1-yl, piperazin-1-yl, morpholin-4-yl, thiomorpholin-4-yl or 1,1-dioxidothiomorpholin-4-yl in another embodiment, pyrrolidin-1-yl, piperidin-1-yl, morpholin-4-yl or 1,1-dioxidothiomorpholin-4-yl in a still another embodiment, 6-membered monocyclic cyclic amino in a still another embodiment, and piperidin-1-yl, morpholin-4-yl, or 1,1-dioxidothiomorpholin-4-yl in a yet another embodiment.

In the present specification, "optionally substituted" means being unsubstituted or having 1 to 5 substituents. It means unsubstituted or having 1 to 3 substituents in one embodiment, unsubstituted or having one substituent in another embodiment, and unsubstituted in a still another embodiment. When plural substituents are present, the respective substituents may be the same or different.

Examples of the substituent of the "optionally substituted cycloalkyl" for $R^1$, "optionally substituted cycloalkyl", "optionally substituted aryl", "optionally substituted nonaromatic heterocycle" and "optionally substituted aromatic heterocycle" for $R^4$, "optionally substituted cycloalkyl" and "optionally substituted aryl" for $R^5$ and "optionally substituted cycloalkyl", "optionally substituted aryl", "optionally substituted nonaromatic heterocycle" and "optionally substituted aromatic heterocycle" for $R^6$ of the formula (I) include substituents selected from the group consisting of group D1.

Group D1

(1) halogen,
(2) —OH,
(3) aryl optionally substituted by one or more substituents selected from the group consisting of halogen, —O-lower alkyl, lower alkyl optionally substituted by one or more halogens and —CN; —O-(aryl optionally substituted by one or more substituents selected from the group consisting of halogen, lower alkyl optionally substituted by one or more halogens, —O-lower alkyl and —C(O)O-lower alkyl); —C(O)-(aryl optionally substituted by one or more substituents selected from the group consisting of lower alkyl, —O-lower alkyl and halogen); and —C(O)-lower alkenylene-aryl, (4) —O-lower alkyl,
(5) aromatic heterocycle optionally substituted by one or more substituents selected from the group consisting of lower alkyl and aryl; —O-(aromatic heterocycle optionally substituted by one or more substituents selected from the group consisting of lower alkyl and halogen); and —C(O)-(aromatic heterocycle optionally substituted by one or more substituents selected from the group consisting of lower alkyl and halogen),
(6) nonaromatic heterocycle optionally substituted by one or more substituents selected from the group consisting of —OH, lower alkyl and oxo; —O-(nonaromatic heterocycle optionally substituted by one or more substituents selected from the group consisting of lower alkyl and halogen); and —C(O)-(nonaromatic heterocycle optionally substituted by one or more substituents selected from the group consisting of lower alkyl and halogen),
(7) —NH$_2$, —NH(lower alkyl) and —N(lower alkyl)$_2$,
(8) cycloalkyl and —C(O)-cycloalkyl,
(9) —C(O)O-lower alkyl,
(10) —C(O)-lower alkyl,
(11) —NH—C(O)-lower alkyl,
(12) —S(O)$_m$-lower alkyl, —S(O)$_m$-nonaromatic heterocycle, —S(O)$_m$-(aromatic heterocycle optionally substituted by one or more lower alkyl) and —S(O)$_m$-(aryl optionally substituted by one or more substituents selected from the group consisting of lower alkyl and halogen),
(13) —O—C(O)-lower alkyl,
(14) —C(O)—NH-aromatic heterocycle,
(15) -lower alkenylene-C(O)O-aryl,
(16) —NH-cycloalkyl,
(17) -lower alkenylene-C(O)O-alkyl, and
(18) lower alkyl and —O-lower alkyl, wherein the lower alkyl moiety is optionally substituted by one or more substituents selected from the group consisting of the substituents described in the above-mentioned (1)-(17), and
(19) oxo.

Another embodiment of group D1 includes
(1) halogen,
(2) —OH,
(3) aryl optionally substituted by one or more substituents selected from the group consisting of halogen, —O-lower alkyl and —CN; —O-(aryl optionally substituted by one or more substituents selected from the group consisting of halogen, lower alkyl optionally substituted by one or more halogens, —O-lower alkyl and —C(O)O-lower alkyl); —C(O)-(aryl optionally substituted by one or more substituents selected from the group consisting of —O-lower alkyl and halogen) and —C(O)-lower alkenylene-aryl,
(4) —O-lower alkyl and —O-(lower alkyl optionally substituted by one or more substituents selected from the group consisting of aryl substituted by one or more halogens and halogen),
(5) lower alkyl optionally substituted by one or more substituents selected from the group consisting of halogen, —OH, —N(lower alkyl)$_2$, —O-lower alkyl, cycloalkyl, aryl, —O-aryl, aromatic heterocycle, nonaromatic heterocycle and —C(O)-nonaromatic heterocycle,
(6) nonaromatic heterocycle, —O-nonaromatic heterocycle and —C(O)-nonaromatic heterocycle,
(7) aromatic heterocycle, —O-aromatic heterocycle and —C(O)-aromatic heterocycle,
(8) —C(O)O-lower alkyl,
(9) —C(O)-lower alkyl,
(10) cycloalkyl and —C(O)-cycloalkyl,
(11) —N(lower alkyl)$_2$,
(12) —NH—C(O)-lower alkyl,
(13) —S-lower alkyl, —S(O)$_2$-lower alkyl, —S(O)$_2$-nonaromatic heterocycle, —S(O)$_2$-(aromatic heterocycle optionally substituted by one or more lower alkyl), —S(O)$_2$-(aryl optionally substituted by one or more substituents selected from the group consisting of lower alkyl and halogen),
(14) —O—C(O)-lower alkyl,
(15) —C(O)—NH-aromatic heterocycle,
(16) —NH-cycloalkyl, and
(17) oxo.

A still another embodiment of group D1 includes
(1) halogen,
(2) aryl,
(3) —O-(lower alkyl optionally substituted by one or more halogens), and
(4) lower alkyl optionally substituted by one or more halogens.

A yet another embodiment of group D1 includes
(1) halogen,
(2) lower alkyl optionally substituted by one or more halogens, and
(3) aryl.

Another embodiment of an acceptable substituent of the "optionally substituted cycloalkyl" in the formula (I) includes
(1) lower alkyl optionally substituted by one or more substituents selected from the group consisting of halogen, —OH and —O-lower alkyl,
(2) halogen,
(3) —OH,
(4) aryl optionally substituted by one or more substituents selected from the group consisting of lower alkyl, halogen, —OH, —O-lower alkyl and C$_{3-10}$ cycloalkyl, and
(5) oxo.

A still another embodiment of an acceptable substituent of the "optionally substituted cycloalkyl" in the formula (I) is aryl.

Another embodiment of an acceptable substituent of the "optionally substituted aryl" in the formula (I) includes
(1) lower alkyl and —O-lower alkyl, wherein the lower alkyl moiety is optionally substituted by one or more substituents selected from the group consisting of halogen, —OH, —O-lower alkyl, aryl and —O-aryl,
(2) halogen,
(3) —OH,
(4) cycloalkyl and —O-cycloalkyl, wherein the cycloalkyl moiety is optionally substituted by one or more lower alkyl,
(5) cyano,
(6) aryl, —O-aryl, —C(O)-aryl and —C(O)-lower alkenylene-aryl, wherein the aryl moiety is optionally substituted by one or more substituents selected from the group consisting of lower alkyl, halogen, —OH, —O-lower alkyl, —O-(lower alkyl substituted by one or more halogens) and lower alkyl substituted by one or more halogens,
(7) heterocycle and —O-aromatic heterocycle, wherein the aromatic heterocycle moiety is optionally substituted by one or more substituents selected from the group consisting of lower alkyl and halogen,
(8) nonaromatic heterocycle and —O-nonaromatic heterocycle, wherein the nonaromatic heterocycle moiety is optionally substituted by one or more substituents selected from the group consisting of lower alkyl and halogen, (9) —C(O)-lower alkyl, —C(O)O-lower alkyl, —NH—C(O)-lower alkyl and -lower alkenylene-C(O)O-lower alkyl, wherein the lower alkyl moiety is optionally substituted by one or more substituents selected from the group consisting of halogen and —OH,

(10) —NH$_2$, —NHR$^8$ and —N(R$^8$)$_2$,

(11) —S-lower alkyl, —S(O)-lower alkyl and —S(O)$_2$-lower alkyl, and

(12) —NH—C(O)-lower alkyl.

A yet another embodiment of an acceptable substituent of the "optionally substituted aryl" in the formula (I) includes (1) lower alkyl optionally substituted by one or more substituents selected from the group consisting of —OH, —O-lower alkyl, halogen, aryl and —O-aryl, (2) halogen, (3) —O-(lower alkyl optionally substituted by one or more substituents selected from the group consisting of halogen and —OH), (4) aryl optionally substituted by one or more halogens, (5) —O-(aryl optionally substituted by lower alkyl optionally substituted by one or more halogens), (6) —C(O)-aryl, (7) —C(O)-lower alkenylene-aryl, (8) —NH—C(O)-lower alkyl, (9) aromatic heterocycle,

(10) nonaromatic heterocycle,

(11) —C(O)-lower alkyl,

(12) —S-lower alkyl and —S(O)$_2$-lower alkyl,

(13) -lower alkenylene-C(O)O-lower alkyl,

(14) cycloalkyl,

(15) —O-nonaromatic heterocycle, and

(16) —C(O)O-lower alkyl.

A yet another embodiment of an acceptable substituent of the "optionally substituted aryl" in the formula (I) includes (1) lower alkyl optionally substituted by one or more halogens, (2) halogen, and (3) aryl.

A yet another embodiment of an acceptable substituent of the "optionally substituted aromatic heterocycle" in the formula (I) includes (1) lower alkyl and —O-lower alkyl, wherein the lower alkyl moiety is optionally substituted by one or more substituents selected from the group consisting of halogen, —OH and —O-lower alkyl, (2) halogen, (3) aryl optionally substituted by one or more substituents selected from the group consisting of lower alkyl, halogen, —OH, —O-lower alkyl, —O-(lower alkyl substituted by one or more halogens) and lower alkyl substituted by one or more halogens, (4) nonaromatic heterocycle and —O-nonaromatic heterocycle, wherein the nonaromatic heterocycle moiety is optionally substituted by one or more substituents selected from the group consisting of lower alkyl and halogen, and (5) oxo.

A yet another embodiment of an acceptable substituent of the "optionally substituted aromatic heterocycle" in the formula (I) includes (1) lower alkyl optionally substituted by one or more halogens, (2) halogen, (3) —O-lower alkyl, (4) —O-nonaromatic heterocycle, and (5) aryl.

A yet another embodiment of an acceptable substituent of the "optionally substituted nonaromatic heterocycle" in the formula (I) includes (1) lower alkyl and -L$^{21}$-O-lower alkyl, wherein the lower alkyl moiety is optionally substituted by one or more substituents selected from the group consisting of halogen, —OH, —O-lower alkyl, cycloalkyl, aryl (the aryl is optionally substituted by one or more substituents selected from the group consisting of lower alkyl, halogen, lower alkyl substituted by one or more halogens and —O-lower alkyl), —O-aryl (the aryl moiety of —O-aryl is optionally substituted by one or more substituents selected from the group consisting of lower alkyl, halogen, lower alkyl substituted by one or more halogens and —O-lower alkyl), aromatic heterocycle (the aromatic heterocycle is optionally substituted by one or more lower alkyl), nonaromatic heterocycle (the nonaromatic heterocycle is is optionally substituted by oxo), —C(O)-aromatic heterocycle, —C(O)-nonaromatic heterocycle and —N(lower alkyl)$_2$, (2) halogen, (3) —OH, (4) cycloalkyl, —O-cycloalkyl, —NH-cycloalkyl and —C(O)-cycloalkyl, wherein the cycloalkyl moiety is optionally substituted by one or more lower alkyl, (5) -L$^{21}$-aryl, —O-aryl, —C(O)-aryl and —S(O)$_m$-aryl, wherein the aryl moiety is optionally substituted by one or more substituents selected from the group consisting of lower alkyl, halogen, —O-lower alkyl, —C(O)O-lower alkyl and —CN, (6) aromatic heterocycle, —O-aromatic heterocycle, —C(O)-aromatic heterocycle, —C(O)NH-aromatic heterocycle and —S(O)$_m$-aromatic heterocycle, wherein the aromatic heterocycle moiety is optionally substituted by one or more substituents selected from the group consisting of lower alkyl, aryl, halogen and —OH, (7) nonaromatic heterocycle, —O-nonaromatic heterocycle, —C(O)-nonaromatic heterocycle and —S(O)$_m$-nonaromatic heterocycle, wherein the nonaromatic heterocycle moiety is optionally substituted by one or more substituents selected from the group consisting of lower alkyl, halogen, —OH, —O-lower alkyl and oxo, (8) —C(O)O-lower alkyl, —OC(O)-lower alkyl, —S(O)$_2$-lower alkyl and —N(lower alkyl)$_2$, wherein the lower alkyl moiety is optionally substituted by one or more substituents selected from the group consisting of halogen and —OH, and (9) oxo.

A yet another embodiment of an acceptable substituent of the "optionally substituted nonaromatic heterocycle" in the formula (I) includes (1) lower alkyl, optionally substituted one or more substituents selected from the group consisting of aryl optionally substituted by one or more substituents selected from the group consisting of lower alkyl optionally substituted by one or more halogens, halogen and —O-lower alkyl, —O-aryl, aromatic heterocycle optionally substituted by one or more lower alkyl, nonaromatic heterocycle optionally substituted by oxo, —C(O)-nonaromatic heterocycle, cycloalkyl, —O-lower alkyl and —N(lower alkyl)$_2$, (2) —O-(lower alkyl optionally substituted by aryl optionally substituted by one or more halogens), (3) halogen, (4) —OH, (5) aryl optionally substituted by one or more substituents selected from the group consisting of —CN and —O-lower alkyl,
(6) —O-(aryl optionally substituted by one or more substituents selected from the group consisting of lower alkyl, halogen, —O-lower alkyl and —C(O)O-lower alkyl),
(7) —C(O)-(aryl optionally substituted by one or more substituents selected from the group consisting of —O-lower alkyl and halogen),
(8) —S(O)$_2$-(aryl optionally substituted by one or more substituents selected from the group consisting of lower alkyl and halogen),
(9) nonaromatic heterocycle optionally substituted by one or more substituents selected from the group consisting of lower alkyl, —OH and oxo,
(10) —O-nonaromatic heterocycle,
(11) —C(O)-nonaromatic heterocycle,
(12) —S(O)$_2$-nonaromatic heterocycle,
(13) aromatic heterocycle optionally substituted by one or more aryl,
(14) —O-(aromatic heterocycle optionally substituted by one or more substituents selected from the group consisting of lower alkyl and halogen),
(15) —C(O)-aromatic heterocycle,
(16) —S(O)$_2$-(aromatic heterocycle optionally substituted by one or more lower alkyl),
(17) —C(O)—NH-aromatic heterocycle,
(18) cycloalkyl,
(19) —C(O)-cycloalkyl,
(20) —NH-cycloalkyl,
(21) oxo,
(22) —S(O)$_2$-lower alkyl,
(23) —C(O)O-lower alkyl,
(24) —O—C(O)O-lower alkyl,
(25) —O—C(O)-lower alkyl, and
(26) —N(lower alkyl)$_2$.

A yet another embodiment of an acceptable substituent of the "optionally substituted nonaromatic heterocycle" in the formula (I) includes
(1) lower alkyl optionally substituted by one or more substituents selected from the group consisting of halogen and —O-lower alkyl, —S(O)$_2$-lower alkyl, —C(O)O-lower alkyl and —O—C(O)-lower alkyl,
(2) aryl optionally substituted by one or more —CNs, -lower alkylene-O-aryl, -lower alkylene-(aryl optionally substituted by one or more substituents selected from the group consisting of lower alkyl optionally substituted by one or more halogens, halogen and —O-lower alkyl), —C(O)-(aryl optionally substituted by one or more substituents selected from the group consisting of —O-lower alkyl and halogen), —O-(aryl optionally substituted by one or more substituents selected from the group consisting of lower alkyl, halogen, —O-lower alkyl and —C(O)—O-lower alkyl), —O-lower alkylene-(aryl optionally substituted by one or more halogens) and —S(O)$_2$-(aryl optionally substituted by one or more substituents selected from the group consisting of halogen and lower alkyl),
(3) nonaromatic heterocycle optionally substituted by one or more substituents selected from the group consisting of oxo, —OH and lower alkyl, —S(O)$_2$-nonaromatic heterocycle, —C(O)-nonaromatic heterocycle, -lower alkylene-C(O)-nonaromatic heterocycle and -lower alkylene-(nonaromatic heterocycle optionally substituted by one or more oxo),
(4) aromatic heterocycle optionally substituted by one or more aryl, —O-(aromatic heterocycle optionally substituted by one or more substituents selected from the group consisting of lower alkyl and halogen), —C(O)-aromatic heterocycle, —S(O)$_2$-(aromatic heterocycle optionally substituted by one or more lower alkyl), —C(O)—NH-aromatic heterocycle and -lower alkylene-(aromatic heterocycle optionally substituted by one or more lower alkyl),
(5) cycloalkyl, -lower alkylene-cycloalkyl, —C(O)-cycloalkyl and —NH-cycloalkyl,
(6) -lower alkylene-N(lower alkyl)$_2$,
(7) oxo, and
(8) —N(lower alkyl)$_2$.

Certain embodiments of the present invention are shown below.
(1) In one embodiment of X, Y and Z, Z is CH, in another embodiment, X is CH, Y is N and Z is CH and, in still another embodiment, X is N, Y is N and Z is CH.
(2) In one embodiment of $R^1$, $R^1$ is -$L^1$-$R^4$, in another embodiment, $R^1$ is $C_{1-10}$ alkyl, -lower alkylene-O$R^3$, halogen, optionally substituted cycloalkyl or -lower alkylene-(optionally substituted cycloalkyl), in another embodiment, $R^1$ is -$L^1$-(aryl optionally substituted by one or more substituents selected from the group consisting of lower alkyl, halogen, lower alkyl substituted by one or more halogens, —O-lower alkyl, —O-lower alkylene-OH, —O-(lower alkyl substituted by one or more halogens), —S(O)$_m$-lower alkyl, cycloalkyl, optionally substituted aryl, -lower alkylene-aryl, —O-aryl, aromatic heterocycle, nonaromatic heterocycle, —C(O)-lower alkyl, —C(O)-aryl, —C(O)-lower alkenylene-aryl, —NH—C(O)-lower alkyl and -lower alkenylene-C(O)O-lower alkyl), in still another embodiment, $R^1$ is -$L^1$-(aryl optionally substituted by one or more substituents selected from the group consisting of halogen, lower alkyl optionally substituted by one or more halogens, —O-(lower alkyl optionally substituted by one or more halogens) and aryl), in still another embodiment, $R^1$ is -$L^1$-(aryl optionally substituted by one or more substituents selected from the group consisting of lower alkyl optionally substituted by one or more halogens, halogen and aryl), in still another embodiment, $R^1$ is -$L^1$-optionally substituted cycloalkyl, in still another embodiment, $R^1$ is -lower alkylene-C(O)-(nonaromatic heterocycle optionally substituted by one or more substituents selected from the group consisting of lower alkyl, —N(lower alkyl)$_2$, -lower alkylene-phenyl, -lower alkylene-O-lower alkyl, -lower alkylene-O-phenyl and morpholinyl group), in still another embodiment, $R^1$ is -lower alkylene-(optionally substituted aromatic heterocycle), in still another embodiment, $R^1$ is -$L^2$-N(—$R^5$)$R^6$, in still another embodiment, $R^1$ is -lower alkylene-(phenyl optionally substituted by one or more substituents selected from the group consisting of lower alkyl, halogen, lower alkyl substituted by one or more halogens, —O-lower alkyl, —O-(lower alkyl substituted by one or more halogens) and optionally substituted aryl), in still another embodiment, $R^1$ is -lower alkylene-(phenyl optionally substituted by one or more substituents selected from the group consisting of lower alkyl optionally substituted by one or more halogens, halogen and aryl) and, in still another embodiment, $R^1$ is -lower alkylene-O-(phenyl optionally substituted by one or more substituents selected from the group consisting of lower alkyl, halogen, lower alkyl substituted by one or more halogens, —O-lower alkyl, —O-(lower alkyl substituted by one or more halogens), cycloalkyl, -$L^{21}$-phenyl, —O-optionally substituted aryl, —C(O)-lower alkyl, —C(O)-phenyl, —C(O)-lower alkenylene-aryl, -lower alkenylene-C(O)O-lower alkyl, —NH—C(O)-lower alkyl, —S(O)$_2$-lower alkyl, piperidyl group and quinolinyl group).
(3) In one embodiment of R$^2$, R$^2$ is H or lower alkyl and, in another embodiment, R$^2$ is H.
(4) In one embodiment of R$^3$, R$^3$ is lower alkyl and, in another embodiment, R$^3$ is H.
(5) In one embodiment of R$^4$, R$^4$ is optionally substituted cycloalkyl or optionally substituted aryl, in another embodiment, R$^4$ is cycloalkyl or aryl, each of which is optionally substituted by one or more substituents selected from the group consisting of group D1, in another embodiment, R$^4$ is aryl optionally substituted by one or more substituents selected from the group consisting of group D1, in still another embodiment, cycloalkyl optionally substituted by one or more substituents selected from the group consisting of group D1, in still another embodiment, R$^4$ is aryl optionally substituted by one or more substituents selected from the group consisting of halogen, lower alkyl optionally substituted by one or more halogens, —O-(lower alkyl optionally substituted by one or more halogens) and aryl and, in still another embodiment, R$^4$ is aryl optionally substituted by one or more substituents selected from the group consisting of lower alkyl optionally substituted by one or more halogens, halogen and aryl.
(6) In one embodiment of R$^5$, R$^5$ is H or lower alkyl, in another embodiment, R$^5$ is H and, in still another embodiment, R$^5$ is lower alkyl.
(7) In one embodiment of R$^6$, R$^6$ is -lower alkylene-N(R$^8$)$_2$, -lower alkylene-(aryl optionally substituted by one or more nonaromatic heterocycles), -lower alkylene-(nonaromatic heterocycle optionally substituted by one or more lower alkyl), -lower alkylene-aromatic heterocycle, in another embodiment, R$^6$ is -lower alkylene-N(R$^8$)$_2$, in still another embodiment, R$^6$ is -lower alkylene-(aryl optionally substituted by one or more nonaromatic heterocycles), in still another embodiment, R$^6$ is -lower alkylene-(nonaromatic heterocycle optionally substituted by one or more lower alkyl) and, in still another embodiment, R$^6$ is -lower alkylene-aromatic heterocycle.
(8) One embodiment of R$^7$ is H.
(9) In one embodiment of R$^8$, each R$^8$ is methyl.
(10) In one embodiment of L$^1$, L$^1$ is -lower alkylene-, -lower alkylene-O—, -lower alkylene-S— or -lower alkylene-C(O)—, in another embodiment, L$^1$ is -lower alkylene-, -lower alkylene-O— or -lower alkylene-S—, in still another embodiment, L$^1$ is -lower alkylene-, in still another embodiment, L$^1$ is -lower alkylene-O—, in still another embodiment, L$^1$ is methylene or ethylene and, in still another embodiment, L$^1$ is ethylene.
(11) In one embodiment of L$^2$, L$^2$ is -lower alkylene- or -lower alkylene-C(O)—, in another embodiment, L$^2$ is -lower alkylene-, in still another embodiment, L$^2$ is -lower alkylene-C(O)—, in still another embodiment, L$^2$ is methylene or ethylene and, in still another embodiment, L$^2$ is ethylene.
(12) In one embodiment of L$^{21}$, L$^{21}$ is -lower alkylene-.
(13) A compound which is a combination of two or more groups described in the above-mentioned (1)-(12) or a salt thereof.

As described in the above-mentioned (13), the present invention encompasses a compound which is a combination of two or more groups described in the above-mentioned (1)-(12) or a salt thereof. Concrete examples thereof also include the following embodiments.

(14) A compound wherein Z is CH, and R$^1$ is C$_{1-10}$ alkyl, -lower alkylene-OR$^3$, halogen, optionally substituted cycloalkyl or -lower alkylene-optionally substituted cycloalkyl, or a salt thereof.
(15) A compound wherein Z is CH, and R$^1$ is -L$^1$-(aryl optionally substituted by one or more substituents selected from the group consisting of lower alkyl, halogen, lower alkyl substituted by one or more halogens, —O-lower alkyl, —O-lower alkylene-OH, —O-(lower alkyl substituted by one or more halogens), —S(O)$_m$-lower alkyl, cycloalkyl, optionally substituted aryl, -lower alkylene-aryl, —O-aryl, aromatic heterocycle, nonaromatic heterocycle, —C(O)-lower alkyl, —C(O)-aryl, —C(O)-lower alkenylene-aryl, —NH—C(O)-lower alkyl and -lower alkenylene-C(O)O-lower alkyl), or a salt thereof.
(16) A compound wherein Z is CH, and R$^1$ is -lower alkylene-C(O)-(nonaromatic heterocycle optionally substituted by one or more substituents selected from the group consisting of lower alkyl, —N(lower alkyl)$_2$, -lower alkylene-phenyl, -lower alkylene-O-lower alkyl, -lower alkylene-O-phenyl and a morpholinyl group), or a salt thereof.
(17) A compound wherein Z is CH, and R$^1$ is -lower alkylene-(optionally substituted aromatic heterocycle), or a salt thereof.
(18) A compound wherein X is N, Y is N, Z is CH, R$^1$ is -L$^1$-R$^4$, L$^1$ is -lower alkylene-, -lower alkylene-O— or -lower alkylene-S—, and R$^4$ is optionally substituted cycloalkyl or optionally substituted aryl, or a salt thereof.
(19) The compound of (18), wherein R$^4$ is aryl optionally substituted by one or more substituents selected from the group consisting of halogen, lower alkyl optionally substituted by one or more halogens, —O-(lower alkyl optionally substituted by one or more halogens) and aryl, or a salt thereof.
(20) The compound of (19), wherein R$^4$ is aryl optionally substituted by one or more substituents selected from the group consisting of lower alkyl optionally substituted by one or more halogens, halogen and aryl, or a salt thereof.
(21) The compound of (20), wherein L$^1$ is -lower alkylene, or a salt thereof.
(22) A compound wherein Z is CH, and R$^1$ is L$^2$-N(—R$^5$)R$^6$, or a salt thereof.
(23) The compound of (14), wherein R$^3$ is lower alkyl, or a salt thereof.
(24) The compound of (22), wherein R$^5$ is H or lower alkyl, or a salt thereof.
(25) The compound of (22) or (24), wherein R$^6$ is -lower alkylene-N(R$^8$)$_2$, -lower alkylene-(aryl optionally substituted by one or more nonaromatic heterocycles), -lower alkylene-(nonaromatic heterocycle optionally substituted by one or more lower alkyl) or -lower alkylene-aromatic heterocycle, or a salt thereof.
(26) The compound of (25), wherein each R$^8$ is methyl, or a salt thereof.
(27) The compound of (15), wherein L$^1$ is -lower alkylene-, -lower alkylene-O—, -lower alkylene-S— or -lower alkylene-C(O)—, or a salt thereof.
(28) The compound of (22), wherein L$^2$ is -lower alkylene- or -lower alkylene-C(O)—, or a salt thereof.

Specific examples of the compound encompassed in the compound of the formula (I) or a salt thereof include the following.

4-hydroxy-6-{2-[4-(trifluoromethyl)phenyl]ethyl}pyridazin-3(2H)-one,
4-hydroxy-6-[2-(4-methylphenyl)ethyl]pyridazin-3(2H)-one,
6-[2-(biphenyl-4-yl)ethyl]-4-hydroxypyridazin-3(2H)-one,
4-hydroxy-6-{2-[3-(trifluoromethyl)phenyl]ethyl}pyridazin-3(2H)-one,
6-[2-(3-fluorophenyl)ethyl]-4-hydroxypyridazin-3(2H)-one,
4-hydroxy-6-[2-(3-methylphenyl)ethyl]pyridazin-3(2H)-one,
6-[2-(2,4-difluorophenyl)ethyl]-4-hydroxypyridazin-3(2H)-one,
4-hydroxy-6-[2-(2-methylphenyl)ethyl]pyridazin-3(2H)-one,
6-[2-(3,5-difluorophenyl)ethyl]-4-hydroxypyridazin-3(2H)-one,
6-(2-cyclohexylethyl)-4-hydroxypyridazin-3(2H)-one, and
4-hydroxy-6-[2-(1-naphthyl)ethyl]pyridazin-3(2H)-one,
or a salt thereof.

The compound of the formula (I) may contain tautomer and geometric isomer depending on the kind of the substituent. In the present specification, the compound of the formula (I) may be described only one form of isomer. However, the present invention encompasses other isomers and also encompasses separated isomers and a mixture thereof.

Moreover, the compound of the formula (I) may have asymmetric carbon atom and axial chirality, and optical isomers may be present based thereon. The present invention also encompasses separated optical isomers of the compound of the formula (I) and a mixture thereof.

Moreover, the compound of the formula (I) may have a plurality of resonance structures. While the present invention describes one of them, the resonance structure is not limited thereto. The resonance structural formulas (Ex. 1-1-Ex. 1-3) of Example 1 (Ex. 1) are shown below as examples. Ex. shows the Example No. mentioned later.

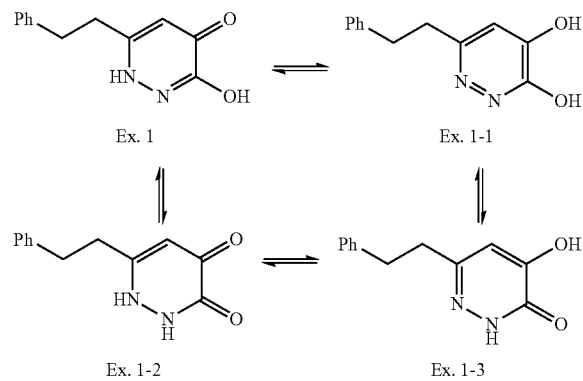 [SMILES: O=c1cc(CCc2ccccc2)[nH]nc1O ; Oc1cc(CCc2ccccc2)nnc1O ; O=c1cc(CCc2ccccc2)[nH][nH]c1=O ; O=c1[nH]nc(CCc2ccccc2)cc1O]

Furthermore, the present invention includes pharmacologically acceptable prodrugs of the compound represented by the formula (I). The pharmacologically acceptable prodrug is a compound having a group convertible to an amino group, a hydroxy group, a carboxyl group and the like by solvolysis or under physiological conditions. Examples of the group forming a prodrug include the groups described in Prog. Med., 5, 2157-2161 (1985) and "Development of Pharmaceutical Product" (Hirokawa Shoten, 1990) Vol. 7, Molecule Design, pp. 163-198.

A salt of the compound of the formula (I) is a pharmaceutically acceptable salt of the compound of the formula (I), which may form an acid addition salt or a salt with a base depending on the kind of the substituent. Specific examples thereof include acid addition salts with inorganic acids such as hydrochloric acid, hydrobromic acid, hydroiodic acid, sulfuric acid, nitric acid, phosphoric acid and the like, and organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, glutamic acid and the like; salts with inorganic bases such as sodium, potassium, magnesium, calcium, aluminum and the like, and organic bases such as methylamine, ethylamine, ethanolamine, lysine, ornithine and the like; salts with various amino acids such as acetylleucine and the like, and amino acid derivative; ammonium salt and the like.

Furthermore, the present invention also encompasses various hydrates and solvates, and substances having crystal polymorphism of the compound of the formula (I) or a salt thereof. In addition, the present invention also encompasses compounds labeled with various radioactive or non-radioactive isotopes.

(Production Method)

The compound of the formula (I) and a salt thereof can be produced by applying various known synthesis methods, while utilizing characteristics based on the basic structure and the kind of the substituents thereof. In such procedures, it is sometimes technically effective, depending on the kind of functional group, to replace the functional group with a suitable protecting group (a group readily convertible to the functional group) during a step of converting the starting material into an intermediate. Examples of such protecting group include the protecting groups described in P. G. M. Wuts and T. W. Greene, "Greene's Protective Groups in Organic Synthesis" (4th Ed. 2006) and the like, and it may be selected as appropriate according to the reaction conditions thereof. In such processes, a desired compound can be obtained by performing a reaction after introducing the protecting group, and thereafter eliminating the protecting group as necessary.

A prodrug of the compound of the formula (I) can be produced by, in the same manner as in the above-mentioned protecting groups, introduction of a particular group during the stage of from a starting material to an intermediate, or further reaction of the obtained compound of the formula (I). The reaction can be performed by applying a method known to those of ordinary skill in the art such as conventional esterification, amidation, dehydration and the like.

The representative production methods of the compound of the formula (I) are explained below. Each production method can also be performed by reference to reference documents attached to the explanation. The production method of each invention is not limited to the examples shown below.

(First Production Method)

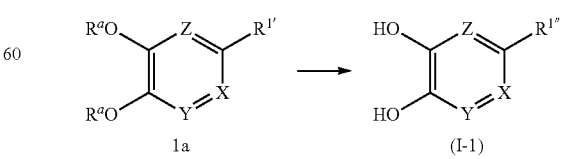

wherein $R^a$ are the same or different and each is H, a protecting group such as a benzyl group, a paramethoxybenzyl group, a methoxymethyl group, a methyl group and the like, $R^1$ is $C_{1-10}$ alkyl, -lower alkynylene-$OR^3$, optionally substituted cycloalkenyl, -lower alkenylene-$R^4$, -lower alkenylene-C(O)—$R^4$, -lower alkenylene-N(—$R^5$)$R^6$ or -lower alkenylene-C(O)—N(—$R^5$)$R^6$, $R^{1''}$ is $C_{1-10}$ alkyl, -lower alkylene-$OR^3$, optionally substituted cycloalkyl, -lower alkylene-$R^4$, -lower alkenylene-$R^4$, -lower alkylene-C(O)—$R^4$, -lower alkylene-N(—$R^5$)$R^6$ or -lower alkylene-C(O)—N(—$R^5$)$R^6$, provided both $R^a$ are not H at the same time.

In this production method, compound 1a is deprotected to produce compound (I-1) of the present invention, which is the compound (I) of the present invention, wherein $R^1$ is $C_{1-10}$alkyl, -lower alkylene-$OR^3$, optionally substituted cycloalkyl, -lower alkylene-$R^4$, -lower alkenylene-$R^4$, -lower alkylene-C(O)—$R^4$, -lower alkylene-N(—$R^5$)$R^6$ or -lower alkylene-C(O)—N(—$R^5$)$R^6$.

In this step, for example, when $R^a$ is a benzyl group or a paramethoxybenzyl group, compound 1a and a metal catalyst are used in equivalent amounts or one of them in an excess amount, and the mixture thereof is stirred under a hydrogen atmosphere in a solvent inert to the reaction generally for 1 hr-5 days. This reaction is generally performed from under cooling to under heating, preferably at room temperature. While the solvent used here is not particularly limited, examples thereof include alcohols such as methanol, ethanol, 2-propanol and the like, ethers such as diethyl ether, tetrahydrofuran, dioxane, dimethoxyethane and the like, water, ethyl acetate, N,N-dimethylformamide, dimethyl sulfoxide and a mixture thereof. As the metal catalyst, palladium catalysts such as palladium carbon, palladium black, palladium hydroxide, palladium-barium sulfate and the like, platinum catalysts such as platinum plate, platinum oxide and the like, nickel catalysts such as reduced nickel, Raney-nickel and the like, rhodium catalysts such as tristriphenylphosphinechlororhodium and the like, iron catalysts such as reduced iron, etc. and the like are preferably used. Instead of hydrogen gas, formic acid or ammonium formate in an equivalent amount—excess amount relative to compound 1a can also be used as a hydrogen source.

When $R^{1'}$ of compound 1a is -lower alkynylene-$OR^3$, optionally substituted cycloalkenyl, -lower alkenylene-$R^4$, -lower alkenylene-C(O)—$R^4$, -lower alkenylene-N(—$R^5$)$R^6$ or -lower alkenylene-C(O)—N(—$R^5$)$R^6$, the alkynylene moiety, alkenylene moiety, and unsaturated moiety of cycloalkenyl can be reduced simultaneously with the above-mentioned deprotection.

Besides the above-mentioned method, under acidic conditions, compound 1a and thioanisole are used in equivalent amounts or one of them in an excess amount, and compound 1a can be deprotected in a solvent inert to the reaction, from under cooling to under heating, preferably at room temperature. While the solvent used here is not particularly limited, it can be performed using halogenated hydrocarbons such as dichloromethane, chloroform, etc. and the like, or without solvent. In addition, acidic conditions can be produced with trifluoroacetic acid and the like.

In addition, compound 1a and boron tribromide are used in equivalent amounts or one of them in an excess amount, and compound 1a can be deprotected in a solvent inert to the reaction, from under cooling to under heating, preferably at room temperature. While the solvent used here is not particularly limited, examples thereof include halogenated hydrocarbons such as dichloromethane, chloroform, etc. and the like.

[documents]

M. Hudlicky, "Reductions in Organic Chemistry, 2nd ed (ACS Monograph: 188)", ACS, 1996

The Chemical Society of Japan ed. "Jikken Kagaku Kouza (5th Ed.)" vol. 19 (2005) (Maruzen)

(Second Production Method)

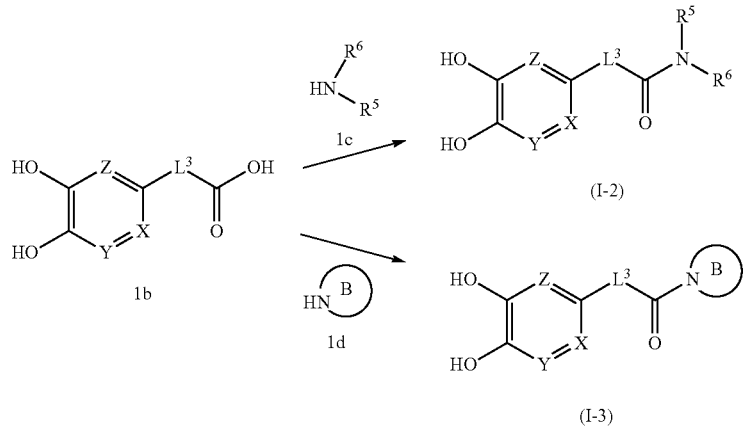

wherein B is an optionally substituted cyclic amino group.

In this production method, the compound (I-2) or (I-3) of the present invention, which is the compound (I) of the present invention wherein $R^1$ is -lower alkylene-C(O)—N(—$R^5$)$R^6$ or -lower alkylene-C(O)-(optionally substituted cyclic amino) is produced.

In this step, the compound (I-2) or (I-3) of the present invention is obtained by amidation of compound 1b and compound 1c or 1d.

In this step, compound 1b and compound 1c or 1d are used in equivalent amounts or one of them in an excess amount, and the mixture thereof is stirred in the presence of a condensing agent in a solvent inert to the reaction, from under cooling to under heating preferably at −20° C. to 60° C. generally for 0.1 hr to 7 days. While the solvent used here is not particularly limited, examples thereof include aromatic hydrocarbons such as benzene, toluene, xylene and the like, halogenated hydrocarbons such as dichloromethane, 1,2-dichloroethane, chloroform and the like, ethers such as diethyl ether, tetrahydrofuran, dioxane, dimethoxyethane and the like, N,N-dimethylformamide, dimethyl sulfoxide, ethyl acetate, acetonitrile, water, and a mixture thereof. Examples of the condensing agent include, but are not limited to, 1-(3-dimethylaminopropyl)-3-ethylcarbodiimide, dicyclohexylcarbodiimide, 1,1'-carbonyldiimidazole, diphenylphosphoryl azide, phosphorus oxychloride, polystyrene resin carrying a condensing agent (e.g., PS-carbodiimide). It is sometimes preferable to use an additive (for example, 1-hydroxybenzotriazole) for the reaction. It is sometimes advantageous to perform the reaction in the presence of an organic base such as triethylamine, N,N-diisopropylethylamine, N-methylmorpholine and the like, or an inorganic base such as potassium carbonate, sodium carbonate, potassium hydroxide and the like to smoothly carry out the reaction.

It is also possible to use a method involving converting the carboxyl group moiety of compound 1b to a reactive derivative and then reacting same with compound 1c or 1d. Examples of the reactive derivative of carboxylic acid include acid halides obtained by a reaction with a halogenating agent such as phosphorus oxychloride, thionyl chloride and the like, mixed acid anhydrides obtained by a reaction with isobutyl chloroformate and the like, active esters obtained by a condensation reaction with 1-hydroxybenzotriazole, etc. and the like. These reactive derivatives can be reacted with compound 1c or 1d in a solvent inert to the reaction such as halogenated hydrocarbons, aromatic hydrocarbons, ethers and the like, from under cooling to under heating, preferably at -20° C. to 60° C.

[documents]
S. R. Sandler and W. Karo, "Organic Functional Group Preparations", 2nd edition, vol. 1, Academic Press Inc., 1991

The Chemical Society of Japan ed. "Jikken Kagaku Kouza (5th ed.)" vol. 16 (2005) (Maruzen)

(Third Production Method)

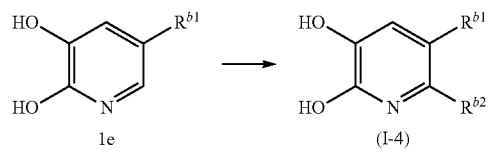

wherein $R^{b1}$ is a chloro group or a bromo group, and $R^{b2}$ is halogen, provided when $R^{b2}$ is a chloro group, $R^{b1}$ is a bromo group.

In this production method, the compound (I-4) of the present invention, which is the compound (I) of the present invention wherein X is C-halogen, Y is N, Z is CH and $R^1$ is a chloro group or a bromo group, is produced.

In this step, the compound (I-4) of the present invention is obtained by halogenation of compound 1e.

In this step, compound 1e and a halogenating agent are used in equivalent amounts or one of them in an excess amount, and the mixture thereof is stirred in a solvent inert to the reaction, from room temperature to under heating, preferably at room temperature generally for 0.1 hr to 5 days. The halogenating agent may be any as long as it is a halogenating agent generally used for halogen substitution reaction of hydrogen on the aromatic ring, and halogen elements such as chlorine, bromine and the like, perbromides such as dioxane dibromide, phenyltrimethylammonium tribromide, pyridinium hydrobromide perbromide, pyrrolidone hydrotribromide, etc. and the like are preferably used. It is also possible to use imide halogenating agents such as N-bromosuccinimide, N-chlorosuccinimide and the like, halogenated hydrogens such as hydrogen chloride, hydrogen bromide and the like, a metal reagent, for example, copper (II) halides such as copper (II) bromide, copper (II) chloride and the like and the like.

When a halogen element or perbromide is used as a halogenating agent, compound 1e may be reacted with a halogenating agent in an organic solvent inert to the reaction, for example, halogenated hydrocarbons, ethers, alcohols such as methanol, ethanol, 2-propanol, ethylene glycol and the like, aromatic hydrocarbons, esters such as ethyl acetate and the like, acetic acid, N,N-dimethylformamide and the like. Where necessary, the reaction may be performed in the presence of a small amount of a catalyst such as halogenated hydrogen and the like, at a preferable reaction temperature of −30° C. to the refluxing temperature of the solvent to be used.

When halogenated hydrogen is used as a halogenating agent, the compound (1e) may be reacted with halogenated hydrogen in an acidic solution thereof or a basic solution such as aqueous sodium hydroxide solution and the like, at a preferable reaction temperature of −30° C. to the refluxing temperature of the solvent to be used.

In addition, a reaction using a metal reagent is advantageously performed generally by dissolving compound 1e in an organic solvent inert to the reaction such as halogenated hydrocarbons, ethers, alcohols, aromatic hydrocarbons, acetic acid, esters and the like, water or a mixed solvent thereof and reacting same with a reagent and, where necessary, in the presence of a small amount of a catalyst such as halogenated hydrogen and the like at room temperature—under heating.

(Fourth Production Method)

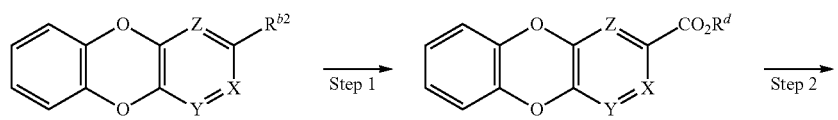

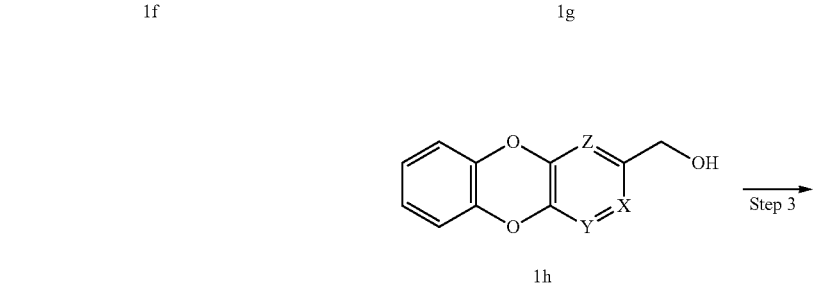

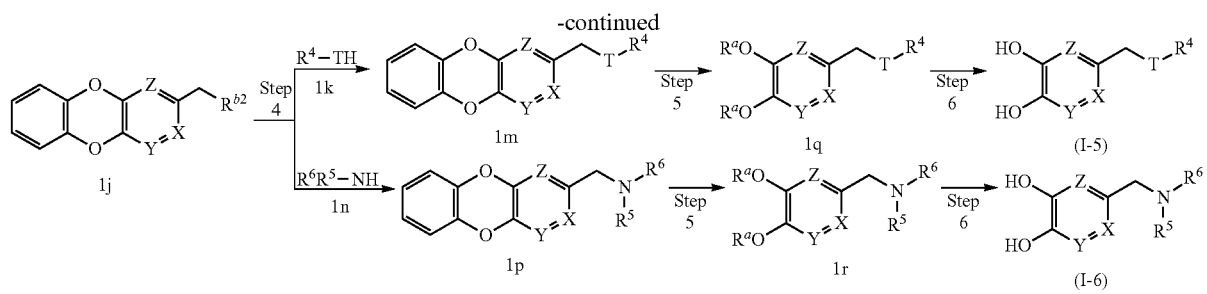

wherein T is —O— or —S—, and $R^d$ is lower alkyl.

In this production method, the compound (I-5) or (I-6) of the present invention, which is the compound (I) of the present invention wherein $R^1$ is —$CH_2$—O—$R^4$, —$CH_2$—S—$R^4$, —$CH_2$—N(—$R^5$)$R^6$, is produced.

(First Step)

In this step, carbon monoxide is inserted into the $R^b$ moiety of compound 1f, and then compound 1g in an ester form is synthesized by reacting with lower alcohol in the system.

In this step, a mixture of compound 1f, an equivalent or excess amount of carbon monoxide and a given lower alcohol is stirred in a solvent inert to the reaction, at normal pressure or under pressurization, preferably normal pressure, in the presence of a base and a palladium catalyst, at room temperature or with heating under reflux generally for 0.1 hr to 5 days. Examples of the given lower alcohol include methanol, ethanol, 2-propanol, butanol and the like. While the solvent used here is not particularly limited, examples thereof include aromatic hydrocarbons such as benzene, toluene, xylene and the like, ethers such as diethyl ether, tetrahydrofuran, dioxane, dimethoxyethane and the like, halogenated hydrocarbons such as dichloromethane, 1,2-dichloroethane, chloroform and the like, N,N-dimethylformamide, dimethyl sulfoxide, and a mixed solvent thereof. As the base, organic bases such as triethylamine and the like are preferable. As the palladium catalyst, diacetoxypalladium, tetrakis(triphenylphosphine)palladium, dichlorobis(triphenylphosphine)palladium, palladium chloride-1,1'-bis(diphenylphosphino)ferrocene and the like are preferable.

[Documents]

A. d. Meijere and F. Diederich ed., "Metal-Catalyzed Cross-Coupling Reactions", first ed., VCH Publishers Inc., 1997

The Chemical Society of Japan ed. "Jikken Kagaku Kouza (5th ed.)" vol. 13 (2005) (Maruzen)

(Second Step)

In this step, the ester moiety of compound 1g is reduced to produce compound 1h.

In this step, compound 1g and a given reducing agent are used in equivalent amounts or one of them in an excess amount, and the mixture thereof is stirred in a solvent inert to the reaction, from under cooling to under heating, preferably from −20° C. to 80° C. generally for 0.1 hr-5 days. While the solvent used here is not particularly limited, examples thereof include ethers such as diethyl ether, tetrahydrofuran, dioxane, dimethoxyethane and the like, alcohols such as methanol, ethanol, 2-propanol and the like, aromatic hydrocarbons such as benzene, toluene, xylene and the like, N,N-dimethylformamide, dimethyl sulfoxide, ethyl acetate and a mixture thereof. As the reducing agent, a hydride reducing agent such as sodium borohydride, diisobutylaluminum hydride and the like, a metal reducing agent such as sodium, zinc, iron and the like, and a reducing agent in the following document are preferably used.

[Documents]

M. Hudlicky, "Reductions in Organic Chemistry, 2nd ed (ACS Monograph: 188)", ACS, 1996

R. C. Larock, "Comprehensive Organic Transformations", 2nd edition, VCH Publishers, Inc., 1999

T. J. Donohoe, "Oxidation and Reduction in Organic Synthesis (Oxford Chemistry Primers 6)", Oxford Science Publications, 2000

The Chemical Society of Japan ed. "Jikken Kagaku Kouza (5th ed.)" vol. 14 (2005) (Maruzen)

(Third Step)

In this step, the hydroxyl group moiety of compound 1h is halogenated to produce compound 1j.

In this step, compound 1h and a given halogenating agent are used in equivalent amounts or one of them in an excess amount, and the mixture thereof is stirred in a solvent inert to the reaction, from under cooling to under heated reflux, preferably from −30° C. to under heated reflux generally for 0.1 hr-5 days. The given halogenating agent may be any as long as it is a halogenating agent generally used for a halogen substitution reaction of the hydroxyl group, and thionyl chloride, thionyl bromide, phosphorus oxychloride and the like are preferably used. While the solvent used here is not particularly limited, halogenated hydrocarbons such as dichloromethane, chloroform, etc. and the like can be mentioned. When a halogen element or perbromide is used as a halogenating agent, an organic solvent inert to the reaction such as halogenated hydrocarbons, ethers, aromatic hydrocarbons, esters such as ethyl acetate and the like, acetic acid and the like are preferably used.

(Fourth Step)

In this step, compound 1j is etherified to produce compound 1m or compound 1p.

In this step, compound 1j and compound 1k or compound 1n are used in equivalent amounts or one of them in an excess amount, and the mixture thereof is stirred in a solvent inert to the reaction or without a solvent, from under cooling to under heated reflux, preferably 0° C.-80° C. generally for 0.1 hr-5 days. While the solvent used here is not particularly limited, examples thereof include aromatic hydrocarbons such as benzene, toluene, xylene and the like, ethers such as diethyl ether, tetrahydrofuran, dioxane, dimethoxyethane and the like, halogenated hydrocarbons such as dichloromethane, 1,2-dichloroethane, chloroform and the like, N,N-dimethylformamide, dimethyl sulfoxide, ethyl acetate, acetonitrile and a mixture thereof. It is sometimes advantageous to perform the reaction in the presence of an organic base such as triethylamine, N,N-diisopropylethylamine, N-methylmorpholine and the like or an inorganic base such as potassium carbonate, sodium carbonate, potassium hydroxide and the like to smoothly carry out the reaction.

[Documents]

S. R. Sandler and W. Karo, "Organic Functional Group Preparations", 2nd edition, vol. 1, Academic Press Inc., 1991

The Chemical Society of Japan ed. "Jikken Kagaku Kouza (5th ed.)" vol. 14 (2005) (Maruzen)

(Fifth Step)

In this step, the catechol moiety of compound 1m or compound 1p is substituted by a benzyloxy group or a paramethoxybenzyloxy group and the like to give the compound Iq or Ir of the present invention.

In this step, compound 1m or 1p and benzylalcohol or paramethoxybenzylalcohol are used in equivalent amounts or one of them in an excess amount, and the mixture thereof is stirred in the presence of a given base, for example, t-butoxy potassium and the like, in a solvent inert to the reaction, from under cooling to under heating generally for 0.1 hr-5 days. While the solvent used here is not particularly limited, examples thereof include halogenated hydrocarbons, ethers, aromatic hydrocarbons, N,N-dimethylformamide and a mixture thereof.

(Sixth Step)

In this step, compound 1q or 1r is deprotected to produce the compound (I-5) or (I-6) of the present invention.

In this step, the First production method can be used.

(Starting Material Synthesis 1)

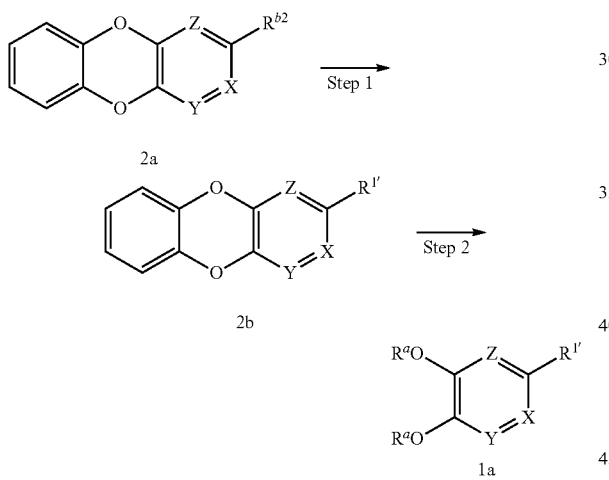

In this production method, the starting material compound 1a of First production method is produced.

(First Step)

In this step, compound 2b is produced by the Suzuki coupling reaction or Sonogashira coupling reaction from compound 2a produced by the method described in Journal of the Chemical Society. Perkin Transaction 1, 1975, (6), 534-538 or a method analogous thereto.

In this step, compound 2a and a given organic boron compound or terminus alkyne derivative are used in equivalent amounts or one of them in an excess amount, and the mixture thereof is stirred in a solvent inert to the reaction in the presence of a base and palladium catalyst, from room temperature to under heated reflux generally for 0.1 hr-5 days. This reaction is preferably performed under an inert gas atmosphere. While the solvent used here is not particularly limited, examples thereof include aromatic hydrocarbons such as benzene, toluene, xylene and the like, ethers such as diethyl ether, tetrahydrofuran, dioxane, dimethoxyethane and the like, halogenated hydrocarbons such as dichloromethane, 1,2-dichloroethane, chloroform and the like, alcohols such as methanol, ethanol, 2-propanol, butanol and the like, N,N-dimethylformamide, dimethyl sulfoxide and a mixed solvent thereof. As the base, an inorganic base such as sodium carbonate, potassium carbonate, cesium carbonate, sodium hydroxide and the like is preferable. As the palladium catalyst, tetrakis(triphenylphosphine)palladium, dichlorobis(triphenylphosphine)palladium, palladium chloride-1,1'-bis(diphenylphosphino)ferrocene and the like are preferable.

The Sonogashira coupling reaction is preferably performed in the presence of copper iodide and the like.

[Documents]

A. d. Meijere and F. Diederich ed., "Metal-Catalyzed Cross-Coupling Reactions", first ed., VCH Publishers Inc., 1997

The Chemical Society of Japan ed. "Jikken Kagaku Kouza (5th ed.)" vol. 13 (2005) (Maruzen)

(Second Step)

In this step, the catechol moiety of compound 2b is substituted by a benzyloxy group or paramethoxybenzyloxy group and the like.

In this step, the method of Fourth production method, Fifth step can be used.

(Starting Material Synthesis 2)

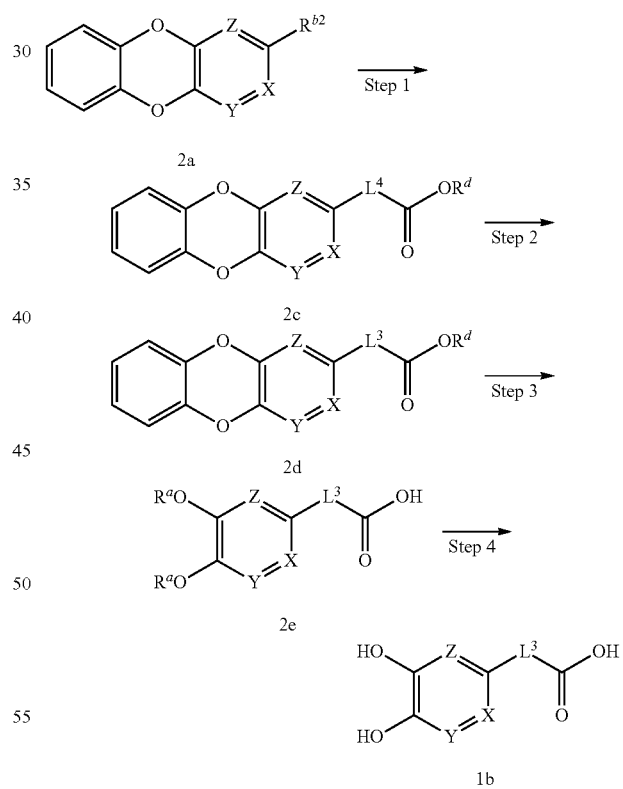

wherein $L^4$ is lower alkenylene.

In this production method, the starting material compound 1b of the Second production method is produced.

(First Step)

In this step, compound 2c is produced by the Suzuki coupling reaction of compound 2a produced by the method described in Journal of the Chemical Society. Perkin Transaction 1, 1975, (6), 534-538 or a method analogous thereto.

In this step, the method of Starting material synthesis 1, First step, can be used.
(Second Step)
In this step, the lower alkenylene moiety of compound 2c is reduced to produce compound 2d.
In this step, the method of First production method can be used.
(Third Step)
In this step, the catechol moiety of compound 2d is substituted by a benzyloxy group or a paramethoxybenzyloxy group and the like to produce compound 2e.
In this step, the method of Fourth production method, Fifth step can be used. By this step, the ester moiety can be simultaneously hydrolyzed.
(Fourth Step)
In this step, compound 2e is deprotected to produce compound 1b.
In this step, the method of First production method can be used.

The compound of the formula (I) is isolated as a free compound, a salt, hydrate, solvate, or substance having crystal polymorphism thereof and purified. A salt of the compound of the formula (I) can also be produced by applying a salt formation reaction which is a conventional method.

The isolation and purification is performed by applying a general chemical operation such as extraction, partition crystallization, various fraction chromatographys and the like.

Various isomers can be produced by selecting a suitable starting material compound, or separated by utilizing difference in physicochemical properties between isomers. For example, optical isomer is obtained by a general optical resolution method for racemate (e.g., partition crystallization to lead to a diastereomer salt with optically active base or acid, chromatography using chiral column and the like etc.), and can also be produced from a suitable optically active starting material compound.

The pharmacological activity of the compound of the formula (I) was confirmed by the following tests.

Experimental Example 1

DAAO Inhibitory Activity Test

The DAAO inhibitory activity was measured by assaying the amount of hydrogen peroxide ($H_2O_2$) produced by reacting DAAO protein with flavin adenine dinucleotide (FAD) and D-alanine. The amount of $H_2O_2$ was determined by measuring the fluorescence generated on conversion of Amplex red (manufactured by Invitrogen Co.) into resorufin by the reaction of $H_2O_2$ with horseradish peroxidase (HRP). 4 µL of 4% dimethyl sulfoxide (DMSO) buffer (50 mM sodium phosphate (pH 7.5), 0.02% CHAPS) solution of the test compound was added to 384-well black, low volume plate, a mixed solution (4 µL) of recombinant human DAAO protein (15 nM), which had been expressed in *Escherichia coli* and purified, and 18 µM FAD was added, and the mixture was incubated at room temperature for 15 min. After incubation, a mixed buffer (4 µL) of 2.25 mM D-alanine, 1.5 U/mL HRP and 150 µM Amplex red was added, the mixture was incubated at room temperature for 30 min, and the fluorescence (excitation wavelength 530 nm, fluorescence wavelength 590 nm) was measured using an Envision plate reader (manufactured by Perkin Elmer Co.). To cross-check the artificial inhibition of Amplex red conversion or the HRP activity inhibition of the test compound, the fluorescence was also measured under the conditions of 30 µM $H_2O_2$ addition in the absence of DAAO. Taking the fluorescence value in the absence of the test compound as 100% and the fluorescence value in the absence of DAAO as 0%, the DAAO activity was regarded to have been inhibited when the fluorescence value decreased by 50% in the presence of the test compound, and the concentration of the test compound at that time was taken as the $IC_{50}$ value (nM).

The recombinant human DAAO protein used in the above-mentioned Experimental Example 1 was produced by the following method by reference to Protein Science, 2006, 15, 12, 2708-2717.

1. Cloning and Expression of Human D-amino Acid Oxidase (DAAO)

A cDNA encoding human DAAO having sequence 154-1197 of the DAAO sequence (NM_001917.4) registered at NCBI was cloned by PCR from human cDNA library (manufactured by Clonetech) and inserted into the pET-42b vector (manufactured by Novagen) using NdeI and XhoI restriction enzyme sites. *Escherichia coli* strain BL21(DE3) (manufactured by Novagen) was transformed with the constructed human DAAO expression vector, inoculated into LB culture medium containing kanamycin at a final concentration of 20 µg/mL, and shake-cultured at 37° C. overnight. The multiplied transformant was inoculated into Terrific Broth containing kanamycin at a final concentration of 20 µg/mL, and shake-cultured at 37° C. until it reached $OD_{600}$=3.0. Thereafter, the culture was cooled to 30° C., and expression was induced with 1 mM IPTG. After 20 hours, bacterial pellets were recovered by centrifugation.

2. Purification of Human D-amino Acid Oxidase (DAAO)

The bacterial pellets recovered as above were suspended in a lysis buffer (17 mM sodium pyrophosphate buffer pH 8.3, 100 µM FAD, 1 mM sodium benzoate, 1 mM PMSF, 14 mM β-mercaptoethanol, 0.2 mg/mL lysozyme) and the bacteria were fractured by sonication. The sonicated liquid was centrifuged and the supernatant was recovered. To remove the nucleic acid, to this supernatant were sequentially added NaCl (final concentration 0.5M) and 0.05% ethyleneimine (polymer) and, after thorough mixing, the supernatant was recovered by centrifugation. The supernatant was heat treated at 55° C. for 15 min, and the supernatant was recovered by centrifugation. To this supernatant was added 40% saturated ammonium sulfate and, after thorough mixing, the salt precipitate was recovered by centrifugation. The obtained salt precipitate was redissolved in buffer A (50 mM potassium phosphate buffer pH 7.4, 10% glycerol, 200 µM sodium benzoate, 10 µM FAD, 20% saturated ammonium sulfate), and filtered through a 0.22 µm filter (manufactured by Millipore). The obtained filtrate was applied to a hydrophobic interaction column Butyl-S Sepharose 6 Fast Flow (manufactured by GE Healthcare Life Sciences) and eluted with buffer B (10 mM Tris buffer solution pH 8.0, 200 µM sodium benzoate, 10% glycerol, 10 µM FAD). The eluent was applied to an anion-exchange column, Q Sepharose Fast Flow (manufactured by GE Healthcare Life Sciences) and eluted using an NaCl concentration gradient. The eluate was replaced with buffer B (sic) using Amicon Ultra-15 10 kDa (manufactured by Millipore), and thereafter applied to an anion-exchange column, RESOURCE Q 6 mL (manufactured by GE Healthcare Life Sciences), and eluted with an NaCl concentration gradient. The eluate was concentrated using Amicon Ultra-15 10 kDa, thereafter applied to a HiLoad 26/600 Superdex 200pg (manufactured by GE Healthcare Life Sciences) gel filtration column equilibrated with buffer C (10 mM potassium phosphate buffer pH 7.4, 0.5M NaCl, 400 µM sodium benzoate, 20 μM FAD), and the DAAO protein dimer fraction was recovered. The recovered DAAO protein was replaced (sic) with buffer D (10 mM trisodium citrate, 20 μM FAD, 400 μM sodium benzoate) using Amicon Ultra-15 10 kDa, concentrated to 10 mg/mL and cryopreserved at −80° C.

The results of some representative compounds are shown in Table 1. Ex. in the Table shows the Example No. mentioned later.

TABLE 1

| Ex | IC$_{50}$ (nM) |
|---|---|
| 1 | 3.8 |
| 4 | 3.5 |
| 9 | 3.9 |
| 12 | 12 |
| 13 | 6.1 |
| 14 | 2.9 |
| 15 | 1.2 |
| 16 | 2.1 |
| 17 | 2.4 |
| 18 | 1.4 |
| 19 | 63 |
| 20 | 2.5 |
| 21 | 2.2 |
| 22 | 3.3 |
| 23 | 13 |
| 24 | 1.5 |
| 25 | 6.6 |
| 26 | 8.1 |
| 27 | 2.0 |
| 28 | 8.1 |
| 29 | 6.9 |
| 30 | 8.4 |
| 40 | 4.7 |
| 47 | 5.2 |
| 48 | 4.9 |
| 52 | 2.5 |
| 53 | 13 |
| 56 | 2.3 |
| 58 | 44 |
| 212 | 3.1 |
| 231 | 2.9 |
| 232 | 2.3 |
| 237 | 2.2 |
| 254 | 2.7 |

Some representative compounds showed good DAAO inhibitory activity.

Experimental Example 2

Inhibitory Activity Test at Cellular Level Using DAAO-expressing Cells

This test was performed by partially modifying the method of Philip et. al. (J. Biomol. Screen. Vol. 11, pp 481-487, 2006). HEK293 cells that stably express human DAAO were suspended in Cellbanker solution at 5×10$^6$ cells/ml and cryopreserved at −80° C. At the time of measurement, the cells were centrifuged at 1000 rpm for one min and the Cellbanker solution was removed. The cells were resuspended at 5×10$^6$ cells/ml in FAD-containing buffer (50 mM sodium phosphate [pH 7.5], 18 μM FAD, 0.02% CHAPS). A 4% DMSO buffer solution (50 mM sodium phosphate [pH 7.5], 0.02% CHAPS) of the test compound (4 μL) was added to a 384-well black, low volume plate, the cell suspension (4 μL) was added, and the mixture was incubated at room temperature for 15 min. After incubation, a mixed buffer (4 μL) of 150 mM D-alanine, 1.5 U/mL HRP and 240 μM Amplex red was added to the plate, and the mixture was incubated at room temperature for 30 min, and the fluorescence (excitation wavelength 530 nm, fluorescence wavelength 590 nm) was measured using an Envision plate reader (manufactured by Perkin Elmer Co.). Taking the fluorescence value in the absence of the test compound as 100% and the fluorescence value in the absence of DAAO as 0%, the DAAO activity was regarded to have been inhibited when the fluorescence value decreased by 50% in the presence of the test compound, and the concentration of the test compound at that time was taken as the IC$_{50}$ value (nM). Moreover, to evaluate the cytotoxicity of the test compound, Alamar Blue reagent (manufactured by Wako Pure Chemicals Co.) was added instead of the mixed buffer solution of 150 mM D-alanine, 1.5 U/mL HRP and 240 μM Amplex red, and the fluorescence (excitation wavelength 530 nm, fluorescence wavelength 590 nm) was measured.

The HEK293 cells which stably express human DAAO used in the above-mentioned Experimental Example 2 were constructed by the following method.

Isolation of Human DAAO Polynucleotide and Construction of Forced Expression Cells Reverse transcription was performed on human normal kidney tissue-derived RNA (Clontech Corp.) using reverse transcriptase (SuperScriptIII, Life Technologies Corporation) and oligo (dT) primer (Life Technologies Corporation) according to the protocol of the kit (Life Technologies Corporation) and cDNA was synthesized. Then, using human DAAO_HindIII_F represented by Sequence No. 1 and human DAAO_BamHI_R represented by Sequence No. 2, a PCR reaction (35 cycles of 98° C. for 15 sec, 55° C. for 15 sec and 68° C. for 1 min 30 sec) was performed using DNA polymerase (PrimeSTAR, TAKARA BIO INC.) and cDNA obtained as above as a template. After the PCR reaction, electrophoresis was performed to find that a PCR product of about 1000 base pairs was obtained. The PCR product was cloned in a cloning vector (pCR2.1-TOPO Cloning Kit, Life Technologies Corporation). The sequence of the insert was determined by the dideoxy sequence method (BigDye Terminator v3.1 Cycle Sequencing Kit; Life Technologies Corporation). As a result, the PCR product of about 1000 base pairs was found to have the sequence 154-1197 in the sequence of DAAO (NM_001917.4) registered in NCBI.

To express the ORF full length of DAAO as a protein, the above-mentioned vector was subjected to an enzyme reaction with restriction enzymes HindIII and BamHI at 37° C. for 3 hr, and the restriction enzyme-treated DNA fragment was purified. The DNA fragment containing the ORF was cloned to HindIII and BamHI sites present in the multiple cloning site of the expression vector (pcDNA3.1(+): Invitrogen Co.), whereby an expression plasmid (hDAAO/pcDNA3.1) was constructed.

Then, HEK293 cells were transfected to obtain the forced expression cell line. The cells were spread on a collagen-coated 24-well plate (Corning) to contain 1.0×10$^5$ cells per well on the day before transfection and, using Lipofectamine 2000 (Invitrogen) and hDAAO/pcDNA3.1, transfected according to the protocol. Thereafter, subculture was performed several times using 800 μg/mL geneticin, whereby a drug resistant cell line was obtained.

To confirm acquisition of the human DAAO expression cell line, the cells were spread on a collagen-coated 384-well black, clear bottom plate to 2.5×10$^4$ per well, and the cells were cultured at 37° C. in the presence of 5% CO$_2$ for 24 hr. After culturing, the culture supernatant was removed, and a solution containing flavin adenine dinucleotide was added to Hanks-20 mM Hepes (pH 7.4) buffer to 5.5 μg/mL, added by 20 μL per well to the wells from which the supernatant had been removed, and the mixture was allowed to react at 37° C. in the presence of 5% $CO_2$ for 1 hr. Thereafter, a Hanks-20 mM Hepes (pH 7.4) buffer solution added with Amplex Red (Molecular Probe) to 250 µM, D-alanine to 50 mM and HRP to 0.5 U/mL was added at 5 µL per well, and the mixture was allowed to react at 37° C. in the presence of 5% $CO_2$ for 2 hr. The activity was confirmed by measuring according to the protocol of the Amplex Red, whereby the human DAAO expression cell line was constructed.

The results of some representative compounds are shown in Table 2. Ex. in the Table shows the Example No. mentioned later.

TABLE 2

| Ex | $IC_{50}$ (nM) |
|---|---|
| 1 | 2.4 |
| 4 | 8.9 |
| 9 | 20 |
| 12 | 27 |
| 13 | 14 |
| 14 | 10 |
| 15 | 16 |
| 16 | 8.8 |
| 17 | 8.3 |
| 18 | 6.0 |
| 20 | 4.6 |
| 21 | 5.5 |
| 22 | 8.4 |
| 23 | 25 |
| 24 | 7.0 |
| 25 | 18 |
| 27 | 4.4 |
| 28 | 18 |
| 29 | 13 |
| 30 | 14 |
| 40 | 9.8 |
| 47 | 12 |
| 48 | 11 |
| 52 | 11 |
| 56 | 8.8 |
| 212 | 7.2 |
| 231 | 13 |
| 232 | 13 |
| 237 | 5.1 |
| 254 | 6.3 |

Some representative compounds showed good DAAO inhibitory activity also in DAAO expressing cells. Some representative compounds did not show cytotoxicity.

Experimental Example 3

Impaired Spontaneous Alternation Behavior Test Using MK-801 (Dizocilpine)-induced Mouse Antagonists to N-methyl-D-aspartic acid (NMDA) receptors are known to induce schizophrenia-like symptoms including cognitive impairment in human. Impaired spontaneous alternation behavior (Y-maze) in mouse induced by an NMDA receptor antagonist MK-801 (dizocilpine) was used to detect an improved cognitive impairment effect.

Male ddY mice (5 weeks old) were used for the test. The test compound (vehicle for the Normal group and Control group) was administered orally, and 10 min later, MK-801 hydrogen maleate (physiological saline for the Normal group) (0.15 mg/kg) was intraperitoneally administered to the Control group and the Test compound group. Then, 20 min later, the mice were placed at one end of an arm of a Y-maze having arms of equal length in 3 directions, and the mice were allowed to freely explore for 8 min and the number of entries into the arms during this period was counted. Moreover, successive entry into 3 different arms was taken as a spontaneous alternation behavior and the Alternation rate was calculated by the following formula as a ratio relative to the total number of entries, and used as an index of cognitive function.

Alternation rate(%)=100×Alternation/(Total entry−2)

The results of the representative compound of Ex. 24 are shown in FIG. 1. Ex. in FIG. 1 shows the Example No. mentioned later.

In the Control group, the spontaneous alternation rate significantly decreased as compared to the Normal group and the cognitive impairment was induced. The test compound of Ex. 24 at 0.03-0.1 mg/kg oral administration significantly increased the spontaneous alternation rate relative to the Control group.

As shown in the above-mentioned Experiments, it was confirmed that some representative compounds of the present invention have good DAAO inhibitory action in vitro and also in cellular systems, and the representative compound of Ex. 24 significantly increased the spontaneous alternation rate in an impaired spontaneous alternation behavior test using MK-801 (dizocilpine)-induced mouse. Accordingly, the compound of the formula (I) can be used as a prophylaxis and/or therapeutic agent for diseases associated with DAAO, particularly schizophrenia and neuropathic pain.

Pharmaceutical compositions containing one or more kinds of the compound of the formula (I) or a salt thereof as an active ingredient can be prepared by a method conventionally used and using an excipient generally used in this field, for example, excipient for drugs, carrier for drugs and the like.

The administration may be in any form of oral administration by tablet, pill, capsule, granule, powder, liquid and the like, or by injection such as by intraarticular, intravenous or intramuscular agent or the like, or parenteral administration such as suppository, eye drop, eye ointment, transdermal liquid, ointment, transdermal adhesive preparation, transmucosal liquid, transmucosal adhesive preparation, inhalant and the like.

As a solid composition for oral administration, tablets, powders, granules and the like are used. In such solid composition, one or more kinds of active ingredients are mixed with at least one kind of inert excipient, for example, lactose, mannitol, dextrose, hydroxypropylcellulose, microcrystalline cellulose, starch, polyvinylpyrrolidone and/or magnesium metasilicate aluminate and the like. In accordance with conventional methods, the composition may contain inert additives, for example, lubricant such as magnesium stearate, disintegrating agent such as carboxymethyl starch sodium and the like, stabilizer and solubilizer. Tablets and pills may be film-coated where necessary with a sugar coating film or a film of a gastrosoluble or enteric substance.

Liquid composition for oral administration contains a pharmaceutically acceptable emulsifier, solution agent, suspending agent, syrup, elixir and the like, and a conventionally-used inert diluent, such as purified water or ethanol. The liquid composition may contain adjuvants such as solubilizer, wetting agent, suspending agent and the like, sweetener, flavoring agent, fragrance and preservative, in addition to the inert diluent.

Injection for parenteral administration contains sterile aqueous or non-aqueous solvent, suspending agent or emulsifier. The aqueous solvent includes, for example, distilled water for injection and physiological saline. The non-aqueous solvent includes, for example, propylene glycol, polyethylene glycol, vegetable oil such as olive oil, alcohols such as ethanol, polysorbate 80 (Pharmacopeia name) and the like. Such composition may further contain isotonizing agent, preservative, wetting agent, emulsifier, dispersant, stabilizer or solubilizer. These are sterilized by, for example, filtration through bacteria retaining filter, or addition of a bactericide or irradiation. Moreover, these can be produced as sterile solid compositions, which can be dissolved or suspended in sterile water or sterile injectable solvent prior to use.

The external preparation encompasses ointment, plaster, cream, jelly, cataplasm, spray, lotion, eye drop, eye ointment and the like. It contains generally-used ointment base, toner base, aqueous or non-aqueous liquid, suspension, emulsion and the like. Examples of the ointment or toner base include polyethylene glycol, propylene glycol, white petrolatum, white beeswax, polyoxyethylene hydrogenated castor oil, glycerol monostearate, stearyl alcohol, cetyl alcohol, lauromacrogol, sorbitan sesquioleate and the like.

As transmucosal agents such as inhalant, transnasal agent and the like, those in a solid, liquid or semi-solid form are used, which can be produced by a conventionally-known method. For example, known excipient, and further, pH adjuster, preservative, surfactant, lubricant, stabilizer, thickener and the like may be appropriately added. The administration can be performed using a suitable device for inhalation or insufflation. For example, using a known device such as metered dose inhaler device and nebulizer, and the like, the compound can be administered as a powder of its own or as a formulated powder mixture, or as a solution or suspension in combination with a pharmaceutically acceptable carrier. The dry powder inhalators and the like may be for a single administration or multiple administrations, and a dry powder or a powder-containing capsule can be utilized. Alternatively, it may take a form of a pressurized aerosol spray and the like, that use a suitable ejection agent, such as a suitable gas (e.g., chlorofluoroalkane, hydrofluoroalkane, carbon dioxide or the like).

Generally, for oral administration, the daily dose is about 0.001-100 mg/kg/body weight, preferably 0.1-30 mg/kg/body weight, and more preferably 0.1-1 mg/kg/body weight, which may be administered at once, or in 2-4 portions per day. For intravenous administration, a suitable daily dose is about 0.0001-10 mg/kg/body weight, and this daily dose is administered in a single dose to multiple doses per day. Moreover, a transmucosal agent is administered in about 0.001-100 mg/kg body weight as a single dose or one to multiple portions per day. The dose is determined as appropriate for individual cases in consideration of the symptoms, age, gender and the like.

Although varying depending on the administration route, dosage form, administration site, and the kind of excipient and additive, the pharmaceutical composition of the present invention contains 0.01-100 wt %, in one embodiment, 0.01-50 wt % of one or more kinds of the compound of the formula (I) or a salt thereof, which is the active ingredient.

The compound of the formula (I) can be used in combination with various therapeutic agents or prophylactic agents for diseases for which the compound of the aforementioned formula (I) is considered to show effectiveness. For such combined use, it can be administered by simultaneous administration, or separately and continuously, or at desired time intervals. The simultaneous administration preparation may be a combination agent or separately formulated.

EXAMPLES

The production methods of the compound of the formula (I) are described in more detail by way of Examples. However, the present invention is not limited to the compounds described in the following Examples. In addition, production methods of the starting compounds are shown in the Production Examples. The production methods of the compound of the formula (I) are not limited only to those of the concrete examples shown below, and the compound of the formula (I) can also be produced by a combination of those production methods or methods self-evident to a person skilled in the art.

The following abbreviations are sometimes used in the Production Examples, Examples and Tables shown below. PEx: Production Example number, Ex: Example number, No: compound number, Str: structural formula (Ph: phenyl, Bn: benzyl), PSyn: Production method (shows that the compound was produced using the same production method as the compound of the Production Example number indicated in the column; the compound of Production Example 115 was produced by a method similar to that of Example 7), Syn: Production method (shows that the compound was produced using the same production method as the compound of the Production Example number indicated in the column), Data: Physical data, NMR 1: δ (ppm) of characteristic peak in $^1$H-NMR in DMSO-$d_6$, ESI+: m/z value by mass spectrometry (ionization method ESI, unless otherwise indicated (M+H)$^+$), ESI−: m/z value (ionization method ESI, unless otherwise indicated (M−H)$^−$), APCI+: m/z value by mass spectrometry (ionization method APCI, unless otherwise indicated (M+H)$^+$), FAB+: m/z value by mass spectrometry (ionization method FAB, unless otherwise indicated (M+H)$^+$), ESI/APCI+: m/z value by mass spectrometry (ionization method ESI/APCI multimode, unless otherwise indicated (M+H)$^+$), ESI/APCI−: m/z value by mass spectrometry (ionization method ESI/APCI multimode, unless otherwise indicated (M−H)$^−$), PS-carbodiimide in Example 11 means carbodiimide (condensing agent) supported on polystyrene resin. "M" in the Production Examples and Examples means mol/L. HCl in the structural formula means hydrochloride.

In the structural formulas, a compound having an intersecting double bond (e.g., PEx.13) means a mixture of E form and Z form.

Production Example 1

Toluene (10 ml) was added to 3-chloro[1,4]benzodioxino[2,3-c]pyridazine (600 mg), and (E)-2-phenylvinylboronic acid (480 mg), tetrakis(triphenylphosphine)palladium (315 mg) and 2M aqueous sodium carbonate solution (1.6 mL) were added at room temperature. The reaction mixture was stirred at 120° C. for 14 hr. Water was added and the mixture was extracted with chloroform. The organic layer was washed with saturated aqueous ammonium chloride solution and saturated brine, dried over anhydrous magnesium sulfate and the solvent was concentrated under reduced pressure. The obtained residue was washed with a mixed solvent of hexane and ethyl acetate and filtered. The obtained solid was dried under reduced pressure to give 3-[(E)-2-phenylvinyl] [1,4]benzodioxino[2,3-c]pyridazine (386 mg).

Production Example 2

Under ice-cooling, to a solution (5 mL) of benzyl alcohol (350 μL) in toluene was added t-butoxy potassium (375 mg), and the mixture was stirred for 20 min. To the mixture was added a toluene-dimethylformamide (1:1) suspension (10 ml) of 3-[(E)-2-phenylvinyl] [1,4]benzodioxino[2,3-c]pyridazine (386 mg) at 0° C., and the mixture was stirred at 120° C. for 19 hr. Water was added, and the mixture was extracted with chloroform. The organic layer was washed with saturated brine, dried over anhydrous magnesium sulfate, and the solvent was concentrated under reduced pressure. The obtained residue was purified by silica gel column chromatography (hexane-ethyl acetate) to give 3,4-bis(benzyloxy)-6-[(E)-2-phenylvinyl]pyridazine (473 mg).

Production Example 3

To a sealed reaction container were added 3-iodo[1,4]benzodioxino[2,3-c]pyridazine (200 mg) synthesized in Production Example 9 to be mentioned later, 4-ethynylphenyl trifluoromethyl ether (0.15 mL), copper iodide (6 mg), triethylamine (64 mg), bis(triphenylphosphine)palladium (II) dichloride (22 mg) and dimethylformamide (5 mL), and the mixture was stirred at 120° C. for 0.5 hr. Ethyl acetate and water were added, the organic layer was dried over anhydrous sodium sulfate, and the solvent was concentrated under reduced pressure. The obtained residue was purified by silica gel column chromatography (hexane-ethyl acetate) to give 3-{[4-(trifluoromethoxy)phenyl]ethynyl}[1,4]benzodioxino[2,3-c]pyridazine (100 mg).

Production Example 4

Under an argon atmosphere, to 3-chloro[1,4]benzodioxino[2,3-c]pyridazine (500 mg) was added 1,2-dimethoxyethane (7.5 mL), and the mixture was stirred. 2M Aqueous sodium carbonate solution (3.0 ml), (E)-2-[3-(trifluoromethyl)phenyl]vinylboronic acid (580 mg) and tetrakis(triphenylphosphine)palladium (130 mg) were added, and the mixture was stirred at 100° C. for 3 hr. The reaction mixture was diluted with ethyl acetate, and water was added. The organic layer was separated, dried over anhydrous sodium sulfate, and the solvent was concentrated under reduced pressure. The obtained residue was purified by silica gel column chromatography (hexane-ethyl acetate) to give a crude product (500 mg).

Successively, under an argon atmosphere and under ice-cooling, to a solution (5 mL) of benzyl alcohol (380 mg) in toluene was added t-butoxy potassium (400 mg), and the mixture was stirred. To the mixture was added dropwise a solution (15 mL) of the crude product (500 mg) in toluene-dimethylformamide (2:1) at 0° C., and the mixture was stirred at 120° C. for 2 hr. The reaction mixture was diluted with ethyl acetate, and water was added. The organic layer was separated, dried over anhydrous sodium sulfate, and the solvent was concentrated under reduced pressure. The obtained residue was purified by silica gel column chromatography (hexane-ethyl acetate) to give 3,4-bis(benzyloxy)-6-{(E)-2-[3-(trifluoromethyl)phenyl]vinyl}pyridazine (400 mg).

Production Example 5

To a solution (10 ml) of 3,4-bis(benzyloxy)-6-[(E)-2-(4-chlorophenyl)vinyl]pyridazine (200 mg) in dichloromethane were added triethylamine (200 μL) and 2,4,6-triisopropylbenzenesulfonylhydrazide (700 mg), and the mixture was stirred at room temperature for 40 hr. Triethylamine (200 μL) and 2,4,6-triisopropylbenzenesulfonylhydrazide (700 mg) were added, and the mixture was further stirred at room temperature for 24 hr. Water was added, and the mixture was extracted with chloroform. The organic layer was washed with saturated brine, dried over anhydrous magnesium sulfate, and the solvent was concentrated under reduced pressure. The residue was purified by silica gel column chromatography (hexane-ethyl acetate) to give 3,4-bis(benzyloxy)-6-[2-(4-chlorophenyl)ethyl]pyridazine (70 mg).

Production Example 6

To 3-chloro[1,4]benzodioxino[2,3-c]pyridazine (1.71 g) was added a mixed solvent of dimethyl sulfoxide-methanol (1:1) (40 ml), and the mixture was stirred. 1,1'-Bis(diphenylphosphino)ferrocene (1.72 g), diacetoxypalladium (350 mg) and triethylamine (2.2 mL) were added, and the mixture was stirred under a carbon monoxide atmosphere at 1 atm, 80° C. for 19 hr. Water was added and the mixture was extracted with ethyl acetate, and the organic layer was washed with water and saturated brine, and dried over anhydrous magnesium sulfate. The solvent was concentrated under reduced pressure, and the obtained residue was purified by silica gel column chromatography (hexane-ethyl acetate) to give methyl [1,4]benzodioxino[2,3-c]pyridazine-3-carboxylate (950 mg).

Production Example 7

To methyl [1,4]benzodioxino[2,3-c]pyridazine-3-carboxylate (950 mg) was added a mixed solvent of tetrahydrofuran-methanol (1:1) (20 ml), and the mixture was stirred under ice-cooling. To the mixture was added sodium borohydride (450 mg), and the mixture was stirred at 0° C. for 2 hr. Water was added and the mixture was extracted with ethyl acetate. The organic layer was washed with saturated brine, and dried over anhydrous magnesium sulfate. The solvent was concentrated under reduced pressure, and the residue was washed with water to give [1,4]benzodioxino[2,3-c]pyridazin-3-ylmethanol (560 mg).

Production Example 8

To [1,4]benzodioxino[2,3-c]pyridazin-3-ylmethanol (8.1 g) was added 1,2-dichloroethane (80 ml) and the mixture was stirred. Thionyl bromide (38.9 g) was added, and the mixture was stirred with heating under reflux for 2 hr. The mixture was diluted with chloroform, and the organic layer was washed with saturated aqueous sodium hydrogen carbonate solution, and dried over anhydrous sodium sulfate. The solvent was concentrated under reduced pressure, and the residue was washed with diethyl ether to give 3-(bromomethyl)[1,4]benzodioxino[2,3-c]pyridazine (8.0 g).

Production Example 9

Under an argon atmosphere, 3-chloro[1,4]benzodioxino[2,3-c]pyridazine (5.0 g), sodium iodide (6.79 g) and hydrogen iodide (55%) (57.98 g) were added and the mixture was stirred at 140° C. for 1 hr. The reaction mixture was diluted with ethyl acetate and aqueous sodium hydrogen carbonate solution was added, and the mixture was extracted. The organic layer was dried over anhydrous sodium sulfate, and the solvent was concentrated under reduced pressure to give 3-iodo[1,4]benzodioxino[2,3-c]pyridazine (1.95 g).

Production Example 10

To 3-(bromomethyl)[1,4]benzodioxino[2,3-c]pyridazine (500 mg) were added dimethylformamide (10 ml), potassium iodide (30 mg), potassium carbonate (750 mg) and 2-naphthylalcohol (290 mg), and the mixture was stirred at room temperature for 24 hr. Water was added and the mixture was extracted with ethyl acetate. The organic layer was washed with 1M aqueous sodium hydroxide solution and saturated brine, and dried over anhydrous sodium sulfate. The solvent was concentrated under reduced pressure, and the residue was washed with diethyl ether and the resulting solid was filtered and dried under reduced pressure to give 3-[(2-naphthyloxy)methyl] [1,4]benzodioxino[2,3-c]pyridazine (400 mg).

Production Example 11

To a solution (20 ml) of ethyl (2E)-3-([1,4]benzodioxino[2,3-c]pyridazin-3-yl)acrylate (649 mg) in acetic acid was added 10% palladium-carbon (100 mg), and the mixture was stirred at room temperature for 7 days under a hydrogen atmosphere. The catalyst was filtered off through celite, and the filtrate was concentrated under reduced pressure. To the residue was added saturated aqueous sodium hydrogen carbonate solution and the mixture was extracted with chloroform. The organic layer was dried over anhydrous magnesium sulfate, and the solvent was concentrated under reduced pressure to give ethyl 3-([1,4]benzodioxino[2,3-c]pyridazin-3-yl)propanoate (609 mg).

Production Example 12

To ethyl 3-([1,4]benzodioxino[2,3-c]pyridazin-3-yl)propanoate (609 mg) were added toluene (10 ml), a solution (10 ml) of benzyl alcohol (1.08 g) in toluene and t-butoxy potassium (1.12 g), and the mixture was stirred at 120° C. for 6 hr. Water was added, and the aqueous layer was washed with ethyl acetate. To the aqueous layer was added 1M hydrochloric acid (30 ml), and the mixture was washed with chloroform. The aqueous layer was extracted with a mixed solvent (chloroform:ethanol=3:1). The organic layer was dried over anhydrous magnesium sulfate, and the solvent was concentrated under reduced pressure to give a crude product (491 mg). Successively, to a solution (20 ml) of the obtained crude product (491 mg) in ethanol was added 10% palladium-carbon (50 mg), and the mixture was stirred at room temperature for 16 hr under a hydrogen atmosphere. The catalyst was filtered off through celite, and the filtrate was concentrated under reduced pressure to give 3-(5-hydroxy-6-oxo-1,6-dihydropyridazin-3-yl)propionic acid (215 mg).

Production Example 13

Under an argon atmosphere, a mixture of 1-ethynylnaphthalene (1.0 g) and 1,3,2-benzodioxaborole (0.79 g) was stirred at 70° C. for 1 hr. The reaction mixture was concentrated under reduced pressure to give crude product 1 (1.21 g).

Successively, to the obtained crude product 1 (1.21 g) was added water (10 ml) and the mixture was stirred at room temperature for 1 hr. To the reaction mixture was added hexane and the mixture was stirred at room temperature. The resulting solid was collected by filtration, and washed with hexane to give a crude product 2 (510 mg).

Successively, to the obtained crude product 2 (430 mg) were added 3-chloro[1,4]benzodioxino[2,3-c]pyridazine (400 mg), 1,2-dimethoxyethane (7.5 mL), 2M aqueous sodium carbonate solution (3.0 ml) and tetrakis(triphenylphosphine)palladium (110 mg) at room temperature. The reaction mixture was stirred at 100° C. for 3 hr. Water was added, and the mixture was extracted with ethyl acetate. The organic layer was dried over anhydrous magnesium sulfate and the solvent was concentrated under reduced pressure. The obtained residue was purified by silica gel column chromatography (hexane-ethyl acetate) to give 3-[2-(1-naphthyl)vinyl] [1,4]benzodioxino[2,3-c]pyridazine (600 mg).

Production Example 14

Under an argon atmosphere, a mixture of 1-ethynyl-2-methylbenzene (1.0 g) and 1,3,2-benzodioxaborole (1.05 mL) was stirred at 70° C. for 1 hr. The reaction mixture was concentrated under reduced pressure to give crude product 3 (1.36 g).

Successively, to the obtained crude product 3 (1.36 g) was added water (10 ml) and the mixture was stirred at room temperature for 1 hr. To the reaction mixture was added hexane and the mixture was stirred at room temperature. The resulting solid was collected by filtration, and washed with hexane to give a crude product 4 (160 mg).

Successively, to the obtained crude product 4 (160 mg) were added 3-chloro[1,4]benzodioxino[2,3-c]pyridazine (220 mg), 1,2-dimethoxyethane (5 mL), 2M aqueous sodium carbonate solution (2.0 ml) and tetrakis(triphenylphosphine) palladium (130 mg) at room temperature. The reaction mixture was stirred at 100° C. for 3 hr. Water was added, and the residue was filtered to give a crude product 5 (360 mg). Under ice-cooling, to a solution (5 mL) of benzyl alcohol (320 mg) in toluene was added t-butoxy potassium (330 mg) and the mixture was stirred for 10 min. To the mixture was added a solution (15 mL) of the crude product 5 (360 mg) in toluene-dimethylformamide (1:2) at 0° C., and the mixture was stirred at 120° C. for 4 hr. Water was added, and the mixture was extracted with ethyl acetate. The organic layer was dried over anhydrous magnesium sulfate and the solvent was concentrated under reduced pressure. The obtained residue was purified by silica gel column chromatography (hexane-ethyl acetate) to give 3,4-bis(benzyloxy)-6-[2-(2-methylphenyl)vinyl]pyridazine (410 mg).

Production Example 24

Under an argon atmosphere, to 3-chloro[1,4]benzodioxino[2,3-c]pyridazine (500 mg) were added 1,2-dimethoxyethane (7.5 ml), 2M aqueous sodium carbonate solution (3.0 mL), 2-[(E)-2-(3,5-difluorophenyl)vinyl]-4,4,5,5-tetramethyl-1,3,2-dioxaborolane (720 mg) and tetrakis(triphenylphosphine)palladium (130 mg). The reaction mixture was stirred at 100° C. for 3 hr and cooled to room temperature. Water was added, and the obtained solid was collected by filtration and dried under reduced pressure to give 3-[(E)-2-(3,5-difluorophenyl)vinyl] [1,4]benzodioxino[2,3-c]pyridazine (700 mg).

Production Example 50

Under ice-cooling, to a solution (20 mL) of benzyl alcohol (580 mg) in tetrahydrofuran was added 60% sodium hydride (220 mg), and the mixture was stirred for 10 min. To the mixture was added a solution (10 mL) of 3-[(E)-2-(3,5-difluorophenyl)vinyl] [1,4]benzodioxino[2,3-c]pyridazine (700 mg) in tetrahydrofuran, and the mixture was stirred at 60° C. for 4 hr. Water was added, and the mixture was extracted with ethyl acetate. The organic layer was dried over anhydrous magnesium sulfate and the solvent was concentrated under reduced pressure. The obtained residue was purified by silica gel column chromatography (hexane-ethyl acetate) to give 3,4-bis(benzyloxy)-6-[(E)-2-(3,5-difluorophenyl)vinyl]pyridazine (710 mg).

Example 1

To a solution (8 mL) of 3,4-bis(benzyloxy)-6-[(E)-2-phenylvinyl]pyridazine (272 mg) in ethanol was added 10% palladium-carbon (90 mg), and the mixture was stirred under a hydrogen atmosphere at room temperature for 4 hr. The catalyst was filtered off through celite, and the filtrate was concentrated under reduced pressure. To the residue was added ethyl acetate-chloroform, and the resulting solid was collected by filtration and dried under reduced pressure to give 3-hydroxy-6-(2-phenylethyl)pyridazin-4(1H)-one (60 mg).

Example 2

To a solution (5 mL) of 3,4-bis(benzyloxy)-6-[(E)-2-(4-chlorophenyl)vinyl]pyridazine (150 mg) in dichloromethane was added a solution (770 µL) of 1M boron tribromide in dichloromethane at −78° C. and the mixture was stirred at 0° C. for 3 hr. Methanol was added to terminate the reaction, and the solvent was concentrated under reduced pressure. The residue was purified by silica gel column chromatography (chloroform-methanol) and the obtained solid was washed with ethanol-water, collected by filtration and dried under reduced pressure to give 6-[(E)-2-(4-chlorophenyl)vinyl]-4-hydroxypyridazin-3(2H)-one (58 mg).

Example 3

Under a nitrogen atmosphere, 10% palladium-barium sulfate (120 mg) was suspended in ethanol (10 ml), and 3,4-bis(benzyloxy)-6-[(2-naphthyloxy)methyl]pyridazine (120 mg) was added. Under a hydrogen atmosphere, the mixture was stirred at room temperature for 5 hr. The catalyst was filtered off through celite, and the filtrate was concentrated under reduced pressure. The residue was washed with diethyl ether, and the resulting solid was collected by filtration and dried under reduced pressure to give 3-hydroxy-6-[(2-naphthyloxy)methyl]pyridazin-4(1H)-one (30 mg).

Example 4

A solution (130 ml) of 3-(chloromethyl) [1,4]benzodioxino[2,3-c]pyridazine (941 mg) in dimethylformamide was prepared. To this solution (1 mL) were added 2-fluorophenol (4.5 mg), potassium carbonate (5 mg) and potassium iodide (5 mg) and the mixture was stirred at room temperature for 20 hr. Water was added to the reaction solution and the mixture was extracted with chloroform. The organic layer was concentrated under reduced pressure, to the residue were added a separately-prepared solution (1 mL) of param-ethoxybenzylalcohol (1.2 mL) in toluene (150 ml) and t-butoxy potassium (10 mg) and the mixture was stirred at 120° C. for 17 hr. To the reaction solution was added 1M hydrochloric acid and the mixture was extracted with chloroform. The organic layer was concentrated under reduced pressure, the residue was dissolved in dichloromethane (1 mL), thioanisole (30 µL) and trifluoroacetic acid (0.5 mL) were added and the mixture was stirred at room temperature for 3 days. The solvent was concentrated under reduced pressure, and the obtained residue was purified by reversed-phase column chromatography (methanol-0.1% aqueous formic acid solution) to give 6-[(2-fluorophenoxy)methyl]-4-hydroxypyridazin-4(1H)-one (1.0 mg).

Example 5

A solution (184 mL) of 2-(chloromethyl)-5-[(4-methoxybenzyl)oxy]pyridin-4(1H)-one (1.62 g) in dimethylformamide was prepared. To this solution (1 mL) were added 1,4'-bipiperidin-4-ol (7.4 mg) and potassium carbonate (6 mg) and the mixture was stirred at room temperature for 22 hr, and further at 60° C. for 3 days. Water was added to the reaction solution and the mixture was extracted with chloroform. The organic layer was concentrated under reduced pressure, to the residue were added thioanisole (100 µL) and trifluoroacetic acid (1 mL) and the mixture was stirred at room temperature for 21 hr. The solvent was concentrated under reduced pressure, the obtained residue was purified by reversed-phase column chromatography (methanol-0.1% aqueous formic acid solution) to give 5-hydroxy-2-[(4-hydroxy-1,4'-bipiperidin-1'-yl)methyl]pyridin-4(1H)-one (1.4 mg).

Example 6

To a solution (10 mL) of 3-(bromomethyl) [1,4]benzodioxino[2,3-c]pyridazine (500 mg) in N,N-dimethylformamide were added potassium iodide (29 mg), potassium carbonate (620 mg) and 3,5-difluorophenol (350 mg) and the mixture was stirred at room temperature for 24 hr. Water was added to the reaction solution and the mixture was extracted with ethyl acetate, the organic layer was washed with 1M aqueous sodium hydroxide solution and saturated brine, and dried over anhydrous sodium sulfate. The solvent was concentrated under reduced pressure to give a crude product 6 (350 mg).

Successively, under ice-cooling, to a solution (5 mL) of benzyl alcohol (280 µL) in toluene was added t-butoxy potassium (300 mg) and the mixture was stirred for 15 min. The crude product 6 (350 mg) in a mixed solvent (15 mL) of N,N-dimethylformamide-toluene (1:2) was added at 0° C., and the mixture was stirred at 110° C. for 5 hr. To the reaction solution was added ethyl acetate, and the organic layer was washed with 1M aqueous sodium hydroxide solution and saturated brine, and the mixture was dried over anhydrous sodium sulfate. The solvent was concentrated under reduced pressure and the obtained residue was added to a suspension of 10% palladium-barium sulfate (500 mg) in ethanol (10 ml) under a nitrogen atmosphere, and the mixture was stirred under a hydrogen atmosphere at room temperature for 5 hr. The catalyst was filtered off through celite, and the filtrate was concentrated under reduced pressure. The residue was purified by silica gel column chromatography (chloroform-methanol) to give 6-[(3,5-difluorophenoxy)methyl]-4-hydroxypyridazin-4(1H)-one (73 mg).

Example 7

To 5-chloro-3-hydroxypyridin-2(1H)-one (500 mg) was added acetic acid (20 ml), and N-bromosuccinimide (734 mg) was added at room temperature. The reaction mixture was stirred at room temperature for 5 hr. The obtained solid was collected by filtration and washed with ethyl acetate. The obtained residue was purified by reversed-phase column chromatography (methanol-0.1% aqueous formic acid solution) and solidified by dimethylformamide to give 6-bromo-5-chloro-3-hydroxypyridin-2(1H)-one (40 mg).

Example 8

To a suspension of 55% sodium hydride (1.6 g) in tetrahydrofuran (100 ml) was added 6-bromo-5-chloro-3-hydroxypyridin-2(1H)-one (2.71 g), chloromethyl methyl ether (2.8 mL) was added, and the mixture was stirred at room temperature for 3 hr. Water was added and the mixture was extracted with chloroform. The organic layer was concentrated under reduced pressure. The obtained residue was purified by silica gel column chromatography to give a crude product 7 (1.22 g).
To the obtained crude product 7 (1.02 g) were added 1,2-dimethoxyethane (18 mL), 2M aqueous sodium carbonate solution (2 mL), trimethylboroxin (480 µL) and tetrakis(triphenylphosphine)palladium (377 mg), and the mixture was stirred under an argon atmosphere under microwave irradiation at 130° C. for 1 hr. Water was added and the mixture was extracted with chloroform and the organic phase was concentrated under reduced pressure. The obtained residue was purified by silica gel column chromatography to give a crude product 8 (255 mg).
Successively, to the obtained crude product 8 (55 mg) was added dichloromethane (5 mL), a solution (1 mL) of 1M boron tribromide in dichloromethane was added under ice-cooling and the mixture was stirred at the same temperature for 30 min. The solvent was concentrated under reduced pressure, and the obtained residue was purified by reversed-phase column chromatography (methanol-0.1% aqueous formic acid solution) to give 5-chloro-3-hydroxy-6-methylpyridin-2(1H)-one (8 mg).

Example 9

To a suspension of 55% sodium hydride (253 mg) in dimethylformamide (15 mL) was added 5-bromo-3-hydroxypyridin-2(1H)-one (500 mg) under ice-cooling. After stirring at room temperature for 1 hr, chloromethyl methyl ether (435 µL) was added under ice-cooling, and the mixture was stirred at room temperature for 3 hr. Water was added and the mixture was extracted with ethyl acetate. The organic layer was washed with saturated brine, and dried over anhydrous magnesium sulfate, and the solvent was concentrated under reduced pressure. The obtained residue was purified by silica gel column chromatography (chloroform-methanol) to give a crude product 9 (149 mg).
Successively, to the obtained crude product 9 (149 mg) were added dioxane (10 ml), water (2 mL), trans-2-phenylvinylboronic acid (119 mg), potassium phosphate (341 mg) and tetrakis(triphenylphosphine)palladium (62 mg), and the mixture was stirred under an argon atmosphere at 100° C. for 6 hr. Water was added and the mixture was extracted with ethyl acetate. The organic layer was washed with saturated brine, dried over anhydrous magnesium sulfate and the solvent was concentrated under reduced pressure. The obtained residue was purified by silica gel column chromatography (hexane-ethyl acetate) to give a crude product 10 (114 mg).
Successively, the obtained crude product 10 (114 mg) was dissolved in ethanol (10 ml), 10% palladium-carbon (50 mg) and ethanol (10 ml) were added, and the mixture was stirred under a hydrogen atmosphere at room temperature for 4 hr. The catalyst was filtered off through celite, and the filtrate was concentrated under reduced pressure to give a crude product 11 (94 mg).

Successively, to a solution (5 mL) of the obtained crude product 11 (94 mg) in dichloromethane was added a solution (5 mL) of 1M boron tribromide in dichloromethane under ice-cooling and the mixture was stirred at room temperature for 4 hr. The obtained solid was collected by filtration, and washed with water. The obtained residue was purified by silica gel column chromatography (chloroform-methanol) and solidified with ethanol to give 3-hydroxy-5-(2-phenylethyl)pyridin-2(1H)-one (38 mg).

Example 10

To a suspension of 55% sodium hydride (1.6 g) in tetrahydrofuran (100 ml) were added 6-bromo-5-chloro-3-hydroxypyridin-2(1H)-one (2.71 g) and chloromethyl methyl ether (2.8 mL), and the mixture was stirred at room temperature for 3 hr. Water was added and the mixture was extracted with chloroform, and the organic layer was concentrated under reduced pressure. The obtained residue was purified by silica gel column chromatography to give a crude product 12 (1.22 g).
Successively, the crude product 12 (1.02 g) was dissolved in 1,2-dimethoxyethane (18 mL), trimethylboroxin (479 µL), tetrakis(triphenylphosphine)palladium (377 mg) and 2M aqueous sodium carbonate solution (2 mL) were added, and the mixture was stirred at 130° C. under microwave irradiation for 1 hr. After allowing to cool, water was added and the mixture was extracted with chloroform, and the organic layer was concentrated under reduced pressure. The obtained residue was purified by silica gel column chromatography to give a crude product 13 (255 mg).
Successively, to the obtained crude product 13 (156 mg) were added toluene (4 mL) and water (0.5 mL), (E)-2-phenylvinylboronic acid (140 mg), 2-dicyclohexylphosphino-2',6'-dimethoxybiphenyl (52 mg), tris(dibenzylideneacetone)dipalladium (0) (29 mg) and potassium phosphate (268 mg) were added at room temperature and the mixture was stirred at 130° C. under microwave irradiation for 1 hr. After allowing to cool, water was added and the mixture was extracted with dichloromethane, and the solvent was concentrated under reduced pressure. The obtained residue was purified by silica gel column chromatography to give a crude product 14 (92 mg).
Successively, to the crude product 14 was added the crude product 14 (38 mg) separately synthesized in the same manner as above. To a solution of the mixed crude product 14 (130 mg) in ethanol (10 ml) was added 10% palladium-carbon (100 mg), and the mixture was stirred under a hydrogen atmosphere at room temperature for 3 hr. The catalyst was filtered off through celite, and the filtrate was concentrated under reduced pressure. The obtained residue was purified by silica gel column chromatography to give a crude product 15 (77 mg).
Successively, to a solution of the obtained crude product 15 (77 mg) in dichloromethane (5 mL) was added a solution (1 mL) of 1M boron tribromide in dichloromethane under ice-cooling, and the mixture was stirred at the same temperature for 30 min. The solvent was concentrated under reduced pressure, and the residues was purified by reversed-phase column chromatography (methanol-0.1% aqueous formic acid solution) to give 3-hydroxy-6-methyl-5-(2-phenylethyl)pyridin-2 (1H)-one (28 mg).

Example 11

A solution of 3-(5-hydroxy-6-oxo-1,6-dihydropyridazin-3-yl)propionic acid (215 mg) and 1-hydroxybenzotriazole (158 mg) in N,N-dimethylformamide (100 ml) was prepared, the solution (1 mL) was added to a solution (0.5 mol/L, 30 μL) of N,N-dimethylethylenediamine in N-methylpyrrolidinone, PS-carbodiimide (50 mg) was added and the mixture was stirred for 16 hr. The reaction mixture was filtered, and the filtrate was purified by reversed-phase column chromatography (methanol-0.1% aqueous formic acid solution) to give N-[2-(dimethylamino)ethyl]-3-(5-hydroxy-6-oxo-1,6-dihydropyridazin-3-yl)propanamide (1.7 mg).

Example 24

A mixture of 10% palladium-carbon (280 mg), ethanol (25 mL) and 3,4-bis(benzyloxy)-6-[(E)-2-(3,5-difluorophenyl)vinyl]pyridazine (710 mg) was stirred under a hydrogen atmosphere at room temperature for 1 hr. The catalyst was filtered off through celite, and the filtrate was concentrated under reduced pressure. To the obtained residue was added diethyl ether and the obtained solid was dried under reduced pressure to give 6-[2-(3,5-difluorophenyl)ethyl]-4-hydroxy-pyridazin-3(2H)-one (140 mg).

The compounds shown in the following Tables were produced in the same manner as in the aforementioned Production Examples and Examples.

The chemical structural formulas, production methods and physicochemical data of the compounds of Production Examples are shown in the following Table 3 to Table 17, the chemical structural formulas of the Example compounds are shown in Table 18 to Table 34, and the production methods and physicochemical data of the Example compounds are shown in Table 35 to Table 45.

The structures of other compounds of the present invention are shown in the following Table 46-Table 57. They can be easily synthesized by the above-mentioned production methods, the methods described in the Examples and the methods obvious to those of ordinary skill in the art, or modified methods thereof.

TABLE 3

| PEx | PSyn | Str | Data |
|---|---|---|---|
| 1 | 1 | | ESI+: 289 |
| 2 | 2 | | ESI+: 395 |
| 3 | 3 | | ESI+: 371 |
| 4 | 4 | | ESI+: 463 |
| 5 | 5 | | ESI+: 431/433 |
| 6 | 6 | | ESI+: 245 |
| 7 | 7 | | ESI+: 217 |

TABLE 4

| PEx | PSyn | Str | Data |
|---|---|---|---|
| 8 | 8 | 3-(bromomethyl)-benzo[b]pyridazino[3,4-e][1,4]dioxine | ESI+: 279/281 |
| 9 | 9 | 3-iodo-benzo[b]pyridazino[3,4-e][1,4]dioxine | ESI+: 313 |
| 10 | 10 | 3-((naphthalen-2-yloxy)methyl)-benzo[b]pyridazino[3,4-e][1,4]dioxine | ESI+: 343 |
| 11 | 11 | ethyl 3-(benzo[b]pyridazino[3,4-e][1,4]dioxin-3-yl)propanoate | ESI/APCI+: 287 |
| 12 | 12 | 3-(5-hydroxy-6-oxo-1,6-dihydropyridazin-3-yl)propanoic acid | ESI/APCI −: 183 |
| 13 | 13 | 3-(2-(naphthalen-1-yl)vinyl)-benzo[b]pyridazino[3,4-e][1,4]dioxine | ESI+: 339 |
| 14 | 14 | 4,5-bis(benzyloxy)-3-(2-(o-tolyl)vinyl)pyridazine | ESI+: 409 |
| 15 | 1 | 3-(2-(3-methoxyphenyl)vinyl)-benzo[b]pyridazino[3,4-e][1,4]dioxine | ESI+: 319 |
| 16 | 1 | 3-((E)-but-1-en-1-yl)-benzo[b]pyridazino[3,4-e][1,4]dioxine | ESI+: 241 |

TABLE 5

| PEx | PSyn | Str | Data |
|---|---|---|---|
| 17 | 1 | 3-fluorophenyl-CH=CH-[pyridazino-benzodioxine] | ESI+: 307 |
| 18 | 1 | 3,5-bis(CF3)phenyl-CH=CH-[pyridazino-benzodioxine] | ESI+: 425 |
| 19 | 13 | 2-fluorophenyl-CH=CH-[pyridazino-benzodioxine] | APCI+: 307 |
| 20 | 13 | 3-methylphenyl-CH=CH-[pyridazino-benzodioxine] | ESI+: 303 |
| 21 | 1 | 2,4-difluorophenyl-CH=CH-[pyridazino-benzodioxine] | ESI+: 325 |
| 22 | 1 | 4-phenylphenyl-CH=CH-[pyridazino-benzodioxine] | ESI+: 365 |
| 23 | 1 | 3,5-dimethoxyphenyl-CH=CH-[pyridazino-benzodioxine] | ESI+: 349 |
| 24 | 24 | 3,5-difluorophenyl-CH=CH-[pyridazino-benzodioxine] | ESI+: 325 |

TABLE 6

| PEx | PSyn | Str | Data |
|---|---|---|---|
| 25 | 13 | 4-tert-butylphenyl-CH=CH-[pyridazino-benzodioxine] | ESI+: 345 |
| 26 | 1 | CH3O-CH2-CH=CH-[pyridazino-benzodioxine] | ESI+: 257 |
| 27 | 1 | H3C-CH=CH-[pyridazino-benzodioxine] | ESI+: 227 |
| 28 | 3 | 2-CF3-phenyl-C≡C-[pyridazino-benzodioxine] | ESI+: 355 |
| 29 | 2 | CH2=CH-[4,5-bis(OBn)pyridazine] | ESI+: 319 |
| 30 | 2 | H3C-CH=CH-[4,5-bis(OBn)pyridazine] | ESI+: 333 |
| 31 | 2 | H3C-CH2-CH=CH-[4,5-bis(OBn)pyridazine] | ESI+: 347 |
| 32 | 2 | cyclohexyl-CH=CH-[4,5-bis(OBn)pyridazine] | ESI+: 401 |

TABLE 7

| PEx | PSyn | Str | Data |
|---|---|---|---|
| 33 | 2 | (CH3)3C-CH=CH-[4,5-bis(OBn)pyridazine] | ESI+: 375 |
| 34 | 2 | cyclohex-1-enyl-[4,5-bis(OBn)pyridazine] | ESI+: 373 |

TABLE 7-continued

| PEx | PSyn | Str | Data |
|-----|------|-----|------|
| 35 | 2 | (styrene with Ph substituent attached to 5,6-bis(benzyloxy)pyridazine) | ESI+: 395 |
| 36 | 2 | Ph-(CH2)2-CH=CH- attached to 5,6-bis(benzyloxy)pyridazine | ESI+: 423 |
| 37 | 1 | vinyl-substituted pyridazine fused with benzodioxine | ESI+: 213 |
| 38 | 2 | 1-naphthyl-CH=CH- attached to 5,6-bis(benzyloxy)pyridazine | ESI+: 445 |
| 39 | 2 | 4-F-C6H4-CH=CH- attached to 5,6-bis(benzyloxy)pyridazine | ESI+: 413 |
| 40 | 2 | 4-F3C-C6H4-CH=CH- attached to 5,6-bis(benzyloxy)pyridazine | ESI+: 463 |
| 41 | 2 | 4-H3C-C6H4-CH=CH- attached to 5,6-bis(benzyloxy)pyridazine | ESI+: 409 |

TABLE 8

| PEx | PSyn | Str | Data |
|-----|------|-----|------|
| 42 | 2 | 4-CH3O-C6H4-CH=CH- attached to 5,6-bis(benzyloxy)pyridazine | ESI+: 425 |
| 43 | 2 | 4-Ph-C6H4-CH=CH- attached to 5,6-bis(benzyloxy)pyridazine | ESI+: 471 |
| 44 | 2 | 3-CH3O-C6H4-CH=CH- attached to 5,6-bis(benzyloxy)pyridazine | ESI+: 425 |
| 45 | 2 | 3-F-C6H4-CH=CH- attached to 5,6-bis(benzyloxy)pyridazine | ESI+: 413 |
| 46 | 2 | 3,5-bis(CF3)-C6H3-CH=CH- attached to 5,6-bis(benzyloxy)pyridazine | ESI+: 531 |
| 47 | 2 | 2-F-C6H4-CH=CH- attached to 5,6-bis(benzyloxy)pyridazine | ESI+: 413 |
| 48 | 2 | 3-H3C-C6H4-CH=CH- attached to 5,6-bis(benzyloxy)pyridazine | ESI+: 409 |
| 49 | 2 | 3,5-bis(OCH3)-C6H3-CH=CH- attached to 5,6-bis(benzyloxy)pyridazine | ESI+: 455 |

TABLE 9
| PEx | PSyn | Str | Data |
|---|---|---|---|
| 50 | 50 | 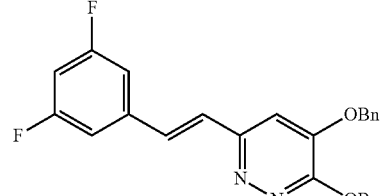 | ESI+: 431 |
| 51 | 2 | 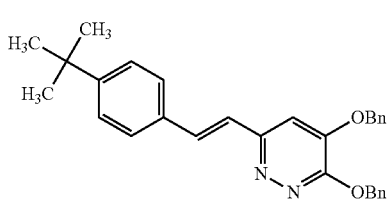 [SMILES: CC(C)(C)c1ccc(/C=C/c2cc(OCc3ccccc3)c(OCc3ccccc3)nn2)cc1] | ESI+: 451 |
| 52 | 2 | 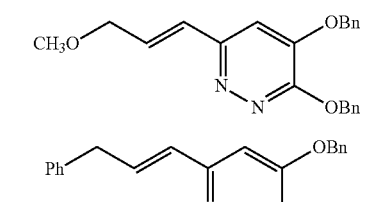 | ESI+: 363 |
| 53 | 2 | 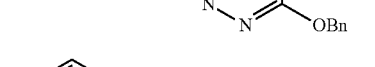 | ESI+: 409 |
| 54 | 2 | 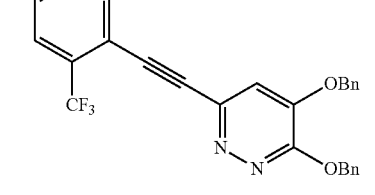 | ESI+: 461 |
TABLE 9-continued
| PEx | PSyn | Str | Data |
|---|---|---|---|
| 55 | 2 | 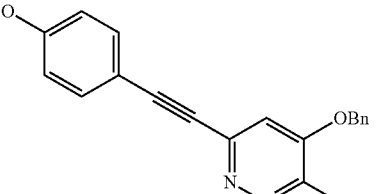 | ESI+: 477 |
| 56 | 2 | 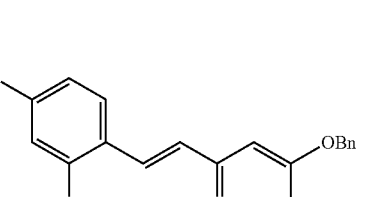 | ESI+: 431 |
| 57 | 3 | 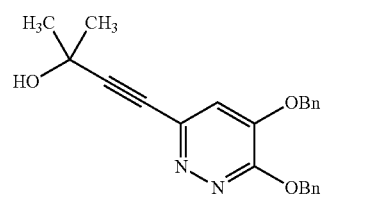 [SMILES: CC(C)(O)C#Cc1cc(OCc2ccccc2)c(OCc2ccccc2)nn1] | ESI+: 375 |
TABLE 10
| PEx | PSyn | Str | Data |
|---|---|---|---|
| 58 | 1 | 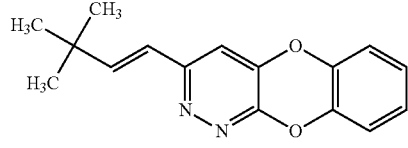 [SMILES: CC(C)(C)/C=C/c1cc2c(nn1)Oc1ccccc1O2] | ESI+: 269 |
| 59 | 1 | 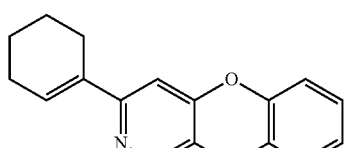 | ESI+: 267 |
| 60 | 1 | 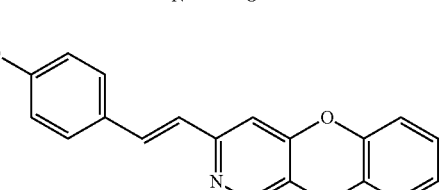 | ESI+: 319 |

TABLE 10-continued

| PEx | PSyn | Str | Data |
|---|---|---|---|
| 61 | 1 | | ESI+: 289 |
| 62 | 13 | | ESI+: 317 |
| 63 | 8 | | ESI/APCI+: 235/237 |
| 64 | 1 | | ESI+: 303 |
| 65 | 1 | | ESI+: 307 |
| 66 | 10 | | ESI+: 343 |

TABLE 11

| PEx | PSyn | Str | Data |
|---|---|---|---|
| 67 | 10 | | ESI+: 311 |
| 68 | 10 | | ESI+: 311 |

TABLE 11-continued

| PEx | PSyn | Str | Data |
|---|---|---|---|
| 69 | 10 | | ESI+: 307 |
| 70 | 10 | | ESI+: 323 |
| 71 | 10 | | ESI+: 323 |
| 72 | 10 | | ESI+: 293 |
| 73 | 10 | | ESI+: 347 |
| 74 | 10 | | ESI+: 363 |

TABLE 12

| PEx | PSyn | Str | Data |
|---|---|---|---|
| 75 | 10 | | ESI+: 307 |

TABLE 12-continued

| PEx | PSyn | Str | Data |
|---|---|---|---|
| 76 | 10 | 4-methylphenyl derivative | ESI+: 307 |
| 77 | 10 | 4-phenylphenyl derivative | ESI+: 369 |
| 78 | 10 | 4-CF3 phenyl derivative | ESI+: 361 |
| 79 | 10 | 3-CF3 phenyl derivative | ESI+: 361 |
| 80 | 10 | 2-CF3 phenyl derivative | ESI+: 361 |
| 81 | 10 | 2,4-difluorophenyl derivative | ESI+: 329 |
| 82 | 10 | 3-OCF3 phenyl derivative | ESI+: 377 |

TABLE 13
| PEx | PSyn | Str | Data |
|---|---|---|---|
| 83 | 10 | 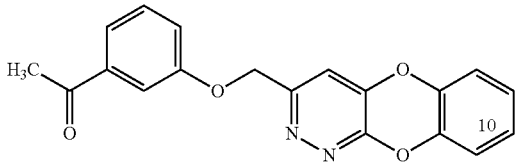 [SMILES: CC(=O)c1cccc(OCc2cc3c(nn2)Oc2ccccc2O3)c1] | ESI+: 335 |
| 84 | 10 | 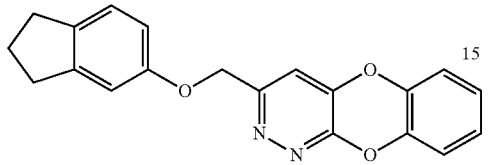 [SMILES: c1ccc2c(c1)Oc1cc(COc3ccc4c(c3)CCC4)nnc1O2] | ESI+: 333 |
| 85 | 10 | 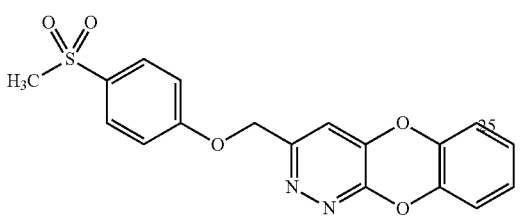 [SMILES: CS(=O)(=O)c1ccc(OCc2cc3c(nn2)Oc2ccccc2O3)cc1] | ESI+: 371 |
| 86 | 10 | 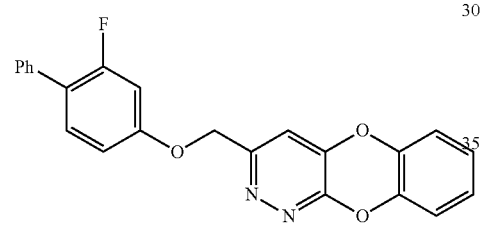 | ESI+: 387 |
| 87 | 10 | 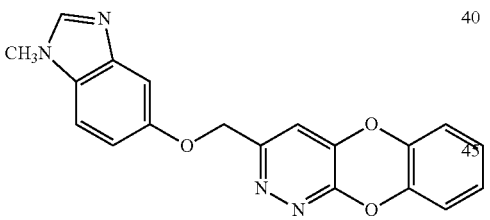 | ESI+: 347 |
| 88 | 10 | 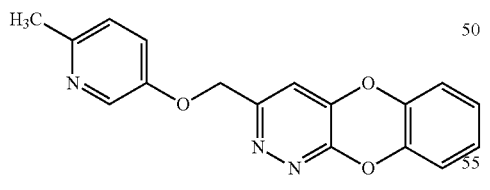 [SMILES: Cc1ccc(OCc2cc3c(nn2)Oc2ccccc2O3)cn1] | ESI+: 308 |
| 89 | 10 | 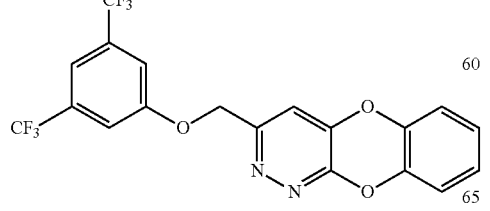 | ESI+: 429 |

TABLE 14
| PEx | PSyn | Str | Data |
|---|---|---|---|
| 90 | 2 |  | ESI+: 449 |
| 91 | 2 | 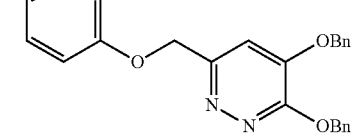 | ESI+: 449 |
| 92 | 2 | 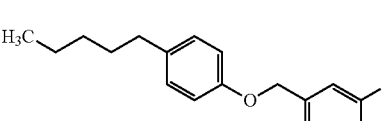 | ESI+: 417 |
| 93 | 2 |  | ESI+: 417 |
| 94 | 2 | 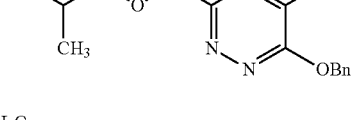 | ESI+: 413 |
| 95 | 2 | 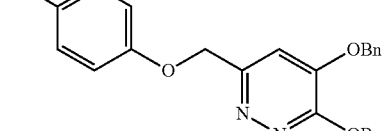 | ESI+: 429 |
| 96 | 2 |  | ESI+: 429 |
| 97 | 2 | 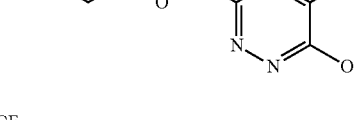 | ESI+: 399 |
TABLE 15
| PEx | PSyn | Str | Data |
|---|---|---|---|
| 98 | 2 | 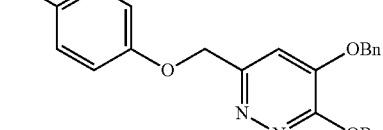 | ESI+: 453 |
| 99 | 2 | 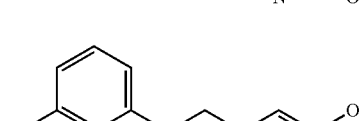 | ESI+: 469 |
| 100 | 2 | 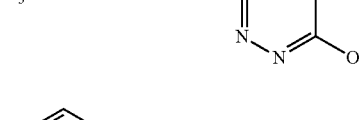 | ESI+: 413 |
| 101 | 2 | 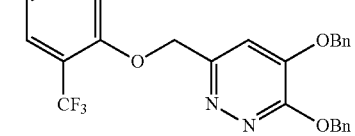 | ESI+: 413 |
| 102 | 2 |  | ESI+: 475 |
| 103 | 2 | | ESI+: 467 |
| 104 | 2 | | ESI+: 467 |
| 105 | 2 | | ESI+: 467 |

TABLE 16

| PEx | PSyn | Str | Data |
|---|---|---|---|
| 106 | 2 | 2,4-difluorophenyl-O-CH2-pyridazine(OBn)(OBn) | ESI+: 435 |
| 107 | 2 | 3-(CF3O)phenyl-O-CH2-pyridazine(OBn)(OBn) | ESI+: 483 |
| 108 | 2 | 3-acetylphenyl-O-CH2-pyridazine(OBn)(OBn) | ESI+: 441 |
| 109 | 2 | indan-5-yl-O-CH2-pyridazine(OBn)(OBn) | ESI+: 439 |
| 110 | 2 | 4-(methylsulfonyl)phenyl-O-CH2-pyridazine(OBn)(OBn) | ESI+: 477 |

TABLE 16-continued

| PEx | PSyn | Str | Data |
|---|---|---|---|
| 111 | 2 | 3-fluoro-4-phenyl-phenyl-O-CH2-pyridazine(OBn)(OBn) | ESI+: 493 |
| 112 | 2 | 1-methyl-1H-benzimidazol-5-yl-O-CH2-pyridazine(OBn)(OBn) | ESI+: 453 |
| 113 | 2 | 6-methylpyridin-3-yl-O-CH2-pyridazine(OBn)(OBn) | ESI+: 414 |

TABLE 17

| PEx | PSyn | Str | Data |
|---|---|---|---|
| 114 | 2 | 3,5-bis(CF3)phenyl-O-CH2-pyridazine(OBn)(OBn) | ESI+: 535 |
| 115 | Syn7 | 6-bromo-2,3-dimethoxypyridine | ESI/APCI+: 218/220 |
| 116 | 1 | ethyl (E)-3-(benzo[b]pyridazino[3,4-e][1,4]dioxin-3-yl)acrylate | ESI/APCI+: 285 |

TABLE 17-continued
| PEx | PSyn | Str | Data |
|---|---|---|---|
| 117 | 1 | 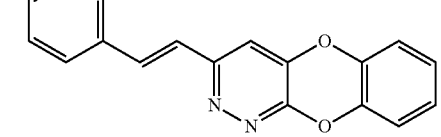 4-CF3-C6H4-CH=CH-[pyridazino-benzodioxin] | ESI+: 357 |
| 118 | 1 | 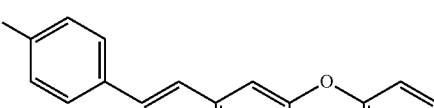 4-CH3-C6H4-CH=CH-[pyridazino-benzodioxin] | ESI+: 303 |
| 119 | 1 | 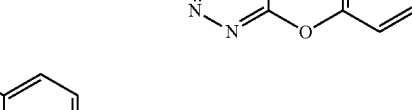 4-Cl-C6H4-CH=CH-[pyridazino-benzodioxin] | ESI+: 323/325 |
| 120 | 2 | 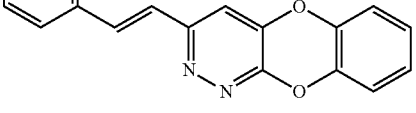 4-Cl-C6H4-CH=CH-pyridazine-4,5-(OBn)2 | ESI+: 429/431 |
| 121 | 1 | 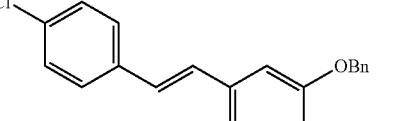 cyclohexyl-CH=CH-[pyridazino-benzodioxin] | ESI+: 295 |
TABLE 18
| Ex | Str |
|---|---|
| 1 | 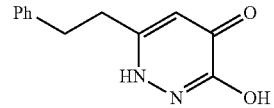 [SMILES: O=c1cc(CCc2ccccc2)[nH]nc1O] |
| 2 | (structure) |
| 3 | (structure) |
| 4 | 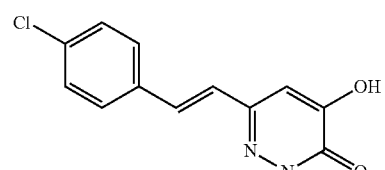 |
| 5 | 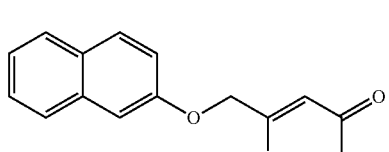 |

TABLE 18-continued

| Ex | Str |
|---|---|
| 6 | 3,5-difluorophenoxymethyl pyridazinone (3,5-F₂-C₆H₃-O-CH₂- substituted pyridazin-3(2H)-one with OH) |
| 7 | 5-chloro-6-bromo-3-hydroxypyridin-2(1H)-one |
| 8 | 5-chloro-3-hydroxy-6-methylpyridin-2(1H)-one |
| 9 | 5-(2-phenylethyl)-3-hydroxypyridin-2(1H)-one |
| 10 | 5-(2-phenylethyl)-3-hydroxy-6-methylpyridin-2(1H)-one |
| 11 | N-(2-(dimethylamino)ethyl)-3-(5-hydroxy-6-oxo-1,6-dihydropyridazin-3-yl)propanamide |
| 12 | 6-(2-(4-(trifluoromethyl)phenyl)ethyl)-5-hydroxypyridazin-3(2H)-one |
| 13 | 6-(2-(4-methylphenyl)ethyl)-5-hydroxypyridazin-3(2H)-one |

TABLE 18-continued

| Ex | Str |
|---|---|
| 14 | 6-(2-(4-methoxyphenyl)ethyl)-5-hydroxypyridazin-3(2H)-one |
| 15 | 6-(2-(4-phenylphenyl)ethyl)-5-hydroxypyridazin-3(2H)-one |
| 16 | 6-(2-(3-methoxyphenyl)ethyl)-5-hydroxypyridazin-3(2H)-one |

TABLE 19

| Ex | Str |
|---|---|
| 17 | 6-(2-(3-(trifluoromethyl)phenyl)ethyl)-5-hydroxypyridazin-3(2H)-one |
| 18 | 6-(2-(3-fluorophenyl)ethyl)-5-hydroxypyridazin-3(2H)-one |
| 19 | 6-(2-(3,5-bis(trifluoromethyl)phenyl)ethyl)-5-hydroxypyridazin-3(2H)-one |
| 20 | 6-(2-(3-methylphenyl)ethyl)-5-hydroxypyridazin-3(2H)-one |

TABLE 19-continued
| Ex | Str |
|---|---|
| 21 | 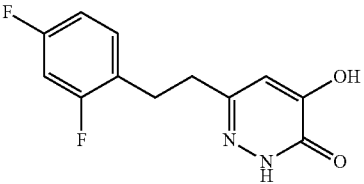 [SMILES: O=c1[nH]nc(CCc2ccc(F)cc2F)cc1O] |
| 22 | 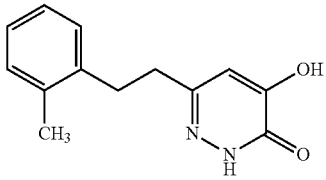 [SMILES: Cc1ccccc1CCc1cc(O)c(=O)[nH]n1] |
| 23 | 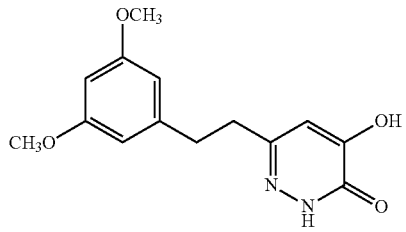 |
| 24 | 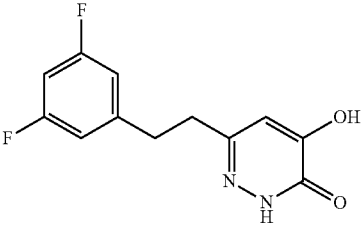 [SMILES: O=c1[nH]nc(CCc2cc(F)cc(F)c2)cc1O] |
| 25 | 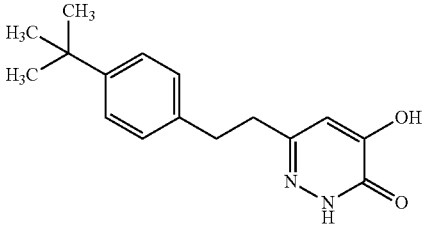 [SMILES: CC(C)(C)c1ccc(CCc2cc(O)c(=O)[nH]n2)cc1] |
| 26 | 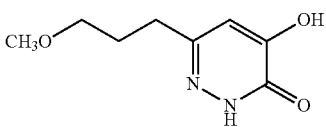 |
| 27 | 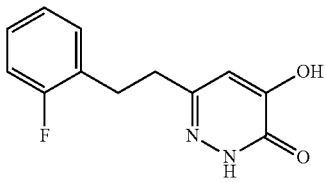 [SMILES: O=c1[nH]nc(CCc2ccccc2F)cc1O] |
| 28 | 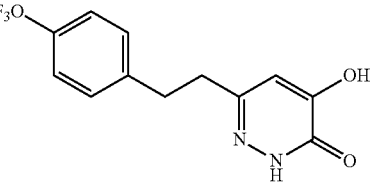 |
| 29 | 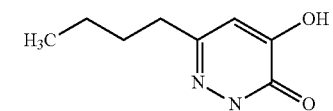 |
| 30 | 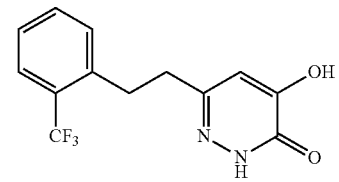 |
| 31 | 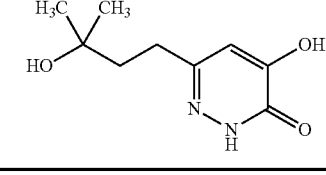 |
TABLE 20
| Ex | Str |
|---|---|
| 32 | 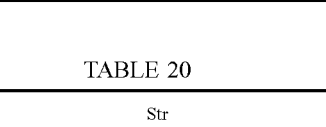 |
| 33 | 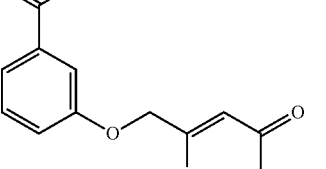 |
| 34 | 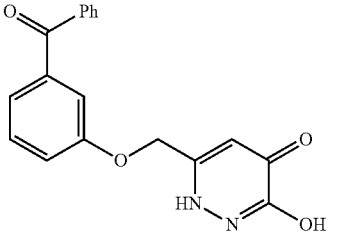 [SMILES: O=C(c1ccccc1)c1cccc(OCc2cc(=O)c(O)n[nH]2)c1] |

TABLE 20-continued
| Ex | Str |
|---|---|
| 35 | 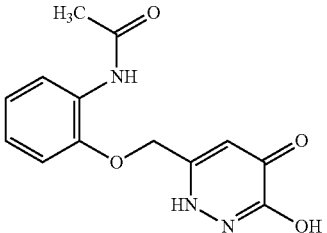 [SMILES: CC(=O)Nc1ccccc1OCc1cc(=O)c(O)n[nH]1] |
| 36 | 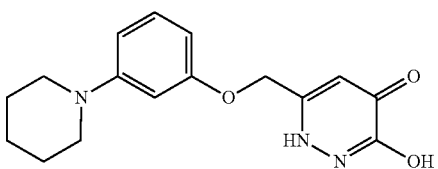 [SMILES: O=c1cc(COc2cccc(N3CCCCC3)c2)[nH]nc1O] |
| 37 | 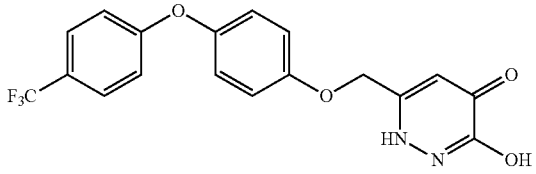 [SMILES: O=c1cc(COc2ccc(Oc3ccc(C(F)(F)F)cc3)cc2)[nH]nc1O] |
| 38 | 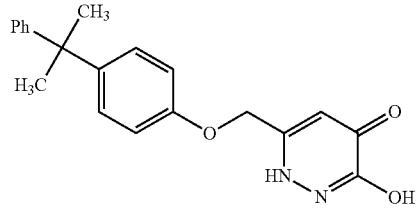 [SMILES: CC(C)(c1ccccc1)c1ccc(OCc2cc(=O)c(O)n[nH]2)cc1] |
| 39 | 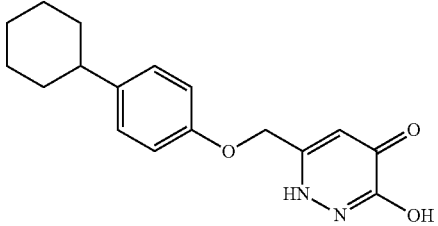 [SMILES: O=c1cc(COc2ccc(C3CCCCC3)cc2)[nH]nc1O] |
| 40 | 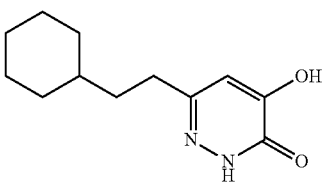 [SMILES: O=c1[nH]nc(CCC2CCCCC2)cc1O] |
| 41 | 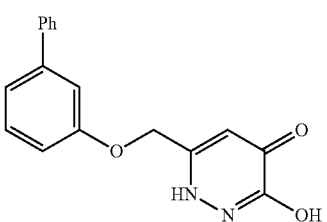 [SMILES: O=c1cc(COc2cccc(-c3ccccc3)c2)[nH]nc1O] |
TABLE 20-continued
| Ex | Str |
|---|---|
| 42 | 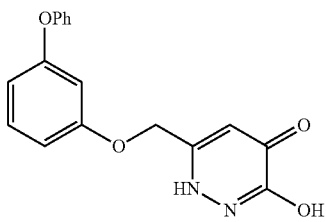 [SMILES: O=c1cc(COc2cccc(Oc3ccccc3)c2)[nH]nc1O] |
| 43 | 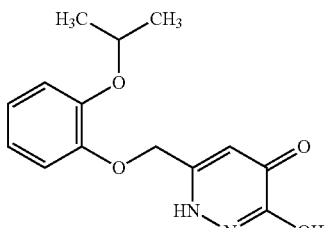 |
| 44 | 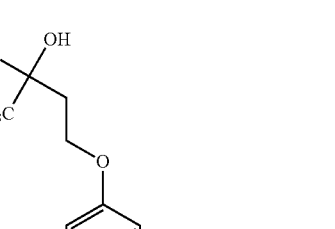 |
TABLE 21
| Ex | Str |
|---|---|
| 45 | 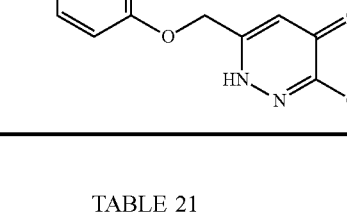 |
| 46 | 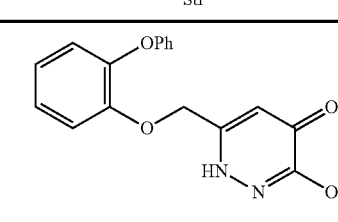 |

TABLE 21-continued
| Ex | Str |
|---|---|
| 47 | 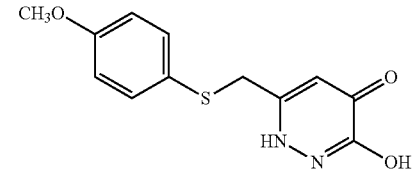 |
| 48 | 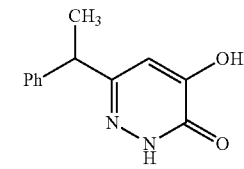 [SMILES: CC(c1ccccc1)c1cc(O)c(=O)[nH]n1] |
| 49 | 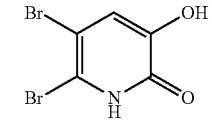 |
| 50 | 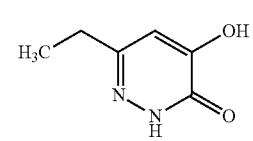 |
| 51 | 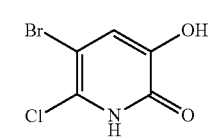 |
| 52 | 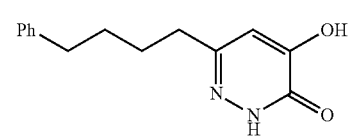 [SMILES: O=c1[nH]nc(CCCCc2ccccc2)cc1O] |
| 53 | 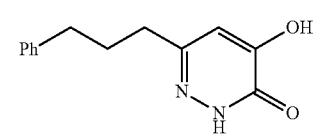 [SMILES: O=c1[nH]nc(CCCc2ccccc2)cc1O] |
| 54 | 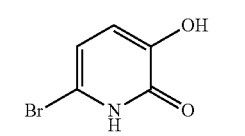 |
| 55 | 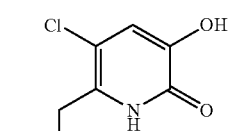 |
| 56 | 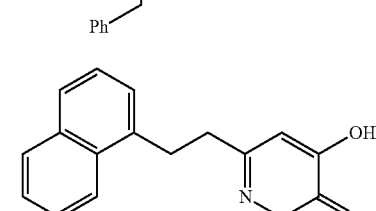 |
TABLE 21-continued
| Ex | Str |
|---|---|
| 57 | 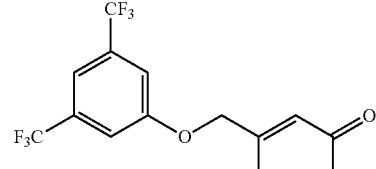 |
| 58 | 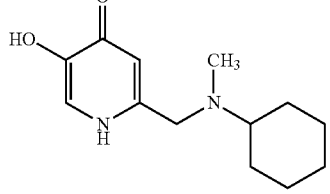 |
| 59 | 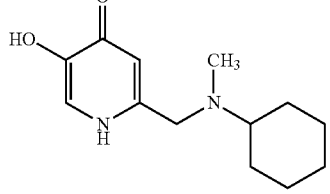 |
| 60 | 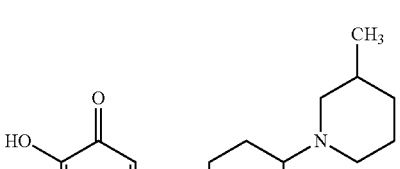 |
TABLE 22
| Ex | Str |
|---|---|
| 61 | 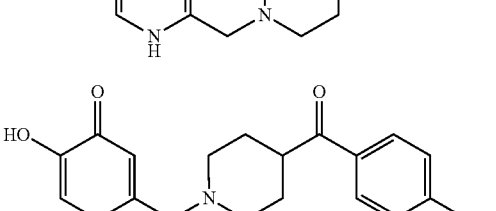 |
| 62 | |
| 63 | |

TABLE 22-continued

| Ex | Str |
|---|---|
| 64 | 5-hydroxy-2-{[3-(pyrimidin-2-yl)pyrrolidin-1-yl]methyl}pyridin-4(1H)-one |
| 65 | 2-{[4-(4-methylpiperidin-1-yl)piperidin-1-yl]methyl}-5-hydroxypyridin-4(1H)-one |
| 66 | 5-hydroxy-2-{[4-(trifluoromethyl)piperidin-1-yl]methyl}pyridin-4(1H)-one |
| 67 | 2-{[4-(adamantan-1-yl)piperazin-1-yl]methyl}-5-hydroxypyridin-4(1H)-one |
| 68 | 5-hydroxy-2-{[4-(methanesulfonyl)piperazin-1-yl]methyl}pyridin-4(1H)-one |
| 69 | 2-{[(cyclopropylmethyl)(propyl)amino]methyl}-5-hydroxypyridin-4(1H)-one |
| 70 | 2-{[(1-ethyl-1H-pyrazol-4-yl)methyl](methyl)amino]methyl}-5-hydroxypyridin-4(1H)-one |
| 71 | 2-{[4-(3,4-difluorobenzoyl)piperidin-1-yl]methyl}-5-hydroxypyridin-4(1H)-one |

TABLE 22-continued

| Ex | Str |
|---|---|
| 72 | 5-hydroxy-2-{[4-(5-phenyl-1,3,4-oxadiazol-2-yl)piperidin-1-yl]methyl}pyridin-4(1H)-one |
| 73 | 5-hydroxy-2-[(4,4-dimethylpiperidin-1-yl)methyl]pyridin-4(1H)-one |
| 74 | 5-hydroxy-2-{[4-(morpholin-4-yl)piperidin-1-yl]methyl}pyridin-4(1H)-one |
| 75 | 5-hydroxy-2-{[3-(pyridin-2-yloxy)piperidin-1-yl]methyl}pyridin-4(1H)-one |

TABLE 23

| Ex | Str |
|---|---|
| 76 | 2-{[4-benzoylpiperidin-1-yl]methyl}-5-hydroxypyridin-4(1H)-one |
| 77 | 5-hydroxy-2-{[4-(2-oxo-2,3-dihydro-1H-benzimidazol-1-yl)piperidin-1-yl]methyl}pyridin-4(1H)-one |
| 78 | 2-{[4-(4-fluorobenzoyl)piperidin-1-yl]methyl}-5-hydroxypyridin-4(1H)-one |

TABLE 23-continued
| Ex | Str |
|---|---|
| 79 | 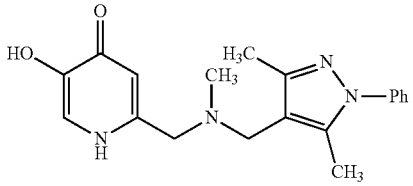 [SMILES: Cc1nn(-c2ccccc2)c(C)c1CN(C)Cc1cc(=O)c(O)c[nH]1] |
| 80 | 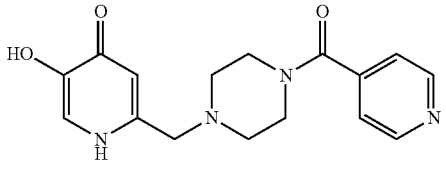 [SMILES: O=C(c1ccncc1)N1CCN(Cc2cc(=O)c(O)c[nH]2)CC1] |
| 81 | 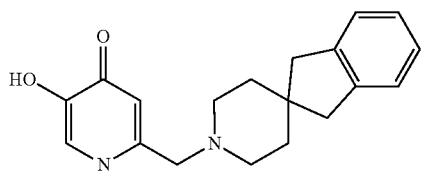 |
| 82 | 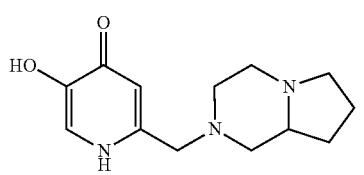 [SMILES: O=c1cc(CN2CCN3CCCC3C2)[nH]cc1O] |
| 83 | 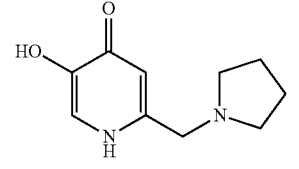 [SMILES: O=c1cc(CN2CCCC2)[nH]cc1O] |
| 84 | 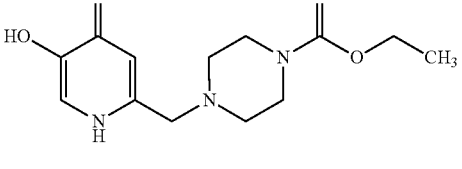 |
| 85 | 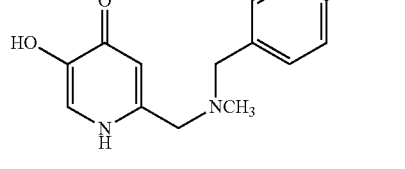 |
| 86 | 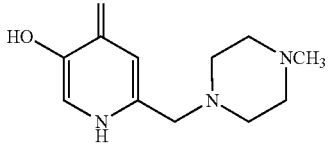 |
| 87 | 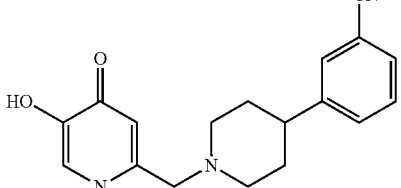 |
| 88 | 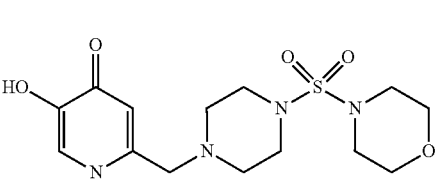 |
| 89 | 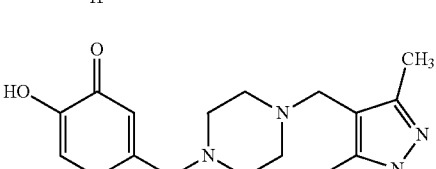 |
| 90 | 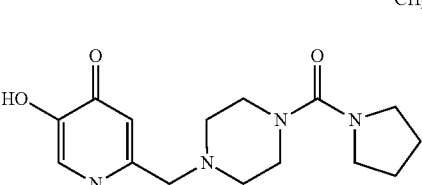 |
| 91 | 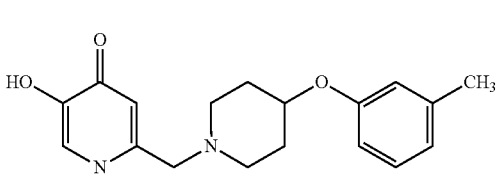 |
TABLE 24
| Ex | Str |
|---|---|
| 92 | 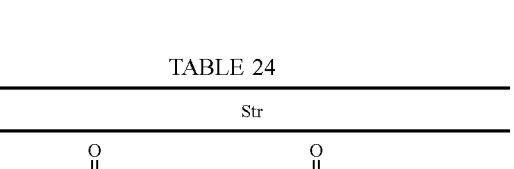 |
| 93 | 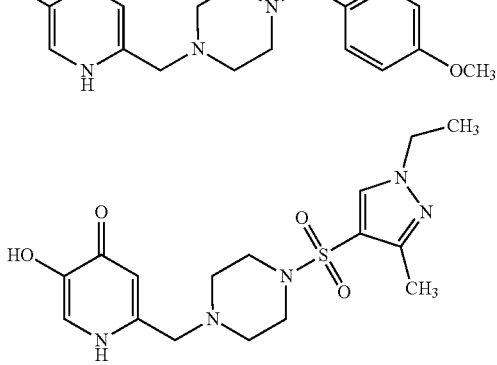 |

TABLE 24-continued
| Ex | Str |
|---|---|
| 94 | 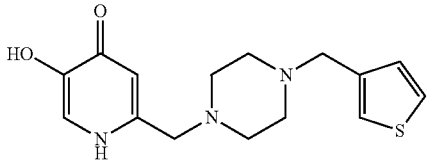 [SMILES: O=c1cc(CN2CCN(Cc3ccsc3)CC2)[nH]cc1O] |
| 95 | 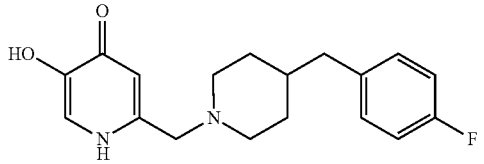 [SMILES: O=c1cc(CN2CCC(Cc3ccc(F)cc3)CC2)[nH]cc1O] |
| 96 | 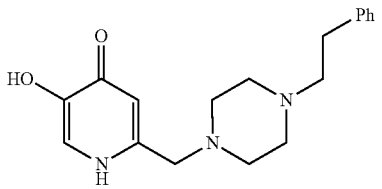 [SMILES: O=c1cc(CN2CCN(CCc3ccccc3)CC2)[nH]cc1O] |
| 97 | 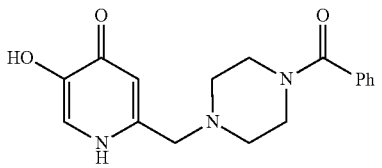 [SMILES: O=C(c1ccccc1)N1CCN(Cc2cc(=O)c(O)c[nH]2)CC1] |
| 98 | 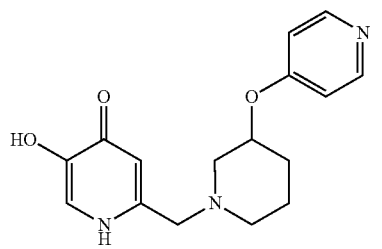 [SMILES: O=c1cc(CN2CCCC(Oc3ccncc3)C2)[nH]cc1O] |
| 99 | 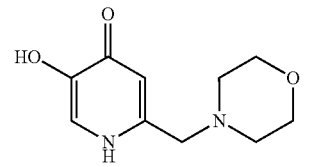 [SMILES: O=c1cc(CN2CCOCC2)[nH]cc1O] |
| 100 | 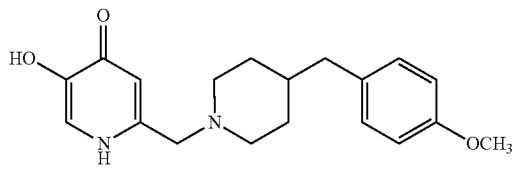 [SMILES: COc1ccc(CC2CCN(Cc3cc(=O)c(O)c[nH]3)CC2)cc1] |
| 101 | 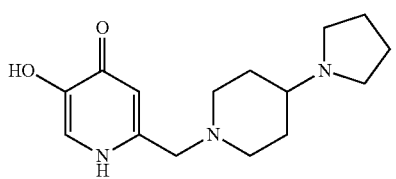 [SMILES: O=c1cc(CN2CCC(N3CCCC3)CC2)[nH]cc1O] |
TABLE 24-continued
| Ex | Str |
|---|---|
| 102 | 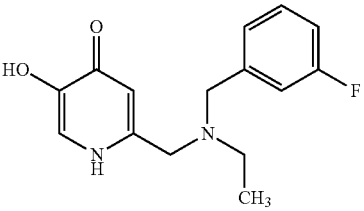 [SMILES: CCN(Cc1cccc(F)c1)Cc1cc(=O)c(O)c[nH]1] |
| 103 | 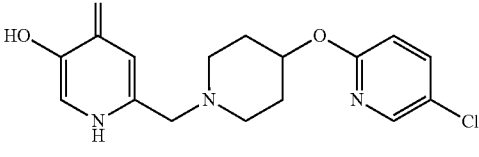 |
| 104 | 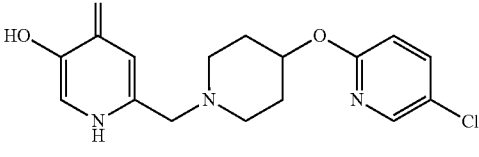 |
| 105 | 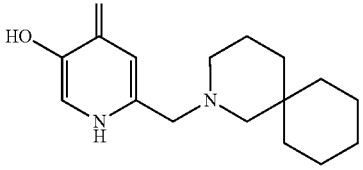 |
| 106 | 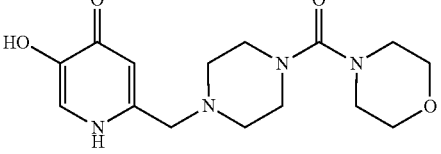 |
TABLE 25
| Ex | Str |
|---|---|
| 107 | 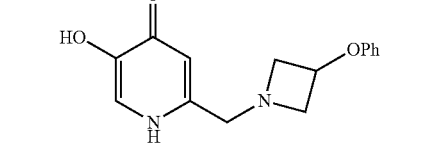 |
| 108 | 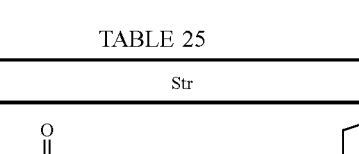 |
| 109 | 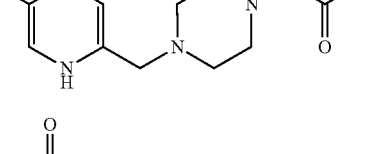 |

TABLE 25-continued
| Ex | Str |
|---|---|
| 110 | 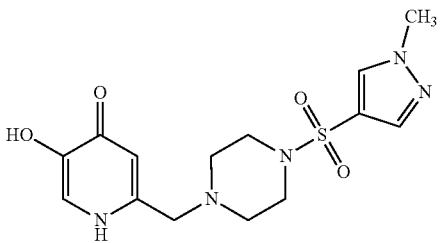 [SMILES: Cn1cc(S(=O)(=O)N2CCN(Cc3cc(=O)c(O)c[nH]3)CC2)cn1] |
| 111 | 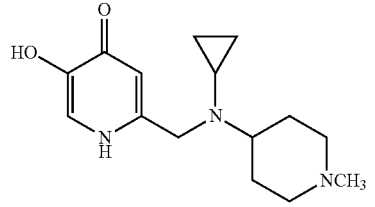 [SMILES: CN1CCC(N(Cc2cc(=O)c(O)c[nH]2)C2CC2)CC1] |
| 112 | 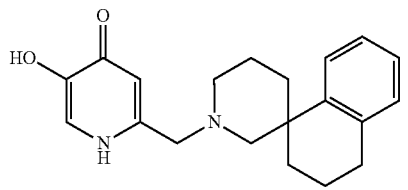 [SMILES: O=c1cc(CN2CCCC3(CCCc4ccccc43)C2)[nH]cc1O] |
| 113 | 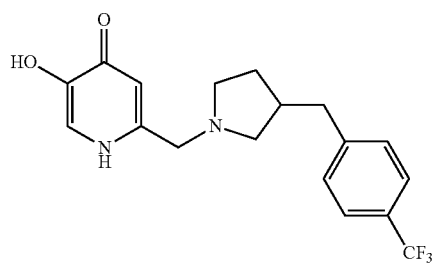 [SMILES: O=c1cc(CN2CCC(Cc3ccc(C(F)(F)F)cc3)C2)[nH]cc1O] |
| 114 | 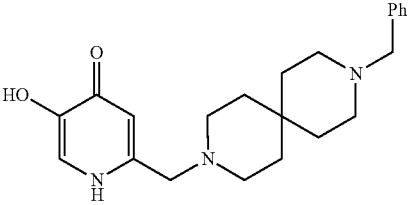 [SMILES: O=c1cc(CN2CCC3(CCN(Cc4ccccc4)CC3)CC2)[nH]cc1O] |
| 115 | 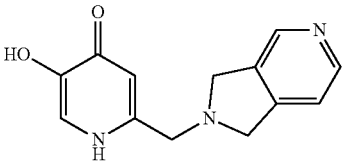 [SMILES: O=c1cc(CN2Cc3ccncc3C2)[nH]cc1O] |
| 116 | 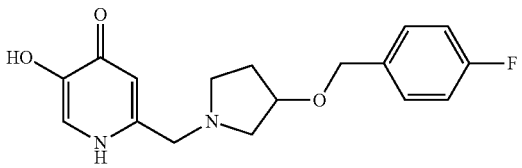 [SMILES: O=c1cc(CN2CCC(OCc3ccc(F)cc3)C2)[nH]cc1O] |
TABLE 25-continued
| Ex | Str |
|---|---|
| 117 | 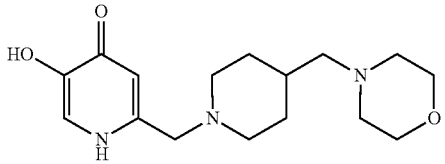 [SMILES: O=c1cc(CN2CCC(CN3CCOCC3)CC2)[nH]cc1O] |
| 118 | 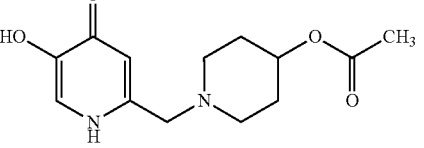 |
| 119 | 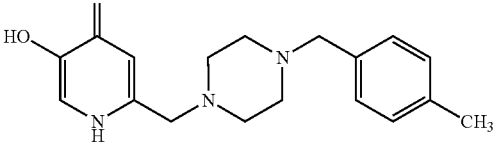 |
| 120 | 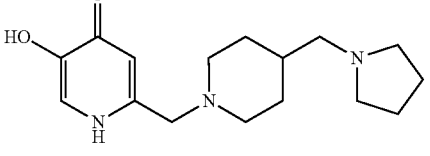 |
| 121 | 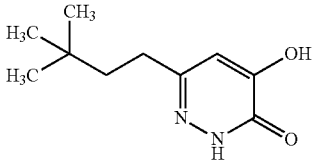 |
TABLE 26
| Ex | Str |
|---|---|
| 122 | 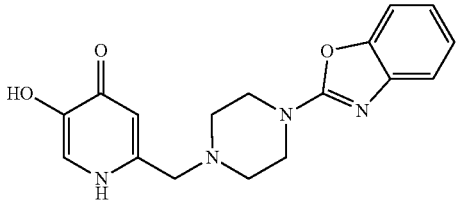 [SMILES: O=c1cc(CN2CCN(c3nc4ccccc4o3)CC2)[nH]cc1O] |
| 123 | 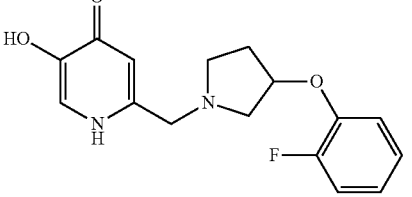 |

US 10,202,399 B2
TABLE 26-continued
| Ex | Str |
|---|---|
| 124 | 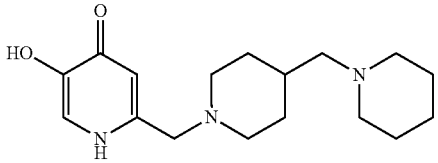 [SMILES: O=c1cc(CN2CCC(CN3CCCCC3)CC2)[nH]cc1O] |
| 125 | 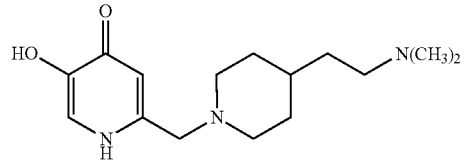 [SMILES: CN(C)CCC1CCN(Cc2cc(=O)c(O)c[nH]2)CC1] |
| 126 | 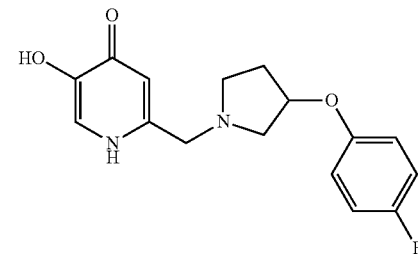 [SMILES: O=c1cc(CN2CCC(Oc3ccc(F)cc3)C2)[nH]cc1O] |
| 127 | 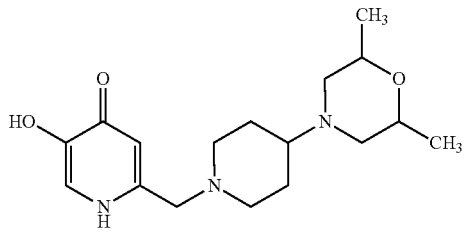 [SMILES: CC1CN(C2CCN(Cc3cc(=O)c(O)c[nH]3)CC2)CC(C)O1] |
| 128 | 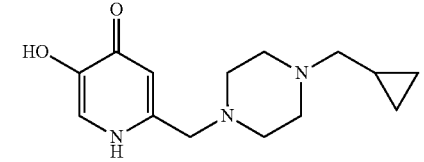 [SMILES: O=c1cc(CN2CCN(CC3CC3)CC2)[nH]cc1O] |
| 129 | 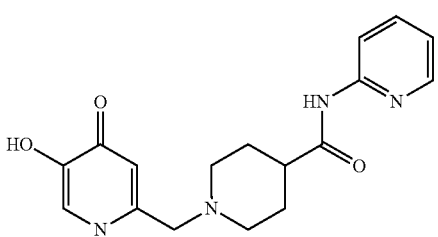 |
| 130 | 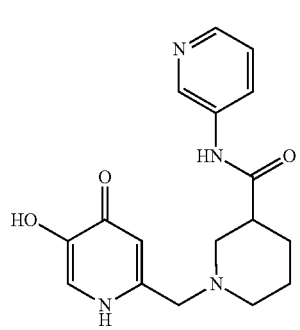 [SMILES: O=C(Nc1cccnc1)C1CCCN(Cc2cc(=O)c(O)c[nH]2)C1] |
TABLE 26-continued
| Ex | Str |
|---|---|
| 131 | 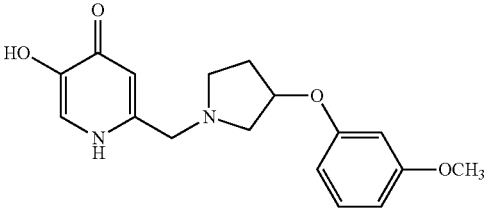 [SMILES: COc1cccc(OC2CCN(Cc3cc(=O)c(O)c[nH]3)C2)c1] |
| 132 | 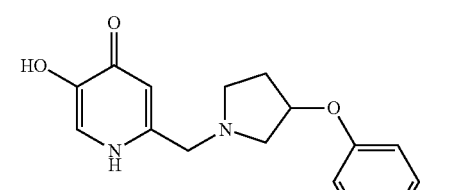 |
| 133 | 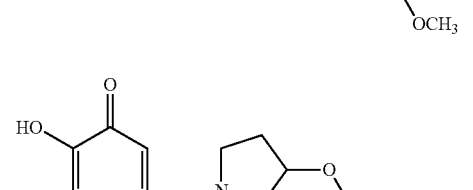 |
| 134 | 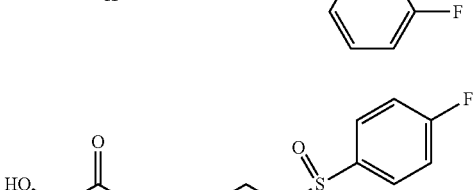 |
TABLE 27
| Ex | Str |
|---|---|
| 135 | 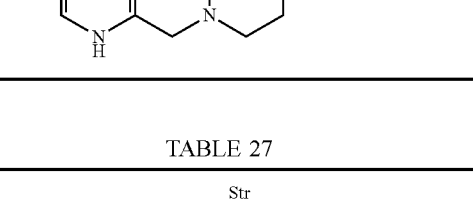 |
| 136 | 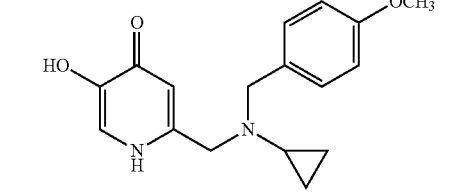 |

TABLE 27-continued
| Ex | Str |
|---|---|
| 137 | 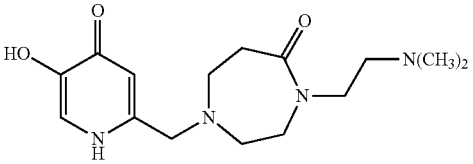 [SMILES: CN(C)CCN1CCN(Cc2cc(=O)c(O)c[nH]2)CCC1=O] |
| 138 | 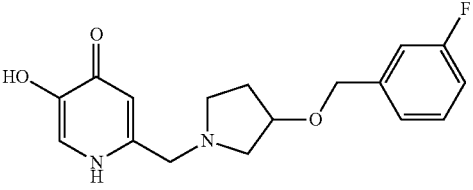 [SMILES: O=c1cc(CN2CCC(OCc3cccc(F)c3)C2)[nH]cc1O] |
| 139 | 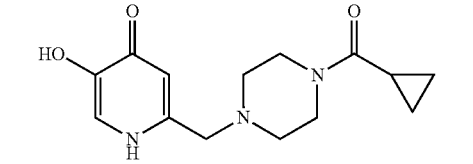 [SMILES: O=C(C1CC1)N1CCN(Cc2cc(=O)c(O)c[nH]2)CC1] |
| 140 | 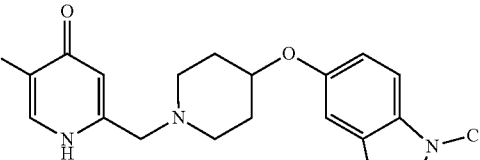 |
| 141 | 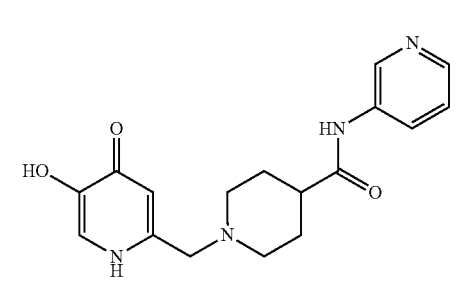 [SMILES: O=C(Nc1cccnc1)C1CCN(Cc2cc(=O)c(O)c[nH]2)CC1] |
| 142 | 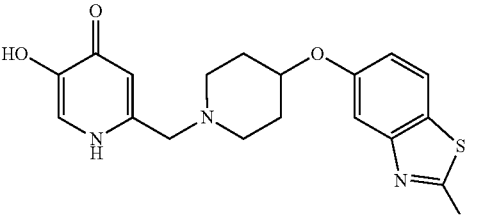 |
| 143 | 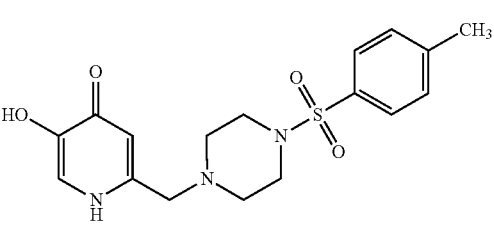 [SMILES: Cc1ccc(S(=O)(=O)N2CCN(Cc3cc(=O)c(O)c[nH]3)CC2)cc1] |
TABLE 27-continued
| Ex | Str |
|---|---|
| 144 | 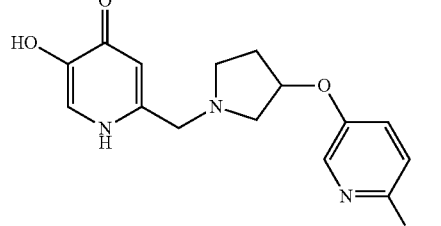 |
| 145 | 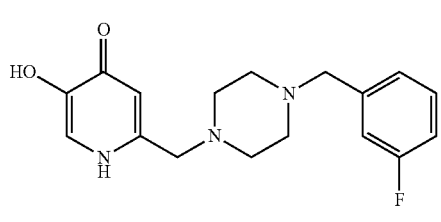 [SMILES: O=c1cc(CN2CCN(Cc3cccc(F)c3)CC2)[nH]cc1O] |
| 146 |  |
| 147 |  |
TABLE 28
| Ex | Str |
|---|---|
| 148 | 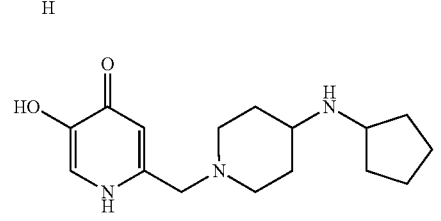 |
| 149 |  |

TABLE 28-continued

| Ex | Str |
|---|---|
| 150 | (structure) |
| 151 | (structure) |
| 152 | (structure) |
| 153 | (structure) |
| 154 | (structure) |
| 155 | (structure) |
| 156 | (structure) |
| 157 | (structure) |
| 158 | (structure) |
| 159 | (structure) |

TABLE 29

| Ex | Str |
|---|---|
| 160 | (structure) |
| 161 | (structure) |
| 162 | (structure) |

TABLE 29-continued
| Ex | Str |
|---|---|
| 163 | 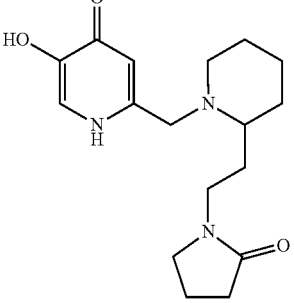 |
| 164 | 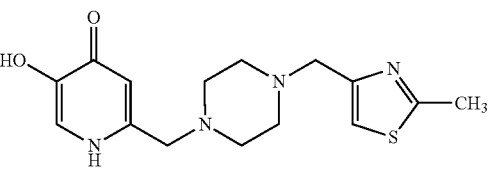 [SMILES: Cc1nc(CN2CCN(Cc3cc(=O)c(O)c[nH]3)CC2)cs1] |
| 165 | 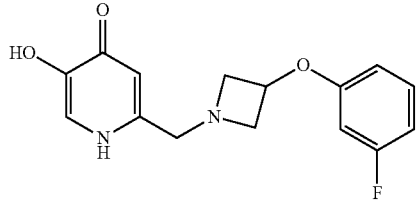 [SMILES: O=c1cc(CN2CC(Oc3cccc(F)c3)C2)[nH]cc1O] |
| 166 | 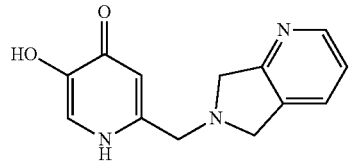 [SMILES: O=c1cc(CN2Cc3cccnc3C2)[nH]cc1O] |
| 167 | 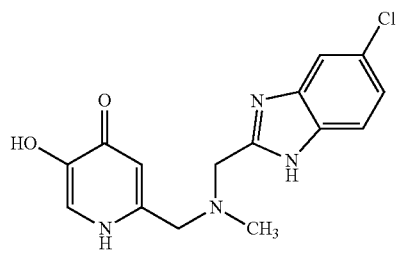 [SMILES: CN(Cc1cc(=O)c(O)c[nH]1)Cc1nc2cc(Cl)ccc2[nH]1] |
| 168 | 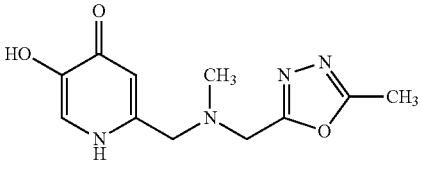 [SMILES: Cc1nnc(CN(C)Cc2cc(=O)c(O)c[nH]2)o1] |
| 169 | 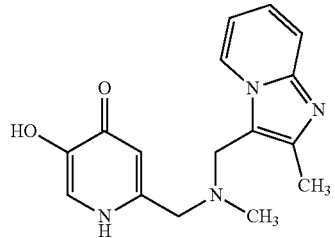 [SMILES: Cc1nc2ccccn2c1CN(C)Cc1cc(=O)c(O)c[nH]1] |
TABLE 29-continued
| Ex | Str |
|---|---|
| 170 | 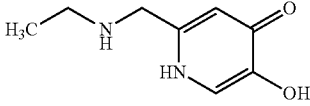 |
| 171 | 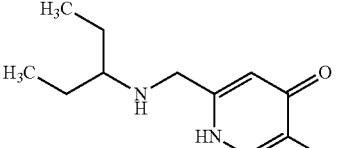 |
| 172 | 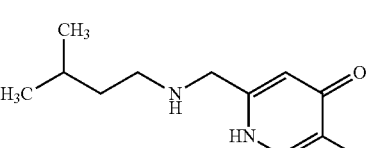 |
| 173 | 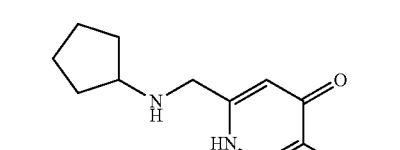 |
| 174 | 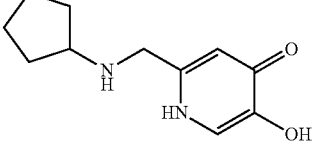 |
TABLE 30
| Ex | Str |
|---|---|
| 175 | 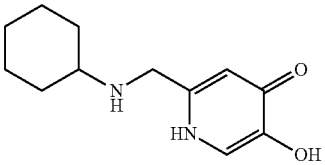 [SMILES: O=c1cc(CNC2CCCCC2)[nH]cc1O] |
| 176 | 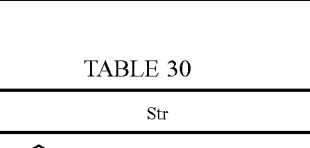 |
| 177 | 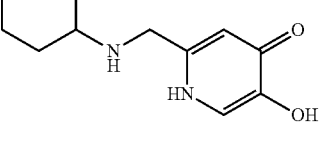 |

TABLE 30-continued

| Ex | Str |
|---|---|
| 178 | 1-hydroxyadamantyl-NH-CH2-(5-hydroxy-4-oxo-1H-pyridin-2-yl) |
| 179 | cyclohexyl-CH2-NH-CH2-(5-hydroxy-4-oxo-1H-pyridin-2-yl) |
| 180 | (1-methylpiperidin-2-yl)-CH2-NH-CH2-(5-hydroxy-4-oxo-1H-pyridin-2-yl) |
| 181 | (2-oxopyrrolidin-1-yl)-(CH2)3-NH-CH2-(5-hydroxy-4-oxo-1H-pyridin-2-yl) |
| 182 | 2-Br-C6H4-S-CH2-(5-hydroxy-4-oxo-1H-pyridin-2-yl) |
| 183 | 2,5-diCl-C6H3-S-CH2-(5-hydroxy-4-oxo-1H-pyridin-2-yl) |
| 184 | 2,6-diCl-C6H3-S-CH2-(5-hydroxy-4-oxo-1H-pyridin-2-yl) |
| 185 | 2-iPr-C6H4-S-CH2-(5-hydroxy-4-oxo-1H-pyridin-2-yl) |
| 186 | 3-CH3-C6H4-S-CH2-(5-hydroxy-4-oxo-1H-pyridin-2-yl) |
| 187 | 4-F-C6H4-S-CH2-(5-hydroxy-4-oxo-1H-pyridin-2-yl) |
| 188 | 4-(CH3C(O)NH)-C6H4-S-CH2-(5-hydroxy-4-oxo-1H-pyridin-2-yl) |
| 189 | 4-CH3O-C6H4-S-CH2-(5-hydroxy-4-oxo-1H-pyridin-2-yl) |
| 190 | 2,5-diMe-C6H3-S-CH2-(5-hydroxy-4-oxo-1H-pyridin-2-yl) |
| 191 | 2,6-diMe-C6H3-S-CH2-(5-hydroxy-4-oxo-1H-pyridin-2-yl) |

TABLE 31

| Ex | Str |
|---|---|
| 192 | 4-tBu-C6H4-S-CH2-(5-hydroxy-4-oxo-1H-pyridin-2-yl) |
| 193 | 3,5-diMe-C6H3-S-CH2-(5-hydroxy-4-oxo-1H-pyridin-2-yl) |

TABLE 31-continued

| Ex | Str |
|---|---|
| 194 | 3-(trifluoromethyl)phenyl-S-CH2-(4-oxo-5-hydroxy-1H-pyridin-2-yl) |
| 195 | 2-fluorophenyl-S-CH2-(4-oxo-5-hydroxy-1H-pyridin-2-yl) |
| 196 | 2,3-dichlorophenyl-S-CH2-(4-oxo-5-hydroxy-1H-pyridin-2-yl) |
| 197 | 2,4-dichlorophenyl-S-CH2-(4-oxo-5-hydroxy-1H-pyridin-2-yl) |
| 198 | 2-chloro-6-methylphenyl-S-CH2-(4-oxo-5-hydroxy-1H-pyridin-2-yl) |
| 199 | 3-chloro-4-fluorophenyl-S-CH2-(4-oxo-5-hydroxy-1H-pyridin-2-yl) |
| 200 | 2-(methoxycarbonyl)phenyl-S-CH2-(4-oxo-5-hydroxy-1H-pyridin-2-yl) |
| 201 | 4-(methylthio)phenyl-S-CH2-(4-oxo-5-hydroxy-1H-pyridin-2-yl) |

TABLE 31-continued

| Ex | Str |
|---|---|
| 202 | 2-methyl-5-tert-butylphenyl-S-CH2-(4-oxo-5-hydroxy-1H-pyridin-2-yl) |
| 203 | 4-bromo-2-(trifluoromethoxy)phenyl-S-CH2-(4-oxo-5-hydroxy-1H-pyridin-2-yl) |
| 204 | 2,4-difluorophenyl-S-CH2-(4-oxo-5-hydroxy-1H-pyridin-2-yl) |
| 205 | 4-(methoxycarbonyl)phenyl-S-CH2-(4-oxo-5-hydroxy-1H-pyridin-2-yl) |
| 206 | 4-bromophenyl-S-CH2-(4-oxo-5-hydroxy-1H-pyridin-2-yl) |
| 207 | 4-fluoro-2-(hydroxymethyl)phenyl-S-CH2-(4-oxo-5-hydroxy-1H-pyridin-2-yl) |

TABLE 32

| Ex | Str |
|---|---|
| 208 | 3-(trifluoromethoxy)phenyl-S-CH2-(4-oxo-5-hydroxy-1H-pyridin-2-yl) |

TABLE 32-continued

| Ex | Str |
|---|---|
| 209 | (2-ethylphenyl-S-CH2-)(5-hydroxy-pyridin-4(1H)-one) |
| 210 | (3-methoxyphenyl-S-CH2-)(5-hydroxy-pyridin-4(1H)-one) |
| 211 | (3-ethoxyphenyl-S-CH2-)(5-hydroxy-pyridin-4(1H)-one) |
| 212 | (4-fluorophenethyl)(5-hydroxy-6-oxo-1,6-dihydropyridazin-3-yl) |
| 213 | (CH3)2N-CH2CH2-N(CH3)-C(O)-CH2CH2-(5-hydroxy-6-oxo-1,6-dihydropyridazin-3-yl) |
| 214 | HN(C(O)-CH2CH2-(5-hydroxy-6-oxo-1,6-dihydropyridazin-3-yl))-CH2CH2CH2-N(CH3)2 |
| 215 | H3C-N(CH3)-C(O)-CH2CH2-(5-hydroxy-6-oxo-1,6-dihydropyridazin-3-yl); N-CH2CH2CH2-N(CH3)2 |
| 216 | (1-methylpiperidin-4-yl)-CH2-NH-C(O)-CH2CH2-(5-hydroxy-6-oxo-1,6-dihydropyridazin-3-yl) |

TABLE 32-continued

| Ex | Str |
|---|---|
| 217 | (pyridin-3-yl-CH2-NH-C(O)-CH2CH2-)(5-hydroxy-6-oxo-1,6-dihydropyridazin-3-yl) |
| 218 | (1H-imidazol-1-yl-CH2CH2CH2-NH-C(O)-CH2CH2-)(5-hydroxy-6-oxo-1,6-dihydropyridazin-3-yl) |
| 219 | (3-(dimethylamino)pyrrolidin-1-yl)-C(O)-CH2CH2-(5-hydroxy-6-oxo-1,6-dihydropyridazin-3-yl) |
| 220 | (4-(dimethylamino)piperidin-1-yl)-C(O)-CH2CH2-(5-hydroxy-6-oxo-1,6-dihydropyridazin-3-yl) |
| 221 | (4-methylpiperazin-1-yl)-C(O)-CH2CH2-(5-hydroxy-6-oxo-1,6-dihydropyridazin-3-yl) |
| 222 | (4-(2-methoxyethyl)piperazin-1-yl)-C(O)-CH2CH2-(5-hydroxy-6-oxo-1,6-dihydropyridazin-3-yl) |

TABLE 33

| Ex | Str |
|---|---|
| 223 | (4-(3-methoxypropyl)piperazin-1-yl)-C(O)-CH2CH2-(5-hydroxy-6-oxo-1,6-dihydropyridazin-3-yl) |

TABLE 33-continued
| Ex | Str |
|---|---|
| 224 |  |
| 225 | 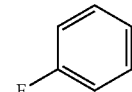 |
| 226 |  |
| 227 | 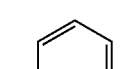 |
| 228 | 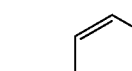 |
| 229 | 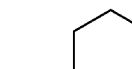 |
| 230 | 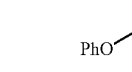 |
| 231 | 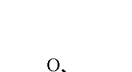 |
| 232 | |
| 233 | |
| 234 | |
| 235 | |
| 236 | |
| 237 | |
| 238 | |

TABLE 34
| Ex | Str |
|---|---|
| 239 | 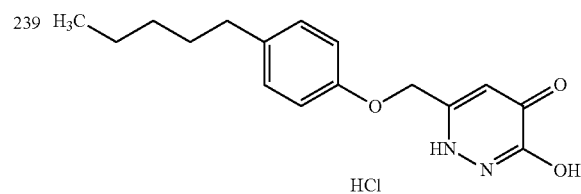 HCl |
| 240 | 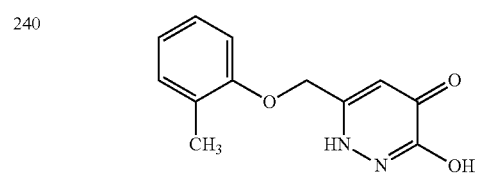 |
| 241 | 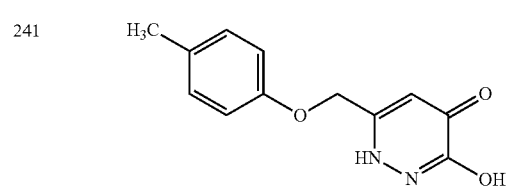 |
| 242 | 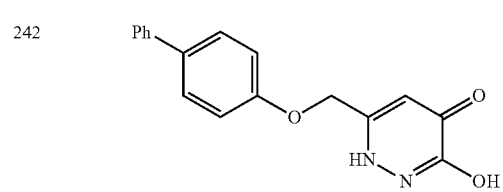 |
| 243 | 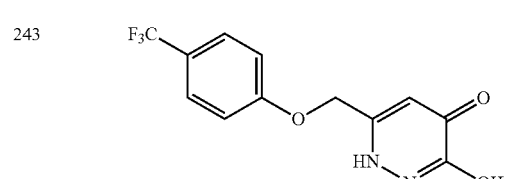 |
| 244 | 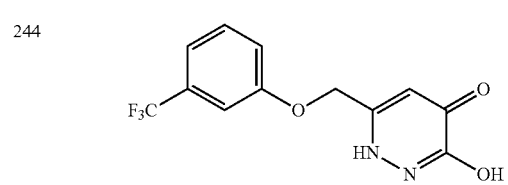 |
| 245 | 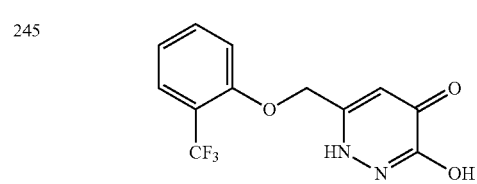 |
| 246 | 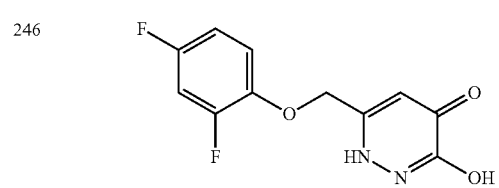 |
TABLE 34-continued
| Ex | Str |
|---|---|
| 247 | 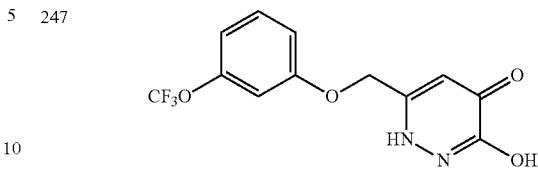 |
| 248 | 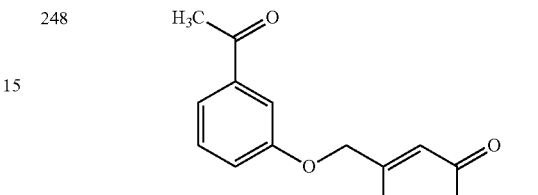 |
| 249 | 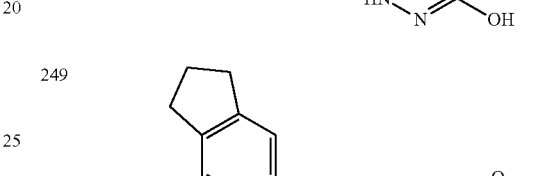 |
| 250 | 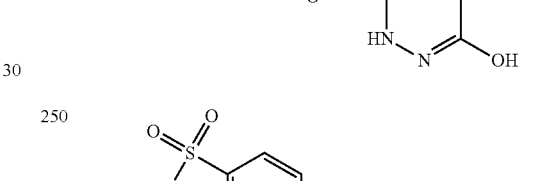 |
| 251 | 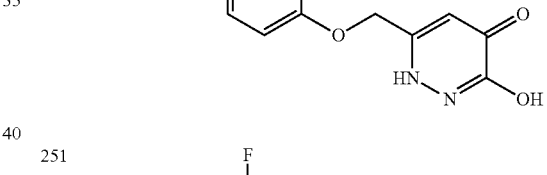 |
| 252 | 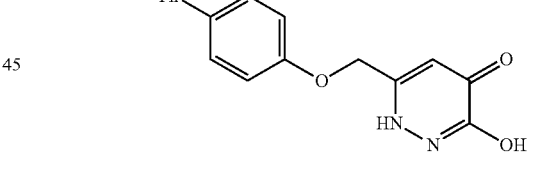 |
| 253 | 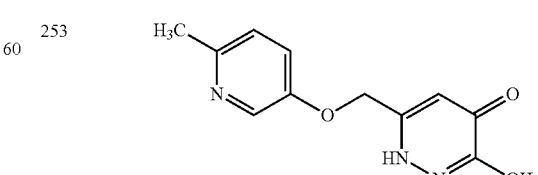 |

TABLE 34-continued

| Ex | Str |
|---|---|
| 254 | 4-chlorophenoxymethyl-5-hydroxy-pyridazin-3(2H)-one structure |

TABLE 35

| Ex | Syn | Data |
|---|---|---|
| 1 | 1 | NMR1: 2.73-2.77 (m, 2H), 2.85-2.89 (m, 2H), 6.57 (s, 1H), 7.15-7.29 (m, 5H), 12.7 (s, 1H)<br>ESI+: 217 |
| 2 | 2 | NMR1; 7.00 (d, J = 16.8 Hz, 1H), 7.11 (s, 1H), 7.28 (d, J = 16.8 Hz, 1H), 7.44 (d, J = 8.0 Hz, 2H), 7.64 (d, J = 8.0 Hz, 2H), 10.90 (s, 1H), 13.00 (s, 1H)<br>FAB+: 249/251 |
| 3 | 3 | NMR1: 5.00 (s, 2H), 6.72 (s, 1H), 7.21-7.24 (m, 1H), 7.34-7.49 (m, 3H), 7.78-7.86 (m, 3H), 12.92 (brs, 1H)<br>ESI+: 269 |
| 4 | 4 | ESI+: 237 |
| 5 | 5 | ESI+: 308 |
| 6 | 6 | NMR1: 4.92 (s, 2H), 6.67 (s, 1H), 6.79-6.84 (m, 3H), 12.97 (s, 1H)<br>ESI+: 255 |
| 7 | 7 | NMR1; 7.28 (s, 1H), 10.40 (brs, 1H), 12.15 (brs, 1H)<br>ESI/APCI+: 224/226/228 |
| 8 | 8 | NMR1: 2.07 (s, 3H), 7.09 (s, 1H)<br>ESI+: 160/162 |
| 9 | 9 | NMR1; 2.53-2.61 (m, 2H), 2.73-2.80 (m, 2H), 6.58 (s, 1H), 6.68 (s, 1H), 7.14-7.33 (m, 5H), 8.83 (s, 1H), 11.39 (s, 1H)<br>ESI+: 216 |
| 10 | 10 | NMR1: 2.04 (s, 3H), 2.58-2.62 (m, 2H), 2.71-2.74 (m, 2H), 6.56 (s, 1H), 7.16-7.21 (m, 3H), 7.26-7.30 (m, 2H), 8.50 (brs, 1H), 11.39 (brs, 1H),<br>ESI/APCI+: 230 |
| 11 | 11 | ESI+: 255 |
| 12 | 1 | NMR1: 2.75-2.83 (m, 2H), 2.94-3.02 (m, 2H), 6.61 (s, 1H), 7.45 (d, J = 8.0 Hz, 2H), 7.63 (d, J = 8.0 Hz, 2H), 10.74 (brs, 1H), 12.67 (s, 1H)<br>ESI+: 285 |
| 13 | 1 | NMR1: 2.25 (s, 3H), 2.66-2.76 (m, 2H), 2.77-2.86 (m, 2H), 6.57 (s, 1H), 7.02-7.11 (m, 4H), 10.68 (brs, 1H), 12.65 (s, 1H)<br>ESI+: 231 |
| 14 | 1 | NMR1: 2.67-2.74 (m, 2H), 2.76-2.84 (m, 2H), 3.71 (s, 3H), 6.57 (s, 1H), 6.83 (d, J = 8.8 Hz, 2H), 7.11 (d, J = 8.8 Hz, 2H), 10.68 (brs, 1H), 12.65 (s, 1H)<br>ESI+: 247 |
| 15 | 1 | NMR1: 2.76-2.83 (m, 2H), 2.88-2.96 (m, 2H), 6.63 (s, 1H), 7.28-7.37 (m, 3H), 7.41-7.48 (m, 2H), 7.54-7.60 (m, 2H), 7.61-7.66 (m, 2H), 10.72 (brs, 1H), 12.68 (s, 1H)<br>ESI+: 293 |

TABLE 36

| Ex | Syn | Data |
|---|---|---|
| 16 | 1 | NMR1: 2.70-2.79 (m, 2H), 2.80-2.88 (m, 2H), 3.72 (s, 3H), 6.59 (s, 1H), 6.71-6.80 (m, 3H), 7.14-7.21 (m, 1H), 10.69 (brs, 1H), 12.67 (s, 1H)<br>ESI+: 247 |
| 17 | 1 | NMR1: 2.75-2.83 (m, 2H), 2.94-3.03 (m, 2H), 6.62 (s, 1H), 7.47-7.61 (m, 4H), 10.72 (brs, 1H), 12.68 (s, 1H)<br>ESI+: 285 |
| 18 | 1 | NMR1: 2.73-2.80 (m, 2H), 2.86-2.94 (m, 2H), 6.59 (s, 1H), 6.96-7.11 (m, 3H), 7.26-7.34 (m, 1H), 10.72 (brs, 1H), 12.67 (s, 1H)<br>ESI+: 235 |
| 19 | 1 | NMR1: 2.79-2.87 (m, 2H), 3.05-3.14 (m, 2H), 6.63 (s, 1H), 7.90 (s, 1H), 7.96 (s, 2H), 10.75 (brs, 1H), 12.68 (s, 1H)<br>ESI+: 353 |
| 20 | 1 | NMR1: 2.26 (s, 3H), 2.69-2.77 (m, 2H), 2.78-2.86 (m, 2H), 6.57 (s, 1H), 6.95-7.06 (m, 3H), 7.11-7.18 (m, 1H), 10.69 (brs, 1H), 12.66 (s, 1H)<br>ESI+: 231 |
| 21 | 1 | NMR1: 2.68-2.77 (m, 2H), 2.84-2.92 (m, 2H), 6.57 (s, 1H), 6.96-7.04 (m, 1H), 7.11-7.20 (m, 1H), 7.27-7.37 (m, 1H), 10.73 (brs, 1H), 12.66 (s, 1H)<br>ESI+: 253 |
| 22 | 1 | NMR1: 2.27 (s, 3H), 2.66-2.74 (m, 2H), 2.81-2.89 (m, 2H), 6.58 (s, 1H), 7.05-7.17 (m, 4H), 10.70 (brs, 1H), 12.68 (s, 1H)<br>ESI+: 231 |
| 23 | 1 | NMR1: 2.69-2.84 (m, 4H), 3.70 (s, 6H), 6.28-6.32 (m, 1H), 6.35-6.40 (m, 2H), 6.59 (s, 1H), 10.70 (brs, 1H), 12.67 (s, 1H)<br>ESI+: 277 |
| 24 | 24 | NMR1: 2.72-2.81 (m, 2H), 2.87-2.95 (m, 2H), 6.59 (s, 1H), 6.94-7.06 (m, 3H), 10.74 (brs, 1H), 12.68 (s, 1H)<br>ESI+: 253 |
| 25 | 1 | NMR1: 1.25 (s, 9H), 2.69-2.77 (m, 2H), 2.79-2.86 (m, 2H), 6.60 (s, 1H), 7.13 (d, J = 8.4 Hz, 2H), 7.28 (d, J = 8.4 Hz, 2H), 10.70 (brs, 1H), 12.67 (s, 1H)<br>ESI+: 273 |
| 26 | 1 | NMR1: 1.72-1.82 (m, 2H), 2.44-2.52 (m, 2H), 3.22 (s, 3H), 3.31 (t, J = 6.4 Hz, 2H), 6.53 (s, 1H), 10.69 (brs, 1H), 12.65 (s, 1H)<br>ESI+: 185 |
| 27 | 1 | NMR1: 2.71-2.78 (m, 2H), 2.86-2.95 (m, 2H), 6.57 (s, 1H), 7.05-7.16 (m, 2H), 7.19-7.31 (m, 2H), 10.71 (brs, 1H), 12.66 (s, 1H)<br>ESI+: 235 |

TABLE 37

| Ex | Syn | Data |
|---|---|---|
| 28 | 1 | NMR1: 2.70-2.78 (m, 2H), 2.86-2.95 (m, 2H), 6.53 (s, 1H), 7.25 (d, J = 8.0 Hz, 2H), 7.34 (d, J = 8.0 Hz, 2H), 10.79 (brs, 1H), 12.59 (s, 1H)<br>ESI+: 301 |
| 29 | 1 | NMR1: 0.88 (t, J = 7.6 Hz, 3H), 1.22-1.34 (m, 2H), 1.47-1.58 (m, 2H), 2.39-2.47 (m, 2H), 6.53 (s, 1H), 10.67 (brs, 1H), 12.64 (s, 1H)<br>ESI+: 169 |
| 30 | 1 | NMR1: 2.73-2.81 (m, 2H), 3.00-3.08 (m, 2H), 6.59 (s, 1H), 7.39-7.46 (m, 1H), 7.49-7.54 (m, 1H), 7.58-7.64 (m, 1H), 7.65-7.71 (m, 1H), 10.78 (brs, 1H), 12.70 (s, 1H)<br>ESI+: 285 |
| 31 | 1 | NMR1: 1.10 (s, 6H), 1.56-1.65 (m, 2H), 2.45-2.53 (m, 2H), 4.21 (brs, 1H), 6.52 (s, 1H), 10.66 (brs, 1H), 12.62 (s, 1H)<br>ESI+: 199 |
| 32 | 4 | ESI+: 323 |
| 33 | 4 | ESI+: 349 |
| 34 | 4 | ESI+: 333 |

TABLE 37-continued

| Ex | Syn | Data |
|---|---|---|
| 35 | 4 | ESI+: 276 |
| 36 | 4 | ESI+: 302 |
| 37 | 4 | ESI+: 379 |
| 38 | 4 | ESI+: 337 |
| 39 | 4 | ESI+: 301 |
| 40 | 1 | NMR1: 0.81-0.97 (m, 2H), 1.05-1.29 (m, 4H), 1.39-1.50 (m, 2H), 1.55-1.77 (m, 5H), 2.41-2.48 (m, 2H), 6.52 (s, 1H), 10.67 (brs, 1H), 12.63 (s, 1H) ESI+: 223 |
| 41 | 4 | ESI+: 295 |
| 42 | 4 | ESI+: 311 |
| 43 | 4 | ESI+: 277 |
| 44 | 4 | ESI+: 321 |
| 45 | 4 | ESI+: 311 |
| 46 | 4 | ESI+: 346 |
| 47 | 4 | ESI+: 265 |
| 48 | 1 | NMR1: 1.48 (d, J = 7.2 Hz, 3H), 4.00 (q, J = 7.2 Hz, 1H), 6.41 (s, 1H), 7.18-7.35 (m, 5H), 10.72 (brs, 1H), 12.74 (s, 1H) ESI+: 217 |
| 49 | 7 | NMR1; 7.32 (s, 1H) ESI/APCI+: 268/270/272 |
| 50 | 1 | NMR1: 1.11 (t, J = 7.6 Hz, 3H), 2.47 (q, J = 7.6 Hz, 2H), 6.54 (s, 1H), 10.67 (brs, 1H), 12.64 (s, 1H) ESI+: 141 |
| 51 | 7 | NMR1; 7.34 (s, 1H) ESI/APCI+: 224/226/228 |

TABLE 38

| Ex | Syn | Data |
|---|---|---|
| 52 | 1 | NMR1: 1.50-1.62 (m, 4H), 2.42-2.52 (m, 2H), 2.55-2.62 (m, 2H), 6.51 (s, 1H), 7.13-7.21 (m, 3H), 7.23-7.29 (m, 2H), 10.69 (brs, 1H), 12.64 (s, 1H) ESI+: 245 |
| 53 | 1 | NMR1: 1.80-1.92 (m, 2H), 2.42-2.52 (m, 2H), 2.55-2.62 (m, 2H), 6.55 (s, 1H), 7.14-7.23 (m, 3H), 7.24-7.31 (m, 2H), 10.69 (brs, 1H), 12.66 (s, 1H) ESI+: 231 |
| 54 | 2 | NMR1: 6.68-6.78 (m, 1H), 6.87-6.95 (m, 1H) ESI/APCI+: 190/192 |
| 55 | 9 | NMR1: 2.71-2.75 (m, 2H), 2.78-2.83 (m, 2H), 7.10 (s, 1H), 7.18-7.23 (m, 3H), 7.28-7.32 (m, 2H), 9.33 (brs, 1H), 11.91 (brs, 1H), ESI/APCI+: 250/252 |
| 56 | 1 | NMR1: 2.82-2.91 (m, 2H), 3.29-3.41 (m, 2H), 6.66 (s, 1H), 7.32-7.46 (m, 2H), 7.49-7.60 (m, 2H), 7.74-7.80 (m, 1H), 7.89-7.96 (m, 1H), 8.07-8.15 (m, 1H), 10.71 (brs, 1H), 12.68 (s, 1H) ESI+: 267 |
| 57 | 3 | NMR1: 5.05 (s, 2H), 6.56 (s, 1H), 7.64 (s, 1H), 7.67 (s, 2H), 12.76 (brs, 1H) |
| 58 | 9 | NMR1; 0.79-0.95 (m, 2H), 1.05-1.25 (m, 4H), 1.28-1.38 (m, 2H), 1.54-1.75 (m, 5H), 2.21-2.31 (m, 2H), 6.60 (s, 2H), 8.86 (s, 1H), 11.41 (brs, 1H) ESI/APCI+: 222 |
| 59 | 9 | NMR1; 0.90 (s, 9H), 1.27-1.38 (m, 2H), 2.17-2.28 (m, 2H), 6.59-6.64 (m, 2H), 8.85 (s, 1H), 11.42 (brs, 1H) ESI/APCI+: 196 |
| 60 | 5 | ESI+: 223 |
| 61 | 5 | ESI+: 237 |
| 62 | 5 | ESI+: 306 |
| 63 | 5 | ESI+: 343 |
| 64 | 5 | ESI+: 273 |
| 65 | 5 | ESI+: 306 |
| 66 | 5 | ESI+: 277 |
| 67 | 5 | ESI+: 344 |

TABLE 38-continued

| Ex | Syn | Data |
|---|---|---|
| 68 | 5 | ESI+: 288 |
| 69 | 5 | ESI+: 237 |
| 70 | 5 | ESI+: 263 |
| 71 | 5 | ESI+: 349 |
| 72 | 5 | ESI+: 353 |
| 73 | 5 | ESI+: 237 |

TABLE 39

| Ex | Syn | Data |
|---|---|---|
| 74 | 5 | ESI+: 294 |
| 75 | 5 | ESI+: 302 |
| 76 | 5 | ESI+: 313 |
| 77 | 5 | ESI+: 341 |
| 78 | 5 | ESI+: 331 |
| 79 | 5 | ESI+: 339 |
| 80 | 5 | ESI+: 315 |
| 81 | 5 | ESI+: 311 |
| 82 | 5 | ESI+: 250 |
| 83 | 5 | ESI+: 195 |
| 84 | 5 | ESI+: 282 |
| 85 | 5 | ESI+: 275 |
| 86 | 5 | ESI+: 224 |
| 87 | 5 | ESI+: 310 |
| 88 | 5 | ESI+: 359 |
| 89 | 5 | ESI+: 332 |
| 90 | 5 | ESI+: 307 |
| 91 | 5 | ESI+: 315 |
| 92 | 5 | ESI+: 344 |
| 93 | 5 | ESI+: 382 |
| 94 | 5 | ESI+: 306 |
| 95 | 5 | ESI+: 317 |
| 96 | 5 | ESI+: 314 |
| 97 | 5 | ESI+: 314 |
| 98 | 5 | ESI+: 302 |
| 99 | 5 | ESI+: 211 |
| 100 | 5 | ESI+: 329 |
| 101 | 5 | ESI+: 278 |
| 102 | 5 | ESI+: 277 |
| 103 | 5 | ESI+: 336/338 |
| 104 | 5 | ESI+: 277 |
| 105 | 5 | ESI+: 323 |
| 106 | 5 | ESI+: 273 |
| 107 | 5 | ESI+: 321 |
| 108 | 5 | ESI+: 315 |
| 109 | 5 | ESI+: 213 |
| 110 | 5 | ESI+: 354 |
| 111 | 5 | ESI+: 278 |
| 112 | 5 | ESI+: 325 |
| 113 | 5 | ESI+: 353 |
| 114 | 5 | ESI+: 368 |

TABLE 40

| Ex | Syn | Data |
|---|---|---|
| 115 | 5 | ESI+: 244 |
| 116 | 5 | ESI+: 319 |
| 117 | 5 | ESI+: 308 |
| 118 | 5 | ESI+: 267 |
| 119 | 5 | ESI+: 314 |
| 120 | 5 | ESI+: 292 |
| 121 | 1 | NMR1: 0.90 (s, 9H), 1.39-1.48 (m, 2H), 2.37-2.44 (m, 2H), 6.53 (s, 1H), 10.66 (brs, 1H), 12.63 (s, 1H) ESI+: 197 |
| 122 | 5 | ESI+: 305 |
| 123 | 5 | ESI+: 327 |
| 124 | 5 | ESI+: 306 |
| 125 | 5 | ESI+: 280 |
| 126 | 5 | ESI+: 305 |
| 127 | 5 | ESI+: 322 |

TABLE 40-continued

| Ex | Syn | Data |
|---|---|---|
| 128 | 5 | ESI+: 264 |
| 129 | 5 | ESI+: 329 |
| 130 | 5 | ESI+: 329 |
| 131 | 5 | ESI+: 317 |
| 132 | 5 | ESI+: 317 |
| 133 | 5 | ESI+: 305 |
| 134 | 5 | ESI+: 368 |
| 135 | 5 | ESI+: 301 |
| 136 | 5 | ESI+: 329 |
| 137 | 5 | ESI+: 309 |
| 138 | 5 | ESI+: 319 |
| 139 | 5 | ESI+: 278 |
| 140 | 5 | ESI+: 355 |
| 141 | 5 | ESI+: 329 |
| 142 | 5 | ESI+: 372 |
| 143 | 5 | ESI+: 364 |
| 144 | 5 | ESI+: 302 |
| 145 | 5 | ESI+: 318 |
| 146 | 5 | ESI+: 359 |
| 147 | 5 | ESI+: 292 |
| 148 | 5 | ESI+: 345 |
| 149 | 5 | ESI+: 340 |
| 150 | 5 | ESI+: 261 |
| 151 | 5 | ESI+: 355 |
| 152 | 5 | ESI+: 346 |

TABLE 41

| Ex | Syn | Data |
|---|---|---|
| 153 | 5 | ESI+: 306 |
| 154 | 5 | ESI+: 329 |
| 155 | 5 | ESI+: 308 |
| 156 | 5 | ESI+: 337 |
| 157 | 5 | ESI+: 310 |
| 158 | 5 | ESI+: 317 |
| 159 | 5 | ESI+: 258 |
| 160 | 5 | ESI+: 322 |
| 161 | 5 | ESI+: 266 |
| 162 | 5 | ESI+: 224 |
| 163 | 5 | ESI+: 320 |
| 164 | 5 | ESI+: 321 |
| 165 | 5 | ESI+: 291 |
| 166 | 5 | ESI+: 244 |
| 167 | 5 | ESI+: 319/321 |
| 168 | 5 | ESI+: 251 |
| 169 | 5 | ESI+: 299 |
| 170 | 5 | ESI+: 169 |
| 171 | 5 | ESI+: 211 |
| 172 | 5 | ESI+: 211 |
| 173 | 5 | ESI+: 209 |
| 174 | 5 | ESI+: 223 |
| 175 | 5 | ESI+: 225 |
| 176 | 5 | ESI+: 238 |
| 177 | 5 | ESI+: 296 |
| 178 | 5 | ESI+: 291 |
| 179 | 5 | ESI+: 237 |
| 180 | 5 | ESI+: 252 |
| 181 | 5 | ESI+: 266 |
| 182 | 5 | ESI+: 312/314 |
| 183 | 5 | ESI+: 302/304/306 |
| 184 | 5 | ESI+: 302/304/306 |
| 185 | 5 | ESI+: 276 |
| 186 | 5 | ESI+: 248 |
| 187 | 5 | ESI+: 252 |
| 188 | 5 | ESI+: 291 |
| 189 | 5 | ESI+: 264 |
| 190 | 5 | ESI+: 262 |
| 191 | 5 | ESI+: 262 |
| 192 | 5 | ESI+: 290 |

TABLE 42

| Ex | Syn | Data |
|---|---|---|
| 193 | 5 | ESI+: 262 |
| 194 | 5 | ESI+: 302 |
| 195 | 5 | ESI+: 252 |
| 196 | 5 | ESI+: 302/304/306 |
| 197 | 5 | ESI+: 302/304/306 |
| 198 | 5 | ESI+: 282/284 |
| 199 | 5 | ESI+: 286/288 |
| 200 | 5 | ESI+: 292 |
| 201 | 5 | ESI+: 280 |
| 202 | 5 | ESI+: 304 |
| 203 | 5 | ESI+: 396/398 |
| 204 | 5 | ESI+: 270 |
| 205 | 5 | ESI+: 292 |
| 206 | 5 | ESI+: 312/314 |
| 207 | 5 | ESI+: 282 |
| 208 | 5 | ESI+: 318 |
| 209 | 5 | ESI+: 262 |
| 210 | 5 | ESI+: 264 |
| 211 | 5 | ESI+: 278 |
| 212 | 1 | NMR1: 2.69-2.78 (m, 2H), 2.82-2.91 (m, 2H), 6.58 (s, 1H), 7.04-7.13 (m, 2H), 7.20-7.28 (m, 2H), 10.71 (brs, 1H), 12.67 (s, 1H) ESI+: 235 |
| 213 | 11 | ESI+: 269 |
| 214 | 11 | ESI+: 269 |
| 215 | 11 | ESI+: 283 |
| 216 | 11 | ESI+: 295 |
| 217 | 11 | ESI+: 275 |
| 218 | 11 | ESI+: 292 |
| 219 | 11 | ESI+: 281 |
| 220 | 11 | ESI+: 295 |
| 221 | 11 | ESI+: 267 |
| 222 | 11 | ESI+: 311 |
| 223 | 11 | ESI+: 325 |
| 224 | 11 | ESI+: 359 |
| 225 | 11 | ESI+: 337 |
| 226 | 11 | ESI+: 357 |

TABLE 43

| Ex | Syn | Data |
|---|---|---|
| 227 | 11 | ESI+: 371 |
| 228 | 11 | ESI+: 373 |
| 229 | 1 | NMR1: 0.87 (t, J = 7.6 Hz, 3H), 1.56 (qt J = 7.6, 7.6 Hz, 2H), 2.38-2.44 (m, 2H), 6.53 (s, 1H), 10.67 (brs, 1H), 12.64 (s, 1H) ESI+: 155 |
| 230 | 3 | NMR1: 5.09 (s, 2H), 6.78 (s, 1H), 7.04-7.06 (m, 1H), 7.40-7.44 (m, 1H), 7.49-7.56 (m, 3H), 7.87-7.90 (m, 1H), 8.15-8.17 (m, 1H), 12.93 (brs, 1H) ESI+: 269 |
| 231 | 3 | NMR1: 4.82 (s, 2H), 6.50 (s, 1H), 6.98-7.02 (m, 2H), 7.10-7.14 (m, 2H), 12.69 (s, 1H) ESI+: 237 |
| 232 | 3 | NMR1: 4.90 (s, 2H), 6.66 (s, 1H), 6.76-6.92 (m, 3H), 7.29-7.35 (m, 1H), 12.91 (s, 1H) ESI+: 237 |
| 233 | 3 | NMR1: 2.27 (s, 3H), 4.86 (s, 2H), 6.68 (s, 1H), 6.76-6.82 (m, 3H), 7.14-7.18 (m, 1H), 11.05 (brs, 1H), 12.94 (s, 1H) ESI+: 233 |
| 234 | 3 | NMR1: 3.76 (s, 3H), 4.85 (s, 2H), 6.70 (s, 1H), 6.84-7.02 (m, 4H), 12.92 (s, 1H) ESI+: 249 |
| 235 | 3 | NMR1: 3.72 (s, 3H), 4.87 (s, 2H), 6.53-6.59 (m, 3H), 6.69 (s, 1H), |

TABLE 43-continued

| Ex | Syn | Data |
|---|---|---|
| | | 7.16-7.21 (m, 1H), 12.96 (s, 1H)<br>ESI+: 249 |
| 236 | 1 | NMR1: 1.11-1.41 (m, 5H), 1.61-1.84 (m, 5H), 2.32-2.45 (m, 1H), 6.57 (s, 1H), 10.64 (brs, 1H), 12.65 (s, 1H)<br>ESI+: 195 |
| 237 | 3 | NMR1: 4.88 (s, 2H), 6.68 (s, 1H), 6.93-7.01 (m, 3H), 7.27-7.32 (m, 2H), 12.93 (s, 1H)<br>ESI+: 219 |
| 238 | 3 | ESI−: 271 |
| 239 | 3 | ESI+: 289 |

TABLE 44

| Ex | Syn | Data |
|---|---|---|
| 240 | 3 | NMR1: 2.15 (s, 3H), 4.87 (s, 2H), 6.68 (s, 1H), 6.82-6.86 (m, 1H), 6.94-6.96 (m, 1H), 7.10-7.14 (m, 2H), 12.91 (s, 1H)<br>ESI+: 233 |
| 241 | 3 | ESI+: 233 |
| 242 | 3 | NMR1: 4.92 (s, 2H), 6.69 (s, 1H), 7.05-7.08 (m, 2H), 7.27-7.31 (m, 1H), 7.38-7.43 (m, 2H), 7.57-7.59 (m, 4H), 12.94 (s, 1H)<br>ESI+: 295 |
| 243 | 3 | NMR1: 4.95 (s, 2H), 6.60 (s, 1H), 7.15-7.17 (m, 2H), 7.63-7.66 (m, 2H), 11.24 (br, 1H), 12.83 (s, 1H)<br>ESI+: 287 |
| 244 | 3 | NMR1: 4.95 (s, 2H), 6.62 (s, 1H), 7.28-7.31 (m, 3H), 7.49-7.53 (m, 1H), 11.19 (br, 1H), 12.85 (s, 1H)<br>ESI+: 287 |
| 245 | 3 | NMR1: 5.04 (s, 2H), 6.63 (s, 1H), 7.09-7.13 (m, 1H), 7.29-7.32 (m, 1H), 7.59-7.64 (m, 2H), 11.12 (brs, 1H), 12.97 (s, 1H)<br>ESI+: 287 |
| 246 | 3 | NMR1: 4.93, (s, 2H), 6.69 (s, 1H), 6.97-7.03 (m, 1H), 7.20-7.32 (m, 2H), 11.09 (s, 1H), 12.95 (s, 1H)<br>ESI+: 255 |
| 247 | 3 | NMR1: 4.92 (s, 2H), 6.67 (s, 1H), 6.92-7.05 (m, 3H), 7.38-7.42 (m, 1H), 11.12 (s, 1H), 12.93 (s, 1H)<br>ESI+: 303 |
| 248 | 3 | NMR1: 2.55 (s, 3H), 4.95 (s, 2H), 6.70 (s, 1H), 7.24-7.27 (m, 1H), 7.42-7.56 (m, 3H), 11.08 (br, 1H), 12.97 (brs, 1H)<br>ESI+: 261 |
| 249 | 3 | NMR1; 1.93-2.01 (m, 2H), 2.72-2.80 (m, 4H), 4.80 (s, 2H), 6.59 (s, 1H), 6.70 (s, 1H), 6.84-6.85 (m, 1H), 7.06-7.09 (m, 1H), 12.83 (s, 1H)<br>ESI+: 259 |
| 250 | 3 | NMR1; 3.16 (s, 3H), 5.02 (s, 2H), 6.68 (s, 1H), 7.22-7.24 (m, 2H), 7.84-7.86 (m, 2H), 12.97 (s, 1H)<br>ESI+: 297 |
| 251 | 3 | NMR1; 4.93 (s, 2H), 6.65 (s, 1H), 6.92-7.02 (m, 2H), 7.32-7.36 (m, 1H), 7.40-7.49 (m, 5H), 12.89 (s, 1H)<br>ESI+: 313 |

TABLE 45

| Ex | Syn | Data |
|---|---|---|
| 252 | 3 | NMR1; 3.77 (s, 3H), 4.81 (s, 2H), 6.34 (brs, 1H), 6.91-6.94 (m, 1H), 7.21 (s, 1H), 7.41-7.43 (m, 1H), 8.07 (s, 1H), 12.50 (brs, 1H)<br>ESI+: 273 |

TABLE 45-continued

| Ex | Syn | Data |
|---|---|---|
| 253 | 3 | NMR1; 2.36 (s, 3H), 4.91 (s, 2H), 6.68 (s, 1H), 7.14-7.17 (m, 1H), 7.31-7.33 (m, 1H), 8.16-8.17 (m, 1H), 12.94 (s, 1H)<br>ESI+: 234 |
| 254 | 2 | NMR1; 2.71-2.74 (m, 2H), 2.85-2.89 (m, 2H), 6.52 (s, 1H), 7.23 (d, J = 8.0 Hz, 2H), 7.31 (d, J = 8.0 Hz, 2H), 10.73 (brs, 1H), 12.63 (s, 1H)<br>ESI+: 251/253 |

TABLE 46

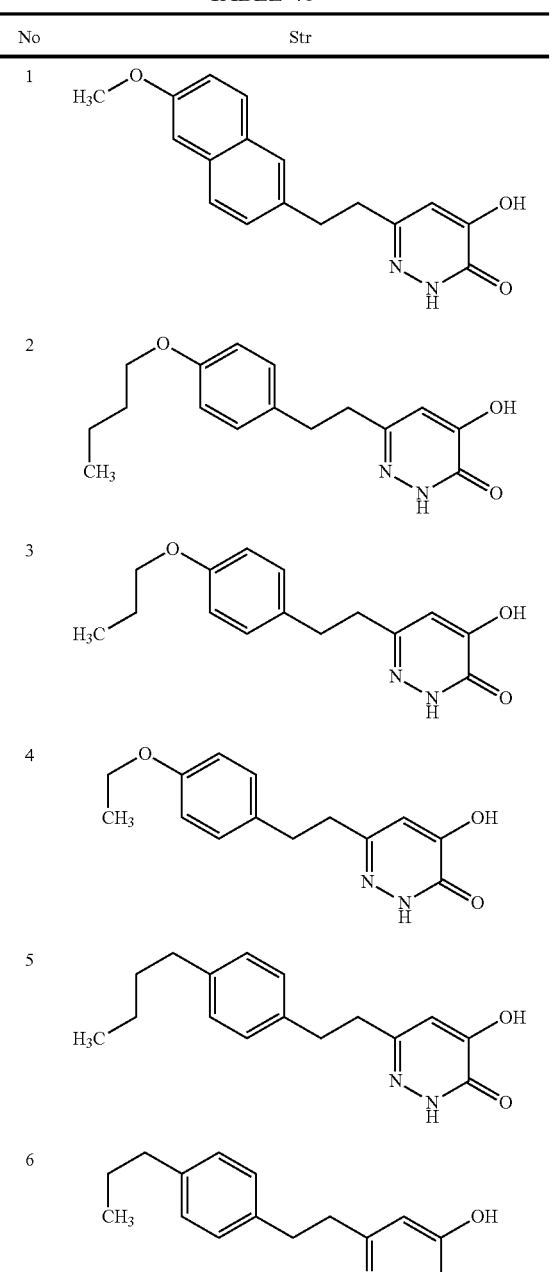

TABLE 46-continued
| No | Str |
|---|---|
| 7 | 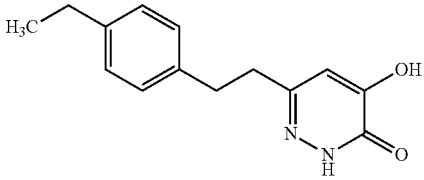 [SMILES: CCc1ccc(CCc2cc(O)c(=O)[nH]n2)cc1] |
| 8 | 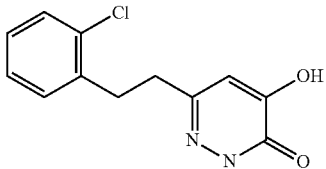 |
| 9 | 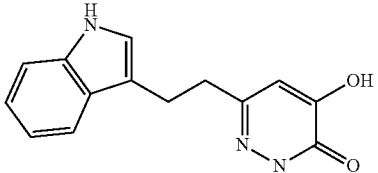 |
| 10 | 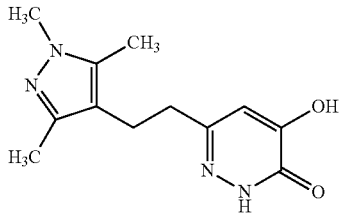 [SMILES: Cc1nn(C)c(C)c1CCc1cc(O)c(=O)[nH]n1] |
| 11 | 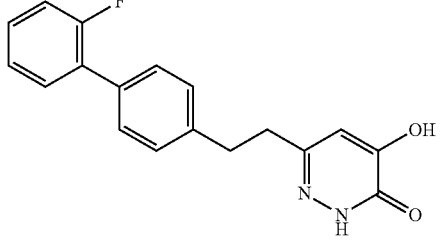 |
| 12 | 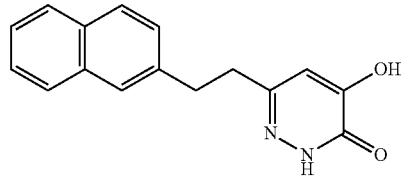 [SMILES: O=c1[nH]nc(CCc2ccc3ccccc3c2)cc1O] |
| 13 | 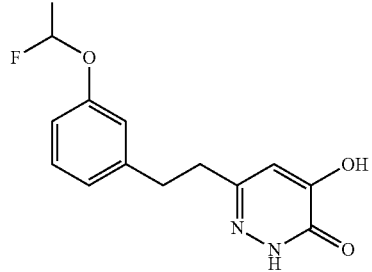 |
TABLE 46-continued
| No | Str |
|---|---|
| 14 | 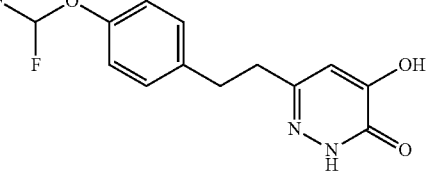 |
TABLE 47
| No | Str |
|---|---|
| 15 | 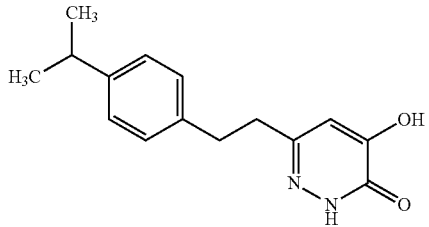 [SMILES: CC(C)c1ccc(CCc2cc(O)c(=O)[nH]n2)cc1] |

TABLE 47-continued
| No | Str |
|---|---|
| 21 | 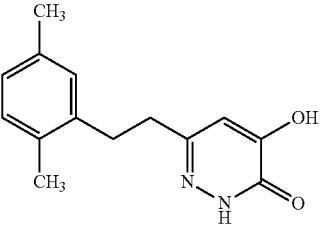 [SMILES: Cc1ccc(C)c(CCc2cc(O)c(=O)[nH]n2)c1] |
| 22 | 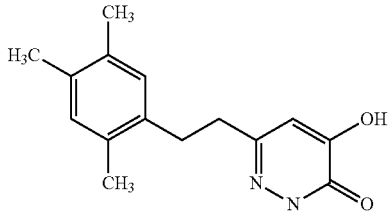 |
| 23 | 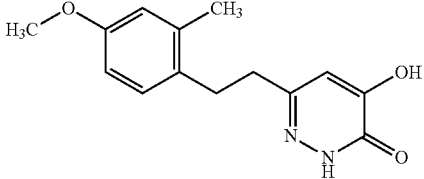 [SMILES: COc1ccc(CCc2cc(O)c(=O)[nH]n2)c(C)c1] |
| 24 | 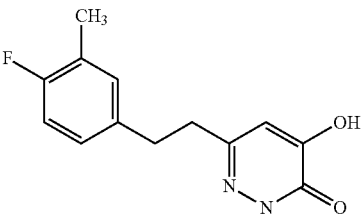 |
| 25 | 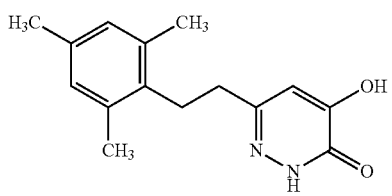 [SMILES: Cc1cc(C)c(CCc2cc(O)c(=O)[nH]n2)c(C)c1] |
| 26 | 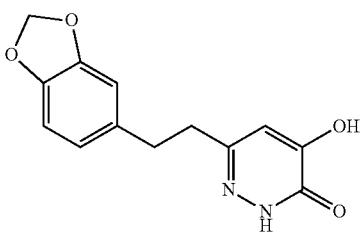 [SMILES: O=c1[nH]nc(CCc2ccc3c(c2)OCO3)cc1O] |
| 27 | 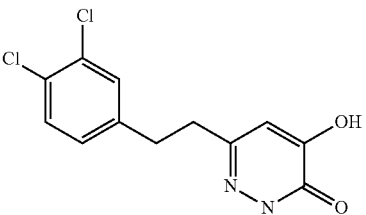 |
TABLE 48
| No | Str |
|---|---|
| 28 | 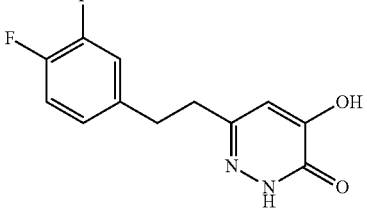 |
| 29 | 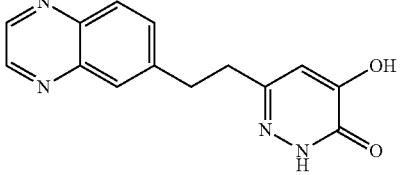 |
| 30 | 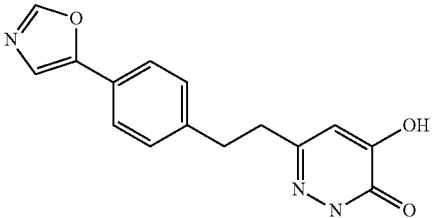 |
| 31 | 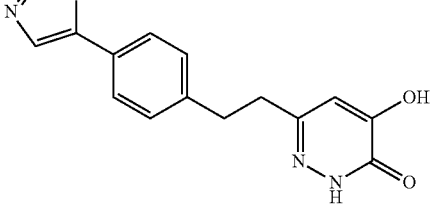 |
| 32 | 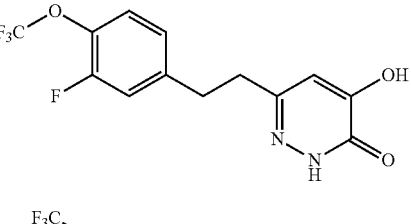 |
| 33 | 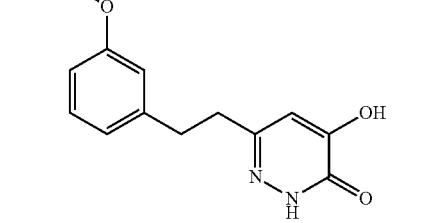 |
| 34 | 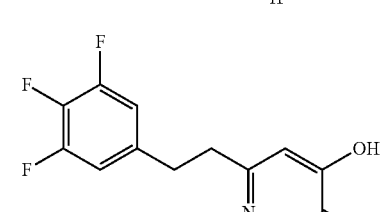 |

TABLE 48-continued

| No | Str |
|---|---|
| 35 | 3-fluoro-4-methylphenethyl pyridazinone |
| 36 | 3-fluoro-4-methoxyphenethyl pyridazinone |
| 37 | 2-ethylphenethyl pyridazinone |
| 38 | 2,6-dimethylphenethyl pyridazinone |
| 39 | 2,4-dimethylphenethyl pyridazinone |
| 40 | 3,5-dimethylphenethyl pyridazinone |

TABLE 49

| No | Str |
|---|---|
| 41 | 2,3-dimethylphenethyl pyridazinone |
| 42 | 2,3-difluorophenethyl pyridazinone |
| 43 | 2,6-difluorophenethyl pyridazinone |
| 44 | 2,4,6-trifluorophenethyl pyridazinone |
| 45 | 4-ethoxy-3-methoxyphenethyl pyridazinone |
| 46 | 2-(1H-pyrrol-2-yl)ethyl pyridazinone |
| 47 | 2-(4-methoxynaphthalen-1-yl)ethyl pyridazinone |

TABLE 49-continued

| No | Str |
|---|---|
| 48 | (pentafluorophenyl)ethyl-4-hydroxy-pyridazin-3(2H)-one |
| 49 | 2-(1-methyl-1H-pyrrol-2-yl)ethyl-4-hydroxy-pyridazin-3(2H)-one |
| 50 | 2-(2-methoxynaphthalen-1-yl)ethyl-4-hydroxy-pyridazin-3(2H)-one |
| 51 | 2-(9-ethyl-9H-carbazol-3-yl)ethyl-4-hydroxy-pyridazin-3(2H)-one |
| 52 | 2-(2-ethoxyphenyl)ethyl-4-hydroxy-pyridazin-3(2H)-one |

TABLE 50

| No | Str |
|---|---|
| 53 | 2-(3-phenoxyphenyl)ethyl-4-hydroxy-pyridazin-3(2H)-one |
| 54 | 2-(2,3,6-trichlorophenyl)ethyl-4-hydroxy-pyridazin-3(2H)-one |
| 55 | 2-(4-chloro-2-fluorophenyl)ethyl-4-hydroxy-pyridazin-3(2H)-one |
| 56 | 2-(4-chloro-3-fluorophenyl)ethyl-4-hydroxy-pyridazin-3(2H)-one |
| 57 | 2-(2,6-dimethoxyphenyl)ethyl-4-hydroxy-pyridazin-3(2H)-one |
| 58 | 2-(3-chloro-4-fluorophenyl)ethyl-4-hydroxy-pyridazin-3(2H)-one |
| 59 | 2-(4-fluoro-2-(trifluoromethyl)phenyl)ethyl-4-hydroxy-pyridazin-3(2H)-one |
| 60 | 2-(2-ethoxynaphthalen-1-yl)ethyl-4-hydroxy-pyridazin-3(2H)-one |

TABLE 50-continued
| No | Str |
|---|---|
| 61 | |
| 62 | |
| 63 | |
| 64 | |
| 65 | |
TABLE 51
| No | Str |
|---|---|
| 66 | |
TABLE 51-continued
| No | Str |
|---|---|
| 67 | |
| 68 | |
| 69 | |
| 70 | |
| 71 | |
| 72 | 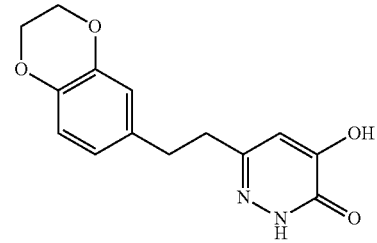 [SMILES: O=c1[nH]nc(CCc2ccc3c(c2)OCCO3)cc1O] |

TABLE 51-continued
| No | Str |
|----|-----|
| 73 | 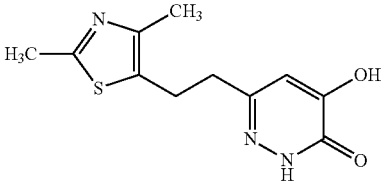 [SMILES: Cc1nc(C)c(CCc2cc(O)c(=O)[nH]n2)s1] |
| 74 | 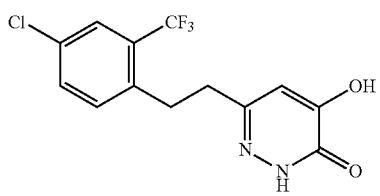 [SMILES: O=c1[nH]nc(CCc2ccc(Cl)cc2C(F)(F)F)cc1O] |
| 75 | 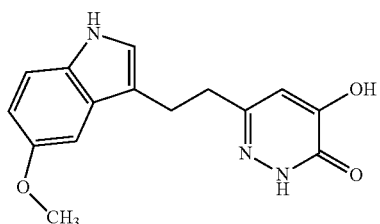 |
| 76 | 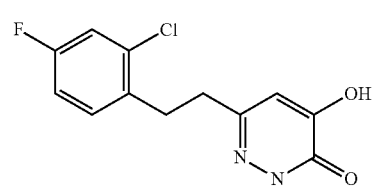 |
| 77 | 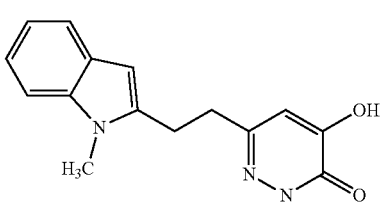 |
| 78 | 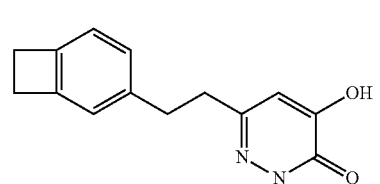 |
TABLE 52
| No | Str |
|----|-----|
| 79 | 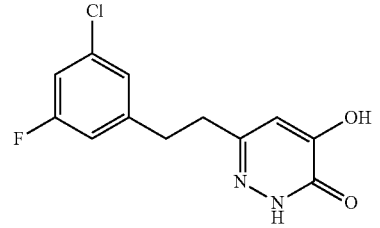 [SMILES: O=c1[nH]nc(CCc2cc(F)cc(Cl)c2)cc1O] |
| 80 | 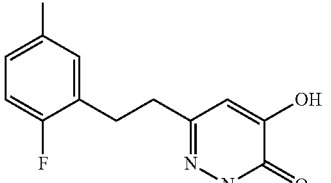 |
| 81 | 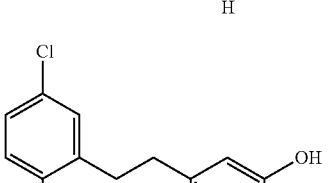 |
| 82 | 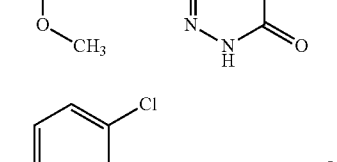 |
| 83 | 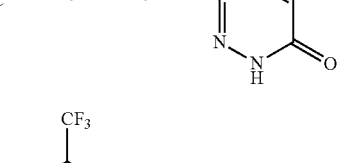 |
| 84 | 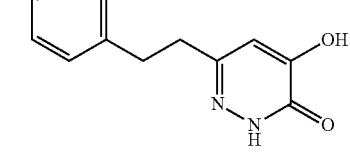 |
| 85 | 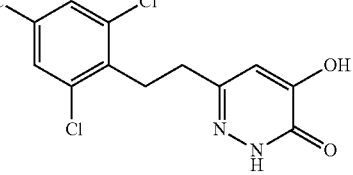 |
| 86 | 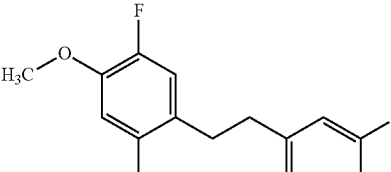 |

TABLE 52-continued
| No | Str |
|---|---|
| 87 | 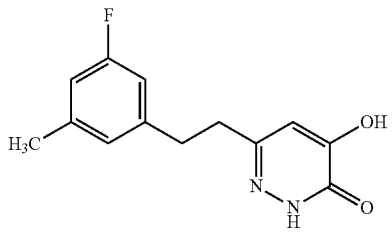 |
| 88 | 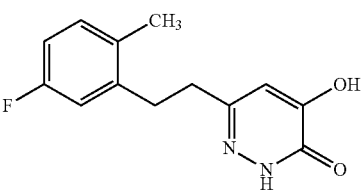 [SMILES: Cc1ccc(F)cc1CCc1cc(O)c(=O)[nH]n1] |
| 89 | 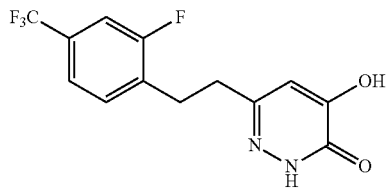 [SMILES: O=c1[nH]nc(CCc2ccc(C(F)(F)F)cc2F)cc1O] |
| 90 | 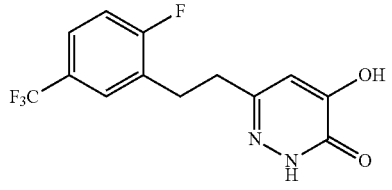 [SMILES: O=c1[nH]nc(CCc2cc(C(F)(F)F)ccc2F)cc1O] |
| 91 | 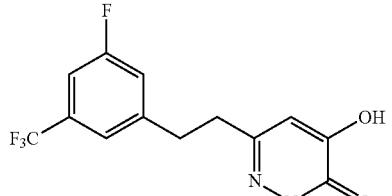 |
TABLE 53
| No | Str |
|---|---|
| 92 | 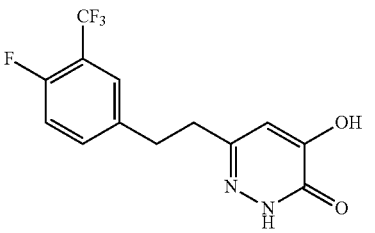 [SMILES: O=c1[nH]nc(CCc2ccc(F)c(C(F)(F)F)c2)cc1O] |
| 93 | 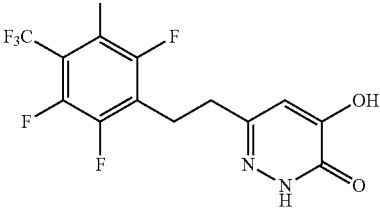 |
| 94 | 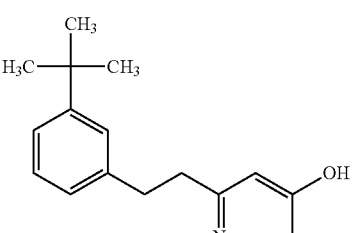 |
| 95 | 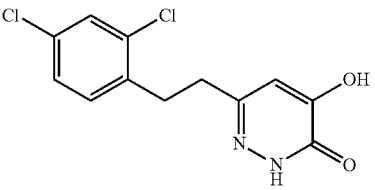 [SMILES: O=c1[nH]nc(CCc2ccc(Cl)cc2Cl)cc1O] |
| 96 | 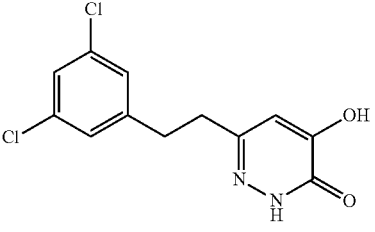 [SMILES: O=c1[nH]nc(CCc2cc(Cl)cc(Cl)c2)cc1O] |
| 97 | 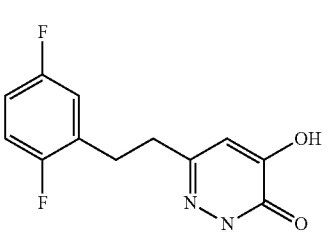 |
| 98 | 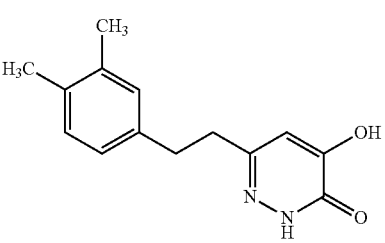 [SMILES: Cc1ccc(CCc2cc(O)c(=O)[nH]n2)cc1C] |

TABLE 53-continued
| No | Str |
|---|---|
| 99 | 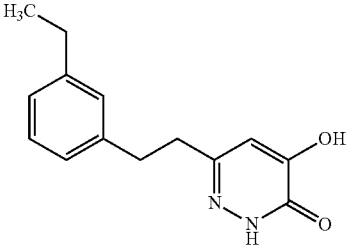 |
| 100 | 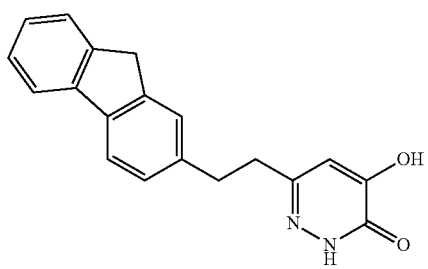 [SMILES: O=c1[nH]nc(CCc2ccc3c(c2)Cc2ccccc2-3)cc1O] |
| 101 | 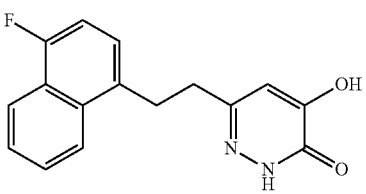 [SMILES: O=c1[nH]nc(CCc2ccc(F)c3ccccc23)cc1O] |
| 102 | 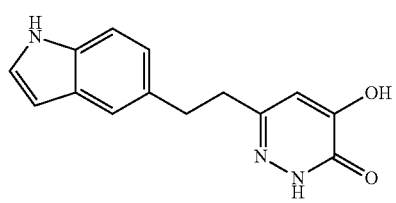 [SMILES: O=c1[nH]nc(CCc2ccc3[nH]ccc3c2)cc1O] |
| 103 | 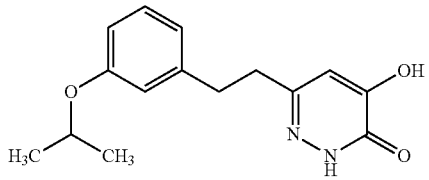 [SMILES: CC(C)Oc1cccc(CCc2cc(O)c(=O)[nH]n2)c1] |
| 104 | 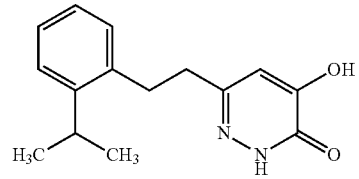 |
TABLE 54
| No | Str |
|---|---|
| 105 | 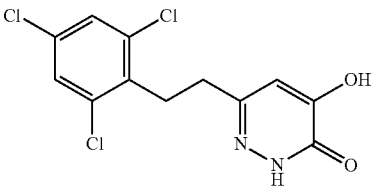 [SMILES: O=c1[nH]nc(CCc2c(Cl)cc(Cl)cc2Cl)cc1O] |
| 106 | 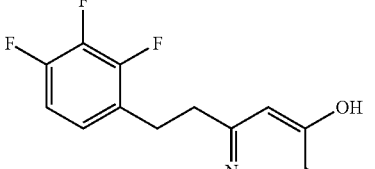 |
| 107 | 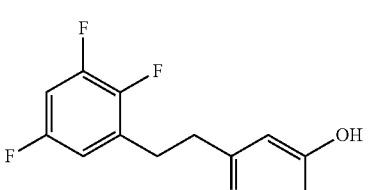 |
| 108 | 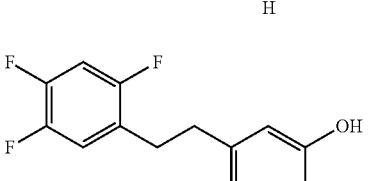 |
| 109 | 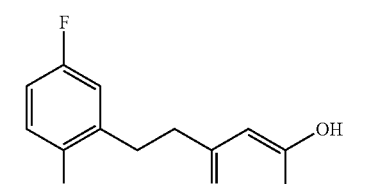 |
| 110 | 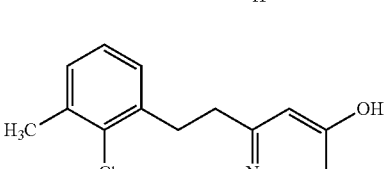 |
| 111 | 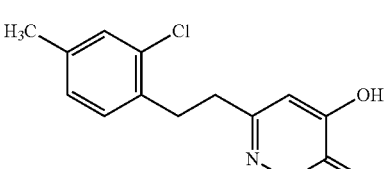 |

TABLE 54-continued

| No | Str |
|---|---|
| 112 | |
| 113 | |
| 114 | |
| 115 | |
| 116 | |
| 117 | |

TABLE 55

| No | Str |
|---|---|
| 118 | |
| 119 | |
| 120 | |
| 121 | |
| 122 | |
| 123 | |
| 124 | |
| 125 | |

TABLE 55-continued
| No | Str |
|---|---|
| 126 | 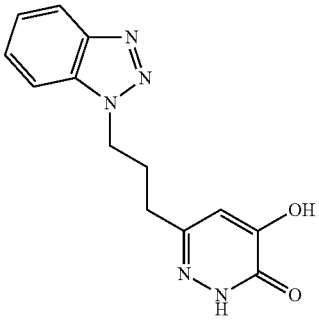 [SMILES: O=c1[nH]nc(CCCn2nnc3ccccc32)cc1O] |
| 127 | 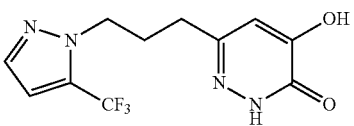 [SMILES: O=c1[nH]nc(CCCn2nccc2C(F)(F)F)cc1O] |
| 128 | 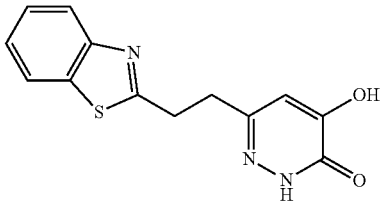 [SMILES: O=c1[nH]nc(CCc2nc3ccccc3s2)cc1O] |
| 129 | 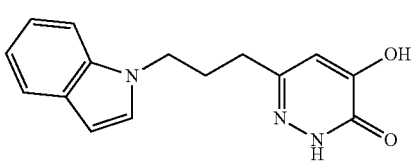 [SMILES: O=c1[nH]nc(CCCn2ccc3ccccc32)cc1O] |
| 130 | 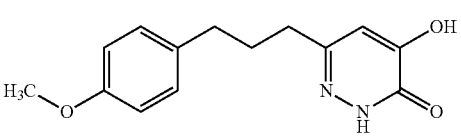 [SMILES: COc1ccc(CCCc2cc(O)c(=O)[nH]n2)cc1] |
| 131 | 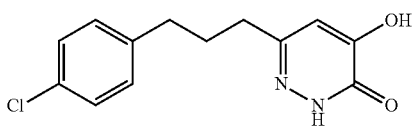 [SMILES: O=c1[nH]nc(CCCc2ccc(Cl)cc2)cc1O] |
| 132 | 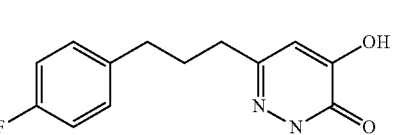 |
| 133 | 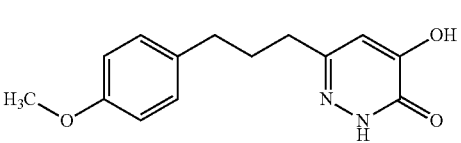 [SMILES: COc1ccc(CCCc2cc(O)c(=O)[nH]n2)cc1] |
TABLE 56
| No | Str |
|---|---|
| 134 | 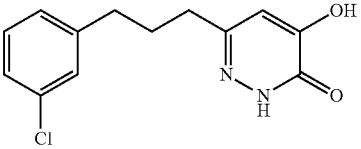 [SMILES: O=c1[nH]nc(CCCc2cccc(Cl)c2)cc1O] |
| 135 | 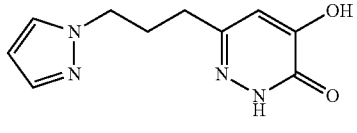 [SMILES: O=c1[nH]nc(CCCn2cccn2)cc1O] |
| 136 | 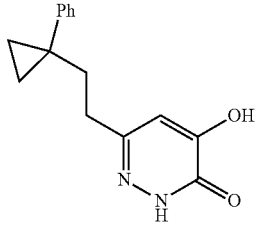 [SMILES: O=c1[nH]nc(CCC2(c3ccccc3)CC2)cc1O] |
| 137 | 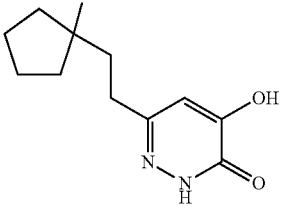 |
| 138 | 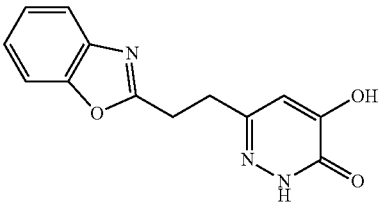 [SMILES: O=c1[nH]nc(CCc2nc3ccccc3o2)cc1O] |
| 139 | 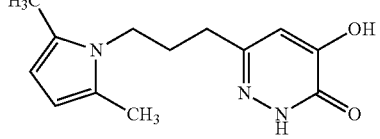 |
| 140 | 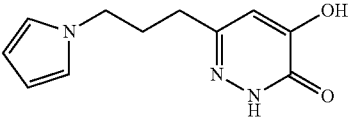 [SMILES: O=c1[nH]nc(CCCn2cccc2)cc1O] |
| 141 | 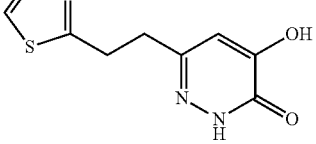 |
| 142 | 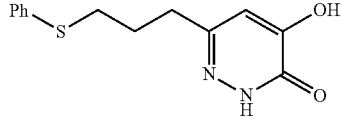 |

TABLE 56-continued

| No | Str |
|---|---|
| 143 | Ph-O-(CH2)3-pyridazinone-OH |
| 144 | 2,6-dichlorophenyl-O-(CH2)3-pyridazinone-OH |
| 145 | isatin-N-(CH2)3-pyridazinone-OH |
| 146 | 4-methylphenyl-NH-(CH2)3-pyridazinone-OH |
| 147 | Ph-NH-(CH2)3-pyridazinone-OH |
| 148 | naphthalen-1-yl-O-(CH2)3-pyridazinone-OH |
| 149 | Ph2N-(CH2)3-pyridazinone-OH |
| 150 | 4-chlorophenyl-O-(CH2)3-pyridazinone-OH |

TABLE 57

| No | Str |
|---|---|
| 151 | 4-(F3C)phenyl-O-(CH2)3-pyridazinone-OH |
| 152 | 3-(F3C)phenyl-O-(CH2)3-pyridazinone-OH |
| 153 | 2-(F3CO)phenyl-O-(CH2)3-pyridazinone-OH |
| 154 | 2-chlorophenyl-O-(CH2)3-pyridazinone-OH |
| 155 | Ph-NH-CH2-pyridazinone-OH |
| 156 | pyridin-3-yl-(CH2)2-pyridazinone-OH |
| 157 | cyclopropyl-CH2-CH2-pyridazinone-OH |
| 158 | 1-methylimidazol-5-yl-(CH2)2-pyridazinone-OH |
| 159 | thiophen-2-yl-(CH2)2-pyridazinone-OH |

TABLE 57-continued

| No | Str |
|---|---|
| 160 | |
| 161 | |
| 162 | |
| 163 | |
| 164 | |
| 165 | |
| 166 | |

INDUSTRIAL APPLICABILITY

The compound of the formula (I) or a salt thereof has a DAAO inhibitory action and can be used, for example, as a prophylaxis and/or therapeutic agent for schizophrenia or neuropathic pain.

The invention claimed is:

1. A method for the treatment of a disease associated with DAAO, wherein the disease associated with DAAO is schizophrenia or neuropathic pain, comprising administering to a subject in need thereof an effective amount of a compound of formula (I) or a salt thereof:

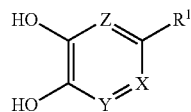

(I)

wherein
X is $CR^2$,
Y is N,
Z is CH,
$R^1$ is chosen from H, $C_{1-10}$ alkyl, -lower alkylene-$OR^3$, halogen, unsubstituted or substituted cycloalkyl, -$L^1$-$R^4$ or -$L^2$-N(—$R^5$)$R^6$,
$R^2$ is chosen from lower alkyl, halogen or -lower alkylene-aryl,
$R^3$ is chosen from H or lower alkyl,
$L^1$ is chosen from -lower alkylene-, -lower alkenylene-, -lower alkylene-O—, -lower alkylene-S(O)$_m$— or -lower alkylene-C(O)—,
$L^2$ is chosen from -lower alkylene-, -lower alkylene-S(O)$_2$— or -lower alkylene -C(O)—,
$R^4$ is chosen from unsubstituted or substituted cycloalkyl, unsubstituted or substituted aryl, unsubstituted or substituted nonaromatic heterocycle or unsubstituted or substituted aromatic heterocycle,
$R^5$ is chosen from H, lower alkyl, unsubstituted or substituted cycloalkyl or unsubstituted or substituted aryl,
$R^6$ is chosen from lower alkyl, -$L^{21}$-(unsubstituted or substituted cycloalkyl), -$L^{21}$-(unsubstituted or substituted aryl), -$L^{21}$-(unsubstituted or substituted nonaromatic heterocycle), -$L^{21}$-(unsubstituted or substituted aromatic heterocycle), -lower alkylene-$OR^7$ or -lower alkylene-N($R^8$)$_2$,
$R^7$ is chosen from H or lower alkyl,
$R^8$ are the same or different and each is lower alkyl,
$L^{21}$ is chosen from a bond or -lower alkylene-, and
m is chosen from an integer of 0 to 2.

2. A compound of formula (I) or a salt thereof:

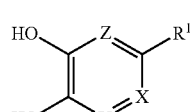

(I)

wherein
X is $CR^2$,
Y is N,
Z is CH,
$R^1$ is -$L^1$ -$R^4$,
$R^2$ is chosen from H, lower alkyl, halogen or -lower alkylene-aryl,
$L^1$ is chosen from -lower alkylene-, -lower alkenylene-, -lower alkylene-O—, -lower alkylene-S(O)$_m$— or -lower alkylene-C(O)—,
$R^4$ is chosen from unsubstituted or substituted cycloalkyl, unsubstituted or substituted aryl, unsubstituted or substituted nonaromatic heterocycle or unsubstituted or substituted aromatic heterocycle,
m is chosen from an integer of 0 to 2.

3. The compound according to claim 2, wherein $L^1$ is lower alkylene, and $R^4$ is chosen from unsubstituted or substituted aryl or unsubstituted or substituted aromatic heterocycle.

4. The compound according to claim 2, wherein $R^2$ is -lower alkylene-aryl.

5. The compound according to claim 2, wherein $R^2$ is halogen.

6. The compound according to claim 2, wherein $R^2$ is lower alkyl.

7. The compound according to claim 2, which is 6-methyl-5-phenethylpyridine-2,3-diol, or a salt thereof.

8. A pharmaceutical composition comprising the compound according to claim 2 and a pharmaceutically acceptable excipient.

9. The pharmaceutical composition according to claim 8, which is for the prophylaxis or treatment of a disease associated with DAAO, wherein the disease is schizophrenia or neuropathic pain.

10. A method for the treatment of a disease associated with DAAO, wherein the disease associated with DAAO is schizophrenia or neuropathic pain, comprising administering to a subject in need thereof an effective amount of the compound according to claim 2.

11. The method according to claim 10, wherein the subject is a human subject.

12. The method according to claim 1, wherein the subject is a human subject.

* * * * *